US007371850B1

(12) United States Patent
Morham et al.

(10) Patent No.: US 7,371,850 B1
(45) Date of Patent: May 13, 2008

(54) METHOD AND COMPOSITION FOR REDUCING EXPRESSION OF ROCK-II

(75) Inventors: Scott Morham, Salt Lake City, UT (US); Gongping He, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 388 days.

(21) Appl. No.: 10/923,262

(22) Filed: Aug. 20, 2004

Related U.S. Application Data

(60) Provisional application No. 60/496,950, filed on Aug. 20, 2003.

(51) Int. Cl.
*C07H 21/02* (2006.01)
*C07H 21/04* (2006.01)

(52) U.S. Cl. .................. 536/24.5; 536/23.1; 536/24.3; 536/24.33

(58) Field of Classification Search ............... 536/23.1, 536/24.3, 24.33, 24.5; 435/6, 91.1, 325, 435/375; 514/44
See application file for complete search history.

(56) References Cited

U.S. PATENT DOCUMENTS 6,218,410 B1 4/2001 Uehata et al.
6,451,825 B1 9/2002 Uehata et al.
6,814,968 B1 11/2004 Graham et al.
6,906,061 B2 6/2005 Uehata et al.
6,977,262 B2 12/2005 Kohara et al.
2002/0173622 A1 11/2002 Wettstein et al.
2002/0177207 A1 11/2002 Sugiyama et al.
2004/0115641 A1 6/2004 Cowsert et al.
2004/0138272 A1 7/2004 McKerracher et al.
2004/0191240 A1 9/2004 Tohyamay et al.
2004/0191291 A1 9/2004 Tohyamay et al.

FOREIGN PATENT DOCUMENTS

WO WO 2004/022541 3/2004

OTHER PUBLICATIONS

Nakamura et al. Role of the small GTP-binding protien Rho in epithelial cell migration in the rabbit cornea. Invest Ophthalmol Via Sci, 2001 vol. 42:941-947.*
Ishikawa et al. Prediction of the coding sequences of unidentified human genes. X. The complete sequences of 100 new cDNA clones from brain which can code for large proteins in vitro. DNA Research, 1998 vol. 5:169-176.*
Shi, Y. Mammailian RNAi for the masses. Trends in Genetics, 2003 vol. 19:9-12.*
Capodici et al. Inhibition of HIV-1 infection by small interfering RNA-mediated RNA interference. Journal of Immunology. 2002 vol. 169:5196-5201.*
GenBank Sequence-Accession No. AB014519, Jul. 15, 1998.*

(Continued)

*Primary Examiner*—Sean McGarry
*Assistant Examiner*—Terra C. Gibbs
(74) *Attorney, Agent, or Firm*—Herbert L. Ley, III; Jay Z. Zhang; Myriad IP Department

(57) ABSTRACT

Methods and pharmaceutical compositions for treating, and delaying the onset of, viral infection, are provided.

18 Claims, 4 Drawing Sheets

```
                GUGCAGUUGGUUCGUCACAdTdT    SEQ ID NO:50
siRNA #1:       |||||||||||||||||||
            dTdTCACGUCAACCAAGCAGUGU        SEQ ID NO:51

                CUCAGCAGUGACAUAGACAdTdT    SEQ ID NO:52
siRNA #2:       |||||||||||||||||||
            dTdTGAGUCGUCACUGUAUCUGU        SEQ ID NO:53

                GUGACUCUCCAUCUUGUAGdTdT    SEQ ID NO:54
siRNA #3:       |||||||||||||||||||
            dTdTCACUGAGAGGUAGAACAUC        SEQ ID NO:55

                GCUGAACAUAAGGCCACAAdTdT    SEQ ID NO:56
siRNA #4:       |||||||||||||||||||
            dTdTCGACUUGUAUUCCGGUGUU        SEQ ID NO:57

                AGGCACGACUAGCAGAUAAdTdT    SEQ ID NO:58
siRNA #5:       |||||||||||||||||||
            dTdTUCCGUGCUGAUCGUCUAUU        SEQ ID NO:59

                GAUCUAUGAGUCCAUCGAAdTdT    SEQ ID NO:60
siRNA #6:       |||||||||||||||||||
            dTdTCUAGAUACUCAGGUAGCUU        SEQ ID NO:61

                CACAACAGGUUAACACACUdTdT    SEQ ID NO:62
siRNA #7:       |||||||||||||||||||
            dTdTGUGUUGUCCAAUUGUGUGA        SEQ ID NO:63

                AUAAGCGCAGCAGCUAUUAdTdT    SEQ ID NO:64
siRNA #8:       |||||||||||||||||||
            dTdTUAUUCGCGUCGUCGAUAAU        SEQ ID NO:65

                UAAGCGCAGCAGCUAUUAAdTdT    SEQ ID NO:66
siRNA #9:       |||||||||||||||||||
            dTdTAUUCGCGUCGUCGAUAAUU        SEQ ID NO:67

                GAACCUGUCAAGCGUGGUAdTdT    SEQ ID NO:68
siRNA #10:      |||||||||||||||||||
            dTdTCUUGGACAGUUCGCACCAU        SEQ ID NO:69

                GAGAGCCAGAUUCGAAUUGdTdT    SEQ ID NO:70
siRNA #11:      |||||||||||||||||||
            dTdTCUCUCGGUCUAAGCUUAAC        SEQ ID NO:71

                CUGUGAGGCUUGUAUGAAGdTdT    SEQ ID NO:72
siRNA #12:      |||||||||||||||||||
            dTdTGACACUCCGAACAUACUUC        SEQ ID NO:73
```

OTHER PUBLICATIONS

Akari, H. et al., "Suppression of HIV-1 replication in peripheral blood mononuclear cells by fasudil", *J. Med. Invest.*, 1998; 44:211-214.

Gower, T.L. et al., "RhoA Is Activated During Respiratory Syncytial Virus Infection", *Virology*,2001, 283:188-196.

Kadowaki, S. et al.,"Down-regulation of inducible nitric oxide synthase by lysophosphatidic acid in human respiratory epithelial cells", *Mol. Cell Biochem.*, 2003, 262:51-59.

Nishimura, Y. et al., "Small guanosine triphosphatase Rho/Rho-associated kinase as a novel regulator of Intracellular redistribution of lysosomes in invasive tumor cells", *Cell Tissue Res.*, 2000, 301:341-351.

Okada, H. et al., "Inhibition of HIV-1 Nef-induced apoptosis of uninfected human blood cells by serine/threonine protein kinase inhibitors, fasudil hydrochloride and M3", *FEBS Letters.*, 1998; 422:363-367.

Okada, H. et al., "Nef protein of HIV-1 induces apoptotic cytolysis of murine lymphoid cells independently of CD95 (Fas) and its suppression by serine/threonine protein kinase inhibitors", *FEBS Letters.*, 1997:61-64.

Riento et al., "Rocks: Multifunctional Kinases in Cell Behaviour", *Nature*, Jun. 2003, 4:446-456.

Sato, T. et al., "Inhibition of Human Immunodeficiency Virus Type 1 Replication by a Bioavailable Serine/Threonine Kinase Inhibitor, Fasudil Hydrochloride", *Aids Res. Hum. Retroviruses*, 1998: 14(4):293-298.

* cited by examiner

```
                 GUGCAGUUGGUUCGUCACAdTdT      SEQ ID NO:50
siRNA #1:        |||||||||||||||||||
             dTdTCACGUCAACCAAGCAGUGU          SEQ ID NO:51

                 CUCAGCAGUGACAUAGACAdTdT      SEQ ID NO:52
siRNA #2:        |||||||||||||||||||
             dTdTGAGUCGUCACUGUAUCUGU          SEQ ID NO:53

                 GUGACUCUCCAUCUUGUAGdTdT      SEQ ID NO:54
siRNA #3:        |||||||||||||||||||
             dTdTCACUGAGAGGUAGAACAUC          SEQ ID NO:55

                 GCUGAACAUAAGGCCACAAdTdT      SEQ ID NO:56
siRNA #4:        |||||||||||||||||||
             dTdTCGACUUGUAUUCCGGUGUU          SEQ ID NO:57

                 AGGCACGACUAGCAGAUAAdTdT      SEQ ID NO:58
siRNA #5:        |||||||||||||||||||
             dTdTUCCGUGCUGAUCGUCUAUU          SEQ ID NO:59

                 GAUCUAUGAGUCCAUCGAAdTdT      SEQ ID NO:60
siRNA #6:        |||||||||||||||||||
             dTdTCUAGAUACUCAGGUAGCUU          SEQ ID NO:61

                 CACAACAGGUUAACACACUdTdT      SEQ ID NO:62
siRNA #7:        |||||||||||||||||||
             dTdTGUGUUGUCCAAUUGUGUGA          SEQ ID NO:63

                 AUAAGCGCAGCAGCUAUUAdTdT      SEQ ID NO:64
siRNA #8:        |||||||||||||||||||
             dTdTUAUUCGCGUCGUCGAUAAU          SEQ ID NO:65

                 UAAGCGCAGCAGCUAUUAAdTdT      SEQ ID NO:66
siRNA #9:        |||||||||||||||||||
             dTdTAUUCGCGUCGUCGAUAAUU          SEQ ID NO:67

                 GAACCUGUCAAGCGUGGUAdTdT      SEQ ID NO:68
siRNA #10:       |||||||||||||||||||
             dTdTCUUGGACAGUUCGCACCAU          SEQ ID NO:69

                 GAGAGCCAGAUUCGAAUUGdTdT      SEQ ID NO:70
siRNA #11:       |||||||||||||||||||
             dTdTCUCUCGGUCUAAGCUUAAC          SEQ ID NO:71

                 CUGUGAGGCUUGUAUGAAGdTdT      SEQ ID NO:72
siRNA #12:       |||||||||||||||||||
             dTdTGACACUCCGAACAUACUUC          SEQ ID NO:73
```

Figure 1

```
                                                UUC
              5'- GUGCAGUUGGUUCGUCACA              A
shRNA1:           |||||||||||||||||||               A     SEQ ID NO:74
          3'-UUUUUGAGUCGUCACUGUAUCUGU              G
                                                AGA

                                                UUC
              5'- CUCAGCAGUGACAUAGACA              A
shRNA2:           |||||||||||||||||||               A     SEQ ID NO:75
          3'-UUUUUCACGUCAACCAAGCAGUGU              G
                                                AGA

                                                UUC
              5'- GUGACUCUCCAUCUUGUAG              A
shRNA3:           |||||||||||||||||||               A     SEQ ID NO:76
          3'-UUUUUCACUGAGAGGUAGAACAUC              G
                                                AGA

                                                UUC
              5'- GCUGAACAUAAGGCCACAA              A
shRNA4:           |||||||||||||||||||               A     SEQ ID NO:77
          3'-UUUUUCGACUUGUAUUCCGGUGUU              G
                                                AGA

                                                UUC
              5'- AGGCACGACUAGCAGAUAA              A
shRNA5:           |||||||||||||||||||               A     SEQ ID NO:78
          3'-UUUUUUCCGUGCUGAUCGUCUAUU              G
                                                AGA

                                                UUC
              5'- GAUCUAUGAGUCCAUCGAA              A
shRNA6:           |||||||||||||||||||               A     SEQ ID NO:79
          3'-UUUUUCUAGAUACUCAGGUAGCUU              G
                                                AGA
```

Figure 2a

```
                                      UUC
          5'- CACAACAGGUUAACACACU        A
shRNA7:       |||||||||||||||||||         A       SEQ ID NO:80
     3'-UUUUUGUGUUGUCCAAUUGUGUGA        G
                                      AGA

                                      UUC
          5'- AUAAGCGCAGCAGCUAUUA        A
shRNA8:       |||||||||||||||||||         A       SEQ ID NO:81
     3'-UUUUUUAUUCGCGUCGUCGAUAAU        G
                                      AGA

                                      UUC
          5'- UAAGCGCAGCAGCUAUUAA        A
shRNA9:       |||||||||||||||||||         A       SEQ ID NO:82
     3'-UUUUUAUUCGCGUCGUCGAUAAUU        G
                                      AGA

                                      UUC
          5'- GAACCUGUCAAGCGUGGUA        A
shRNA10:      |||||||||||||||||||         A       SEQ ID NO:83
     3'-UUUUUCUUGGACAGUUCGCACCAU        G
                                      AGA

                                      UUC
          5'- GAGAGCCAGAUUCGAAUUG        A
shRNA11:      |||||||||||||||||||         A       SEQ ID NO:84
     3'-UUUUUCUCUCGGUCUAAGCUUAAC        G
                                      AGA

                                      UUC
          5'- CUGUGAGGCUUGUAUGAAG        A
shRNA12:      |||||||||||||||||||         A       SEQ ID NO:85
     3'-UUUUUGACACUCCGAACAUACUUC        G
                                      AGA
```

Figure 2b

METHOD AND COMPOSITION FOR REDUCING EXPRESSION OF ROCK-II

RELATED APPLICATION

This patent application claims priority from U.S. Provisional Patent Application Ser. No. 60/496,950, filed Aug. 20, 2003, which is hereby incorporated by reference herein in its entirety.

SEQUENCE LISTING

The instant application was filed with a formal Sequence Listing submitted in paper and computer readable form on Aug. 20, 2004. An amended formal Sequence Listing submitted electronically as a text file has replaced the formal Sequence Listing. This text file, which was named "5044.01 2007-06-07 Amended SEQ-LIST JBO_ST25.txt", was created on Jun. 7, 2007, and is 26,024 bytes in size. Its contents are incorporated by reference herein in their entirety.

TECHNICAL FIELD OF THE INVENTION

The present invention relates generally to methods and pharmaceutical compositions for treating, and delaying the onset of, viral infection, and particularly to compositions and methods useful in the treatment of viral infections caused by viruses such as human immunodeficiency virus, hepatitis B virus, hepatitis C virus, herpes simplex virus type-1, herpes simplex virus type-2, herpes simplex virus type-4 (Epstein-Barr virus), influenza viruses, smallpox viruses, coronaviruses (i.e., SARS-associated), and West Nile virus.

TECHNICAL BACKGROUND OF THE INVENTION

Viral infection of humans is a major health problem, and viral infection of domesticated animals is a major economic concern. Combating viral infection has proven to be highly effective in some cases like smallpox where the disease was essentially eradicated with the advent of smallpox vaccination. Although smallpox was essentially eradicated by about 1980, there is considerable justified fear of the emergence of a new epidemic of smallpox since there are existing stockpiles of the virus and bioterrorism has moved beyond the realm of possibility to reality. Other viral infections have been much more difficult to fight. Human immunodeficiency virus (HIV), hepatitis B and C, herpes simplex viruses (HSVs) and influenza are just a few prominent members of a list of viruses that pose significant health threats worldwide. Additionally, emerging viral infections continue to threaten the world with human epidemics, as is illustrated by the recent outbreak of severe acute respiratory syndrome (SARS), which has now been associated with coronavirus infection. Treatments currently available for many viral infections are often associated with adverse side effects. In addition, antiviral therapeutics directed towards specific viral gene products frequently have the effect of driving the selection of viruses to become resistant to such therapeutics, and viral strains resistant to current methods of treatment are an increasing problem. Accordingly, there is a clear and ever-present need for new antiviral treatments.

SUMMARY OF THE INVENTION

The present invention generally relates to treating viral infections. In addition, the present invention also relates to treating and/or delaying the onset of symptoms caused by viral infections. Specifically, the inventors have unexpectedly discovered a new and useful antiviral activity provided by nucleic acid molecules that, when introduced into cells, either induce the degradation of RNA transcripts encoding Rho-associated, coiled-coil containing protein kinase 2 (ROCK-II), or otherwise specifically reduce the expression of ROCK-II, such that the concentration of ROCK-II protein is reduced within the cell.

Thus, in a first aspect, the present invention provides nucleic acid molecules which, when introduced into cells, induce the degradation of RNA transcripts encoding ROCK-II, or otherwise specifically reduce the expression of ROCK-II, and result in a reduction of ROCK-II protein concentrations within the cell. Such nucleic acid molecules can be RNA molecules that can act by inducing RNA interference (RNAi). For example, the RNA molecules can be small interfering RNAs (siRNAs) or small hairpin RNAs (shRNAs), which can be processed into siRNAs within cells. Alternatively, such nucleic acid molecules can act directly to cleave RNA transcripts encoding ROCK-II. Such enzymatic nucleic acid molecules may be RNA molecules, DNA molecules, or analogs or modified forms thereof. For example, the nucleic acid molecules can be ribozymes of any appropriate class, such as hammerhead ribozymes, designed to specifically target and cleave RNA transcripts encoding ROCK-II. Alternatively, the nucleic acids of the present invention can also be antisense oligonucleotides that activate cleavage of transcripts encoding ROCK-II by cellular nucleases, especially RNase H—the nuclease that recognizes RNA/DNA heteroduplexes and specifically cleaves the RNA. Such antisense oligonucleotides can be DNA, or any modified form or analog thereof, provided the analog or modified form is still capable of activating cleavage of ROCK-II transcripts by RNase H. Finally, the nucleic acids of the present invention can also be antisense oligonucleotides that reduce the expression of ROCK-II by specifically blocking, or otherwise reducing the translation of RNA transcripts encoding ROCK-II, thereby specifically resulting in a reduction of the cellular levels of ROCK-II. Such antisense oligonucleotides can be DNA, or any modified form or analog thereof, provided the analog or modified form is still capable of specifically causing a reduction in cellular levels of ROCK-II.

In another aspect, the present invention provides expression cassettes that direct the expression of nucleic acid molecules that induce the degradation of RNA transcripts encoding ROCK-II, or otherwise result in a specific reduction in cellular levels of ROCK-II. Such expression cassettes can be incorporated into the products of the Polymerase Chain Reaction (PCR), circular plasmids, or viral vectors.

In yet another aspect, the present invention provides mammalian cells comprising nucleic acid molecules that induce the degradation of RNA transcripts encoding ROCK-II, or otherwise result in a specific reduction in cellular levels of ROCK-II. In one embodiment, the mammalian cells are human cells.

In still another aspect, the present invention provides a method of treating viral infection by administering a nucleic acid molecule that ultimately induces the degradation of RNA transcripts encoding ROCK-II, or otherwise results in a specific reduction in cellular levels of ROCK-II. In one embodiment of this aspect the nucleic acid is an RNA molecule, whose synthesis is directed by an expression cassette of the present invention. In another embodiment, the nucleic acid is an RNA or DNA molecule that is introduced directly to cells by any acceptable means.

In another aspect, the present invention provides a method for treating a cell infected with a virus comprising the step of contacting the infected cell with a nucleic acid molecule that induces the degradation of RNA transcripts encoding ROCK-II, or otherwise results in a specific reduction in cellular levels of ROCK-II.

In yet another aspect, the present invention provides methods for treating viral infection by administering to a patient, human or otherwise, in need of such treatment a pharmaceutical composition or medicament having a therapeutically effective amount of a nucleic acid molecule that induces the degradation of RNA transcripts encoding ROCK-II, or otherwise results in a specific reduction in cellular levels of ROCK-II. In a particular embodiment of this aspect of the invention, the method and composition are used to treat viral infection in a human in need of such treatment.

In still another aspect, methods for inhibiting the entry, egress or budding of viruses into or out of cells are also provided by administering to a patient in need of such treatment a pharmaceutical composition or medicament having an amount of a compound of a nucleic acid molecule that induces the degradation of RNA transcripts encoding ROCK-II, or otherwise results in a specific reduction in cellular levels of ROCK-II, and is sufficient to inhibit the entry, egress or budding of a virus into or out of human or animal cells. In one particular aspect of this embodiment of the invention, the method of inhibiting viral entry, egress or budding involves treating humans or other animals infected with a virus, and in need of such treatment.

In another aspect, the present invention relates to methods for treating viral infection, which comprise the steps of (1) identifying an animal diagnosed with a viral infection; and (2) administering to the animal a pharmaceutical composition or medicament having a therapeutically effective amount of a nucleic acid molecule that induces the degradation of RNA transcripts encoding ROCK-II, or otherwise results in a specific reduction in cellular levels of ROCK-II. In particular embodiments of this aspect of the invention, the animals to be treated are humans infected with a virus.

In yet another aspect, the present invention further provides methods for delaying the onset of symptoms of viral infection comprising administering a pharmaceutical composition or medicament having a prophylactically effective amount of a nucleic acid molecule that induces the degradation of RNA transcripts encoding ROCK-II, or otherwise results in a specific reduction in cellular levels of ROCK-II, to an animal having a viral infection, or at risk of infection by a virus, or at risk of developing symptoms of viral infection. In particular embodiment of this aspect of the invention, the method of inhibiting or delaying the onset of viral infection symptoms involves treating humans infected with a virus.

In one embodiment of this aspect, a method is provided for treating a person who is a carrier of any of the HIV family of retroviruses, i.e., infected with HIV, but has not developed AIDS (which is defined by more serious AIDS-defining illnesses and/or a decline in the circulating CD4 cell count to below a level that is compatible with effective immune function). The method includes identifying such an individual in need of treatment and administering to the individual a pharmaceutical composition or medicament having a prophylactically effective amount of a compound of a nucleic acid molecule that induces the degradation of RNA transcripts encoding ROCK-II, or otherwise results in a specific reduction in cellular levels of ROCK-II. Thus, the method can be used in treating acute primary HIV infection syndrome (which can be asymptomatic or associated with an influenza-like illness with fevers, malaise, diarrhea and neurological symptoms such as headache) or asymptomatic infection (which is the long latent period with a gradual decline in the number of circulating CD4 T-cells).

In another embodiment, a method is provided for treating a person who is either actively infected with Hepatitis B virus (HBV), Hepatitis C virus (HCV), or who is a carrier of these viruses that has either not developed symptoms of the viral infection (which is defined by liver damage) or has experienced diminution of such symptoms, or who has recently been exposed to such viruses. The method includes identifying such an individual in need of treatment and administering to the individual a pharmaceutical composition or medicament having a therapeutically effective, or prophylactically effective, amount of a nucleic acid molecule that induces the degradation of RNA transcripts encoding ROCK-II, or otherwise results in a specific reduction in cellular levels of ROCK-II.

In still another embodiment, a method is provided for treating a person who is either actively infected with herpes simplex virus type-1, type-2, or type-4 (also known as Epstein-Barr virus), or who is a carrier of these viruses who has either not developed symptoms of the viral infection or has experienced diminution of such symptoms, or who has recently been exposed to such viruses. The method includes identifying such an individual in need of treatment and administering to the individual a pharmaceutical composition or medicament having a therapeutically effective, or prophylactically effective, amount of a nucleic acid molecule that induces the degradation of RNA transcripts encoding ROCK-II, or otherwise results in a specific reduction in cellular levels of ROCK-II.

In yet another embodiment, a method is provided for treating an individual who is either actively infected with influenza virus type-A, type-B, or type-C, or who is a carrier of these viruses who has either not developed symptoms of the viral infection, or has experienced diminution of such symptoms, or who has recently been exposed to such viruses. The method includes identifying such an individual in need of treatment and administering to the individual a pharmaceutical composition or medicament having a therapeutically effective, or prophylactically effective, amount of a nucleic acid molecule that induces the degradation of RNA transcripts encoding ROCK-II, or otherwise results in a specific reduction in cellular levels of ROCK-II.

In still another embodiment, a method is provided for treating a person who is either actively infected with any of the poxvirus family of viruses, i.e., the smallpox virus, or who is a carrier of these viruses who has either not developed symptoms of the viral infection (which is defined by more serious smallpox-defining illnesses) or has experienced diminution of such symptoms, or who has recently been exposed to such viruses. The method includes identifying such an individual in need of treatment and administering to the individual a pharmaceutical composition or medicament having a therapeutically effective, or a prophylactically effective, amount of a nucleic acid molecule that induces the degradation of RNA transcripts encoding ROCK-II, or otherwise results in a specific reduction in cellular levels of ROCK-II.

In another embodiment, a method is provided for treating a person who is either actively infected with any of the coronavirus family of viruses, i.e., infected with a SARS-associated coronavirus, or who is a carrier of such viruses who has either not developed symptoms of the viral infection (which is defined by more serious SARS-defining illnesses) or who has experienced diminution of such symptoms, or who has recently been exposed to such viruses. The method includes identifying such an individual in need of treatment and administering to the individual a pharmaceutical composition or medicament having a prophylactically effective amount of a compound of a nucleic acid molecule that induces the degradation of RNA transcripts encoding ROCK-II, or otherwise results in a specific reduction in cellular levels of ROCK-II.

In yet another embodiment, a method is provided for treating a person or an animal that is either actively infected with West Nile virus, or is a carrier of the West Nile virus and has either not developed symptoms of the viral infection, or has experienced diminution of such symptoms, or has recently been exposed to West Nile virus. The method includes identifying such an individual in need of treatment and administering to the individual a pharmaceutical composition or medicament having a prophylactically effective amount of a nucleic acid molecule that induces the degradation of RNA transcripts encoding ROCK-II, or otherwise results in a specific reduction in cellular levels of ROCK-II.

The present invention provides compositions for use in treating or delaying the onset of symptoms of the aforementioned viral infections. These compositions, which generally include a nucleic acid molecule that induces the degradation of RNA transcripts encoding ROCK-II, or otherwise results in a specific reduction in cellular levels of ROCK-II, can be provided as a pharmaceutical composition with one or more salts, carriers, or excipients, and with agents to improve uptake of the nucleic acid molecules by cells.

The present invention also provides pharmaceutical compositions or medicaments for the combination therapy of viral infections. The compositions comprise a therapeutically effective amount of a first compound containing a nucleic acid molecule that induces the degradation of RNA transcripts encoding ROCK-II, or otherwise results in a specific reduction in cellular levels of ROCK-II, and a therapeutically effective amount of a second antiviral compound, which is different from the first compound. Examples of second antiviral compounds include, but are not limited to, protease inhibitors, nucleoside reverse transcriptase inhibitors, non-nucleoside reverse transcriptase inhibitors, integrase inhibitors, fusion inhibitors, immunomodulators, and vaccines. In one embodiment, the second antiviral compound is an inhibitor of ROCK-II.

The foregoing and other advantages and features of the invention, and the manner in which they are accomplished, will become more readily apparent upon consideration of the following detailed description of the invention taken in conjunction with the accompanying examples, which illustrate preferred and exemplary embodiments.

DESCRIPTION OF THE FIGURES

FIG. 1 depicts exemplary siRNA molecules corresponding to 12 different target sequences in the human ROCK-II (messenger RNA) mRNA coding sequence, and capable of inducing the degradation of RNA transcripts encoding ROCK-II;

FIG. 2 depicts exemplary shRNA molecules corresponding to the same 12 target sequences in ROCK-II mRNA as the siRNAs of FIG. 1;

DETAILED DESCRIPTION OF THE INVENTION

Figure 3:
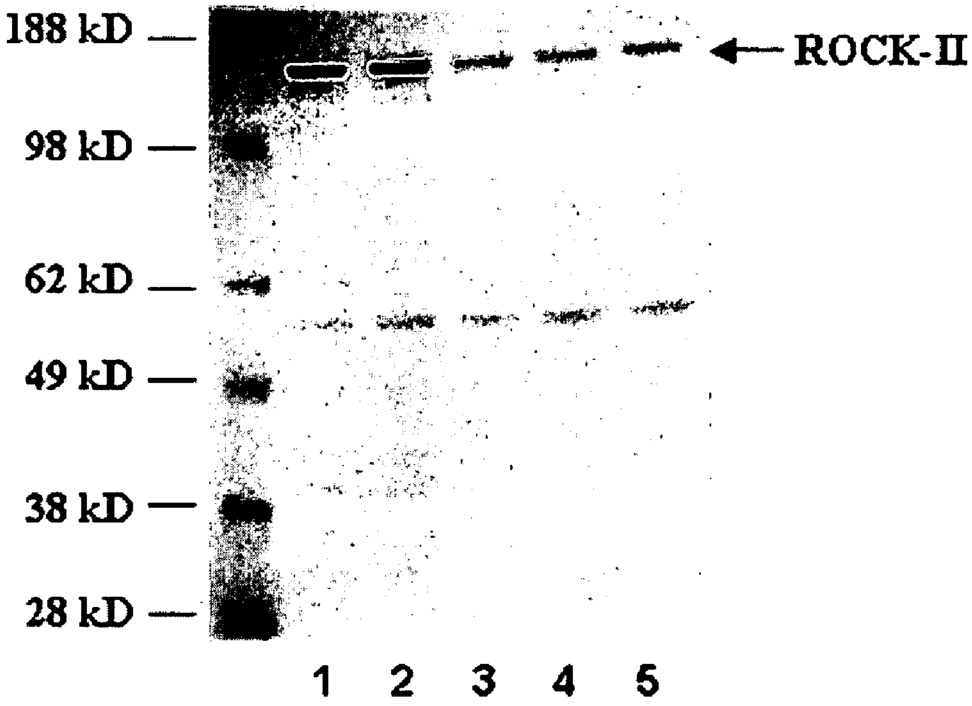
FIG. 3 shows the results of treatment of human 293T cells by siRNAs #1, #3 and #10, on the concentration of ROCK-II protein, as determined by Western Blotting.

The present invention provides methods and compositions for the treatment and prevention (or delaying the onset) of viral infection and particularly symptoms caused by viral infection. Specifically, nucleic acid molecules that induce the degradation of RNA transcripts encoding Rho-associated, coiled-coil containing protein kinase 2 (ROCK-II), or otherwise result in reductions in the concentration of ROCK-II protein within cells, are used in the methods and compositions. Importantly, ROCK-II is a host cell protein, the activity of which has been discovered by the inventors to be required by viruses during the course of their infective cycles. In general, the invention provides nucleic acid molecules that either induce the degradation of RNA transcripts encoding ROCK-II, or otherwise lead to a decrease in cellular concentrations of ROCK-II protein. Such nucleic acid molecules have associated therapeutic benefits, particularly in the inhibition of viral infections.

As used herein, the phrase "nucleic acids that induce degradation of RNA transcripts encoding ROCK-II" means any nucleic acid molecule, modified nucleic acid molecule, or nucleic acid molecule analog that results in the reduction of concentrations of mRNA or pre-mRNA encoding the ROCK-II protein inside a cell. Such nucleic acid molecules can be RNAs that act by inducing RNA interference (RNAi)—the double-stranded RNA-directed degradation of endogenous transcripts of corresponding sequence. Alternatively, such nucleic acid molecules can be enzymatic nucleic acids, either RNA molecules, DNA molecules, or derivatives or analogs thereof, that directly cleave RNA transcripts encoding ROCK-II. Additionally, such nucleic acid molecules can also be antisense oligonucleotides that specifically hybridize with mRNA or pre-mRNA encoding the ROCK-II and promote the cleavage and degradation of these transcripts by cellular endonucleases, such as ribonuclease-H (RNase-H).

The phrase "nucleic acids that otherwise result in a decrease in cellular levels of ROCK-II," as used herein, generally refers to nucleic acid molecules capable of hybridizing to mRNA or pre-mRNA encoding the ROCK-II protein, and blocking the expression of the ROCK-II protein encoded by that transcript.

As used herein "RNA transcripts encoding ROCK-II" means RNA transcribed from the ROCK-II gene, including unspliced or partially spliced pre-mRNAs, and spliced or mature mRNAs (Such as provided by SEQ ID NO:1). Such transcripts encode the ROCK-II protein, and therefore contain ROCK-II coding sequence (provided as SEQ ID NO:2), as well as other sequences such as 5' and 3' untranslated regions, poly-adenosine tails, and, in the case of pre-mRNAs, introns. It should be understood that, "RNA transcripts encoding ROCK-II" also includes any naturally occurring polymorphic variants of RNA transcripts encoding ROCK-II.

As used herein "ROCK-II" or "ROCK-II protein" refers to Rho-associated, coiled-coil containing protein kinase 2. ROCK-II (also known as ROCK2) is a serine/threonine kinase that regulates, among other things, cytokinesis, smooth muscle contraction, the formation of actin stress fibers and focal adhesions, and the activation of the c-fos serum response element (see review by Riento and Ridley, *Nat. Rev. Mol. Cell Biol.* 4:446-456 (2003)). ROCK-II, is an isozyme of ROCK-I, and like ROCK-I, is a target for the small GTPase Rho. The human ROCK-II gene resides at chromosomal location 2p24, and directs the transcription of ROCK-II mRNA, the sequence of which is provided by SEQ ID NO:1, and by GenBank RefSeq NM_004850.2.

As used herein "nucleic acid molecules that induce the degradation of RNA transcripts encoding ROCK-II" are understood to include RNA molecules, DNA molecules, and analogs and modified forms thereof. The "nucleic acid molecules that induce the degradation of RNA transcripts encoding ROCK-II" of the present invention are provided such that, when introduced into cells, they result in the reduction of RNA transcripts encoding ROCK-II by at least 20%, as measured by quantitative RT-PCR, and/or result in the reduction of cellular ROCK-II protein levels at least a 20%, as measured by quantitative Western Blot.

Similarly, "nucleic acids that otherwise result in a reduction in cellular ROCK-II levels" are understood to include RNA molecules, DNA molecules, and analogs and modified forms thereof. The "nucleic acids that otherwise result in a reduction in cellular ROCK-II levels" of the present invention are provided such that, when introduced into cells, they result in the reduction of cellular ROCK-II protein levels at least a 20%, as measured by quantitative Western Blot.

Confirmation that a nucleic acid molecule is a "nucleic molecules that induces degradation of RNA transcripts encoding ROCK-II" can be obtained by demonstrating a quantitative reduction in transcripts encoding ROCK-II, or a reduction in ROCK-II protein itself, using any method known in the art. However, a preferred method for demonstrating a quantitative reduction in transcripts encoding ROCK-II is "Real-Time Quantitative RT-PCR," as described in a publication by Winer et al. (*Anal. Biochem.* 270:41-49 (1999)), which is incorporated herein by reference in its entirety. Similarly, a preferred method for demonstrating a quantitative reduction in ROCK-II protein is quantitative Western Blot analysis, as described in a publication by Gingrich et al., (*BioTechniques* 29:636-642 (2000)), which is incorporated herein by reference in its entirety. Primary antibody specifically immunoreactive to ROCK-II, which can be used for quantitative Western Blot analysis of ROCK-II, is commercially available (e.g., BD Biosciences/Pharmingen (San Diego, Calif., USA)). This same antibody can also be used for enzyme-linked immunosorbent assays (ELISAs) designed to quantitate ROCK-II protein.

Importantly, in order to determine the amount of reduction of RNA transcripts encoding ROCK-II, and/or the amount of cellular ROCK-II protein levels, one must first conduct a control experiment(s) to determine transcript and/or protein levels prior to, or in the absence of, treatment by the nucleic acid molecules of the present invention. Such a control experiment allows for the establishment of "baseline" levels, against which the nucleic acid induced reduction of transcript and/or protein levels can be measured.

Furthermore, methods to quantitate mRNA or protein expression levels generally require that the results obtained be normalized for differences in the amount of total RNA or total protein in the sample to be quantitated. Generally, normalization is achieved by quantitating an internal standard such as the products of a ubiquitously expressed "housekeeping" gene. For example, normalization of quantitative RT-PCR assays can be achieved by simultaneously quantitating mRNA encoding glyceraldehyde-3-phosphate dehydrogenase (GAPDH), which is expressed at generally invariant levels in different cell types under different treatment conditions (Winer et al., *Anal. Biochem.* 270:41-49 (1999)). Differences in the levels of GAPDH mRNA determined are representative of different amounts of input mRNA templates between reactions, and can be used as an internal standard by which to adjust levels of the quantitated transcript, to adjust for such differences in input mRNA templates. Similarly, the levels of GAPDH protein can be used to normalize for differences in the amounts of input total protein during protein quantitation assays.

Nucleic Acid Molecules of the Present Invention:

In accordance with the present invention, the nucleic acid molecules that induce the degradation of transcripts encoding ROCK-II are capable of hybridizing to such transcripts under physiological conditions. In certain embodiments, such nucleic acid molecules are members of any class of RNAs, DNAs or analogs or modified forms thereof, having this effect. For example, in some embodiments, such nucleic acid molecules can be small interfering RNAs (siRNAs), or small hairpin RNAs (shRNAs) that can be processed into siRNAs within cells, that induce RNAi-mediated degradation of transcripts encoding ROCK-II. In other embodiments, such nucleic acid molecules can be enzymatic nucleic acids, such as ribozymes, or DNAzymes, that enzymatically cleave transcripts encoding ROCK-II. In still other embodiments, such nucleic acid molecules can be antisense oligonucleotides that hybridize with mRNA or pre-mRNA encoding the ROCK-II and promote the cleavage and degradation of these transcripts by RNase-H.

Also in accordance with the present invention, the nucleic acid molecules that otherwise result in the reduction of cellular ROCK-II levels are also capable of hybridizing to such transcripts under physiological conditions. However, in embodiments employing these nucleic acids, such nucleic acids need not induce the degradation of transcripts encoding ROCK-II. Instead, such nucleic acid molecules can be antisense oligonucleotides that hybridize with mRNA or pre-mRNA encoding the ROCK-II and interfere with the expression of the encoded ROCK-II. This interference of expression of ROCK-II can involve any mechanism, generally including, but not limited to, blocking translation, blocking RNA processing reactions, and blocking proper localization of the ROCK-II encoding transcripts.

RNA Interference Inducing Nucleic Acids:

The process of siRNA-directed degradation of an RNA transcript of corresponding sequence is referred to as RNA interference, RNAi, or, more generally, the "knocking down" or "silencing" of the expression of a particular gene. Practically, siRNA-directed or induced RNAi leads to the degradation of the targeted transcript, and a corresponding decrease in cellular levels of the gene product that the transcript encodes.

As is known in the art, siRNAs are short intermolecular duplexes, generally composed of two distinct (sense and antisense) strands of RNA, each of approximately 21 nucleotides, which are partly complementary and hybridize to form approximately 19 base-pairs, with single-stranded 3' overhangs of 1-3, but preferably 2, nucleotides. The base-paired region of siRNAs generally corresponds substantially, preferably exactly, to a "target sequence" and its complement, in the RNA transcript to be targeted for degradation by the RNAi process and cellular machinery.

The specific features of siRNAs required for inducing the efficient degradation or silencing of corresponding RNA transcripts have been systematically investigated, as have the features of the target sequence within the targeted transcript. The results of such experiments have been published and general "rules" have been established for the design of effective siRNA molecules (see, e.g., Tuschl et al., *Genes & Dev.* 13:3191-3197 (1999) and Elbashir et al., *EMBO J.* 20:6877-6888 (2001), among other sources).

Generally, the most effective silencing is obtained with siRNA duplexes composed of 21 nucleotide sense and antisense strands that are paired in a manner to produce 2 nucleotide 3' overhangs. The sequence of the overhangs makes only a small contribution to the overall specificity of target recognition, but the identity of the nucleotide adjacent to the paired region can have an effect. In addition, the 3' overhangs can be composed either ribonucleotides or 2'-deoxyribonucleotides, with no apparent differences in efficacy, however siRNAs with 2'-deoxyribonucleotide overhangs may be more resistant to certain cellular nucleases.

Target sequences in targeted RNA transcripts preferably have the sequence AA(19N)UU, where N=any nucleotide, but can be any contiguous 19 nucleotides. Importantly, target sequences must be chosen from the sequences present in mature mRNAs, but can reside in either coding or non-coding regions. Preferably the target sequence chosen is readily "accessible," to the siRNA, that is, not involved in a stable base-paired structure within the mature transcript, and not specifically bound by an RNA-binding protein. RNA folding algorithms, such as the "Sfold" algorithm available through an Sfold web-server developed by Ding, Chan and Lawrence (described in *Nucleic Acids Res.* 32 (Web Server issue):W135-41 (2004)), which is incorporated herein by reference in its entirety) can be useful for picking target sequences that have a greater likelihood of being accessible, and therefore efficiently targeted by a corresponding siRNA, resulting in the efficient degradation of the targeted transcript and significant reduction in the cellular concentration of its encoded gene product.

The individual single-stranded RNAs comprising siRNAs can either be synthesized outside of cells (exogenously), or within cells (endogenously). The two complementary single strands must then anneal to form an RNA duplex—the siRNA. The annealing step can also occur exogenously or endogenously. Exogenously synthesized single-stranded RNAs can be synthesized either chemically, for example using phosphoramidite chemistry, or can be synthesized enzymatically, using an RNA polymerase and a DNA template containing an appropriate promoter sequence just upstream of the template sequence. Exogenously synthesized single-stranded RNAs must generally be purified to some degree, before they can be annealed to form siRNA duplexes. Endogenously synthesized single-stranded RNAs are synthesized by cellular RNA polymerases using a DNA template that contains an appropriate promoter sequence just 5' (upstream) of the template sequence.

Small hairpin RNAs, or shRNAs, are single-stranded RNAs with regions of self-complementarity that can pair with one another, allowing the single strand to fold into an intramolecular duplex with a stem-loop type structure. Although the unpaired loop region can theoretically be any size, it is advantageous for the loop to be small enough to readily allow the self-complementary sequences within the same single-stranded RNA to find each other and form base pairs across their complementary region. Preferred loop sizes are from 3 to 9 nucleotides, and larger, with loops of 6-9 nucleotides being most preferred. Generally the sequence of the loop is not important, however, it should not consist of palindromic sequence, nor should it be related to sequences adjacent to the target sequence, which is represented by one of the paired complementary regions, and to which the shRNA ultimately targets. Within the cell the loop of an shRNAs is apparently cleaved and an intermolecular duplex, not unlike an siRNA, is formed. The stem region of the shRNA should generally contain approximately 19 base pairs, and generally the 3' end of the shRNA extending beyond the paired region is composed of multiple uracil residues. The base-paired regions of shRNAs generally correspond substantially, preferably exactly, to a "target sequence" and its complement in the RNA transcript to be targeted for degradation, just as the base-paired region in an siRNAs does.

Like the individual strands of siRNAs, shRNAs can be can be synthesized either endogenously, or exogenously. Endogenously synthesized shRNAs are generally synthesized by cellular RNA polymerases using a DNA template that contains an appropriate promoter sequence just 5' ("upstream") of the template sequence. Exogenously synthesized shRNAs can be synthesized either chemically, for example using phosphoramidite chemistry, or can be synthesized enzymatically, using an RNA polymerase and a DNA template containing an appropriate promoter sequence just upstream of the template sequence. Exogenously synthesized shRNAs must generally be purified to some degree, before they can be used to induce RNAi and the degradation of an RNA transcript of corresponding sequence.

The DNA template containing a promoter and the template sequence used to direct the enzymatic synthesis of siRNAs or shRNAs, and optionally a transcription termination sequence, is commonly referred to as an expression cassette. Such expression cassettes can be incorporated into vector DNAs, such as circular plasmids, or viral vectors of various types that can be packaged into modified viral particles to facilitate viral transduction of the cassette into cells. Alternatively, expression cassettes can be readily designed and produced by incorporating them into the linear products of a polymerase chain reaction (PCR), which can transfected into cells to direct the expression of siRNAs or shRNAs in vivo (e.g., Castanotto et al., *RNA* 8:1454-1460 (2002)). Such PCR products containing expression cassettes can be readily produced in large numbers by the PCR, and different template sequences can be incorporated into the cassettes.

Several U.S. and P.C.T. Patent Application Publications teach preferred methods for designing, synthesizing, purifying, and delivering siRNAs and shRNAs into cells. In particular, U.S. Patent Application Publication US 2003/0148519, which is incorporated herein by reference in its entirety, provides compositions and methods for intracellular expression and delivery of siRNAs and shRNAs in mammalian cells; and U.S. Patent Application Publication US 2002/0132788, which is incorporated by reference herein in its entirety, provides a process for delivering siRNAs into cells in vivo for the purpose of inhibiting gene expression in those cells.

Enzymatic Nucleic Acids:

Alternatively, the nucleic acids of the present invention used to induce the degradation of RNA transcripts encoding ROCK-II can act directly to cleave these transcripts, without the involvement of cellular RNAi machinery. Such nucleic acids, which are referred to here as "enzymatic nucleic acids," must be competent to catalytically cleave ROCK-II encoding RNA transcripts, and must be specifically directed to preferentially cleave ROCK-II encoding transcripts.

The term "enzymatic nucleic acid molecules" or "enzymatic nucleic acids" as used herein refers to a nucleic acid molecule that has complementarity to a specified gene target in a substrate binding region, and also has an enzymatic activity which is active to specifically cleave the target RNA. That is, the enzymatic nucleic acid molecule is able to intermolecularly cleave target RNA and thereby result in the degradation of the target RNA molecule. The complementary regions of the enzymatic nucleic acid allow sufficient hybridization of the enzymatic nucleic acid molecule to the target RNA and thus permit preferential cleavage of the target RNA. One hundred percent complementarity is preferred between the target RNA and the substrate binding region of the enzymatic nucleic acid, but complementarity as low as 50-75% can also be useful in this invention (see for example Werner and Uhlenbeck, *Nucleic Acids Res.* 23:2092-2096 (1995); Hammann et al., *Antisense and*

*Nucleic Acid Drug Dev.,* 9:25-31 (1999)). The nucleic acids can be modified at the base, sugar, and/or phosphate groups to enhance stability within host cells, or improve catalytic activity. The phrase "enzymatic nucleic acid" is understood to include specific examples of catalytic nucleic acids including "ribozymes," "catalytic RNAs," "enzymatic RNAs," "catalytic DNAs," "aptazymes" or "aptamer-binding ribozymes," "regulatable ribozymes," "catalytic oligonucleotides," "nucleozymes," "DNAzymes," "RNA enzymes," "endoribonucleases," "endonucleases," "minizymes," "leadzymes," "oligozymes" or "DNA enzymes." All of these terms describe specific types of nucleic acid molecules with catalytic activity. The specific enzymatic nucleic acid molecules described in the instant application are not intended to limit the invention to that type of enzymatic nucleic acid molecule alone, and those skilled in the art will recognize that what is important for an enzymatic nucleic acid molecule of the present invention is that it has a specific substrate binding site which is complementary to one or more of the target regions within transcripts encoding ROCK-II, and that it have nucleotide sequences within or surrounding that substrate binding site that impart a nucleic acid cleaving activity to the enzymatic nucleic acid molecule (see e.g., Cech et al., U.S. Pat. No. 4,987,071; Cech et al., *JAMA* 260:3030 (1988)).

Several varieties of enzymatic nucleic acids are known presently, which can catalyze, for example, the hydrolysis of RNA phosphodiester bonds in trans (and thus can cleave other RNA molecules) under physiological conditions. In general, enzymatic nucleic acids with RNA endonuclease activity act by first binding to a target RNA. Such binding occurs through the target-binding portion of the enzymatic nucleic acid, which is held in close proximity to an enzymatic portion of the molecule, which acts to cleave the target RNA. Thus, the enzymatic nucleic acid, for example, first recognizes and then binds a target RNA through complementary base pairing, and once bound to the correct site, acts to enzymatically cleave the target RNA. Strategic cleavage of such a target RNA will lead to the destabilization and degradation of the target RNA, or otherwise destroy its ability to direct synthesis of an encoded protein. After an enzymatic nucleic acid has bound and cleaved its RNA target, the cleaved target RNA is released from the enzymatic nucleic acid, so that the enzymatic nucleic acid is freed to search for, and cleave another target, thereby repeatedly binding and cleaving multiple target RNAs. In addition, the enzymatic nucleic acid is a highly specific inhibitor of gene expression, with the specificity of inhibition depending not only on the base-pairing mechanism of binding to the target RNA, but also on the mechanism of target RNA cleavage. Single mismatches, or base-substitutions, near the site of cleavage can completely eliminate catalytic activity of an enzymatic nucleic acid molecule.

As with siRNAs and shRNAs, the choice of an appropriate target sequence is important for the function of ROCK-II-directed enzymatic nucleic acids, and the accessibility of a target sequence is an important factor for the efficient cleavage of a specific RNA transcript by a corresponding ribozyme. Preferably the target sequence chosen is readily "accessible," to the enzymatic nucleic acid, that is, not involved in a stable base-paired structure within the mature transcript, and not specifically bound by an RNA-binding protein. RNA folding algorithms, such as the "Sfold" algorithm available through an Sfold web-server developed by Ding, Chan and Lawrence (described in *Nucleic Acids Res.* 32 (Web Server issue):W135-41 (2004)), which is incorporated herein by reference in its entirety) can be useful for picking target sequences that have a greater likelihood of being accessible, and therefore efficiently targeted by a corresponding enzymatic nucleic acid, resulting in the efficient degradation of the targeted transcript and significant reduction in the cellular concentration of its encoded gene product.

Antisense and RNase H Activating Nucleic Acids:

The terms "antisense nucleic acid" or "antisense oligonucleotide," as used herein, refer to a non-enzymatic nucleic acid molecule that specifically hybridizes to RNA transcripts bearing a complementary nucleotide sequence. Typically, antisense molecules are complementary to a target sequence along a single contiguous sequence of the sense molecule. However, in certain embodiments, an antisense molecule can bind to substrate such that the substrate molecule forms a loop, and/or an antisense molecule can bind such that the antisense molecule itself forms a loop. Thus, the antisense molecule can be complementary to two (or even more) non-contiguous substrate sequences, or two (or even more) non-contiguous sequence portions of an antisense molecule can be complementary to a target sequence or both. For a review of current antisense strategies, see Schmajuk et al., *J. Biol. Chem.,* 274, 21783-21789 (1999), Delihas et al., *Nature,* 15, 751-753 (1997), Stein et al., *Antisense Nuclei Acid Drug Dev.,* 7, 151 (1997), Crooke, *Methods Enzymol.,* 313, 3-45 (2000); Crooke, Biotech. Genet. Eng. Rev., 15, 121-157 (1998), Crooke, *Ad. Pharmacol.* 40, 1-49 (1997).

The present invention preferably provides antisense DNA that can be used to target nucleic acids by means of DNA-RNA interactions, thereby activating RNase H, which digests the target RNA in the duplex. The antisense oligonucleotides can comprise one or more RNase H activating regions, which are capable of activating RNAse H cleavage of the target RNA. Antisense DNA can be synthesized chemically or expressed via the use of a single stranded DNA expression vector or equivalent thereof.

Alternatively, the present invention preferably provides antisense nucleic acids (either DNA, RNA, or mimetics or derivatives thereof) that can be used to target nucleic acids by means of hybridization, and, once hybridized, the antisense nucleic acids interfere with the expression of the encoded protein. In these embodiments, the antisense nucleic acids interfere with expression of the encoded protein, either by blocking translation, blocking RNA processing reactions, or blocking proper localization of the target RNA.

Isolated Mammalian Cells:

The present invention further provides an isolated mammalian cell including the nucleic acid molecules that induce the degradation of RNA transcripts encoding ROCK-II or otherwise specifically interfere with the expression of ROCK-II. Preferably the mammalian cell is a human cell. Also, as mentioned above, the nucleic acid molecules that induce the degradation of RNA transcripts encoding ROCK-II, and are to be included within the isolated cell, can either be synthesized inside of the cell (endogenously), or synthesized outside of the cell (exogenously) and subsequently delivered into the cell. Methods for the intracellular expression of siRNAs in mammalian cells are provided in U.S. Patent Application Publication 2003/0148519, which is incorporated herein by reference in its entirety.

Pharmaceutical Compositions and Formulations:

The present invention also includes pharmaceutical compositions comprising nucleic acid molecules that induce the degradation of RNA transcripts encoding ROCK-II, or otherwise result in the specific reduction of cellular levels of ROCK-II, and physiologically acceptable carriers. The pharmaceutical composition of the present invention may contain either a therapeutically effective amount of the nucleic acid molecule that induces the degradation of RNA transcripts encoding ROCK-II, or otherwise results in a specific reduction in cellular levels of ROCK-II, for patients infected with a virus, or a prophylactically effective amount of the nucleic acid molecule for patients who are exposed to the virus, or are otherwise at risk of developing an infection by the virus. The pharmaceutical composition of the present invention may also include any variety of antiviral compounds, besides the nucleic acids of the present invention, for use in "combination therapy" for individuals infected with viruses.

Compounds containing nucleic acid molecules that induce the degradation of RNA transcripts encoding ROCK-II, or otherwise specifically reduce the cellular concentration of ROCK-II, are particularly effective in inhibiting viral infection of, and/or viral entry into, or viral egress from, host cells. While not wishing to be bound by any theory or hypothesis, it is believed that viruses utilize the host protein ROCK-II to carry out specific tasks during the viruses' life cycles. Inhibition of ROCK-II activity, by e.g. diminution of cellular concentrations of ROCK-II, results in either the inhibition of the entry, the inhibition of egress (i.e., release of viruses from host cells), or the inhibition of budding (i.e., viral particles pinching off host cell intracellular or plasma membranes) of viruses into and out of host cells, or some combination thereof. Since the nucleic acids of the present invention target the host cell protein ROCK-II, rather than viral proteins, such nucleic acids are believed to be significantly less susceptible to the loss of efficacy caused by the development of viral resistance, which typically develops after an extended period of treatment with traditional antiviral drugs that target viral proteins.

Thus, in one aspect, the present invention provides methods for treating viral infection by administering to a patient (either a human or other animal), that is a carrier of a virus, a pharmaceutical composition or medicament having a therapeutically effective amount of a nucleic acid that induces the degradation of RNA transcripts encoding ROCK-II, or otherwise results in a specific reduction in cellular levels of ROCK-II. For example, a carrier of a virus can be identified by conventional diagnostic techniques known in the art, as described above. Once identified, the carrier can be administered with a compound containing a nucleic acid that induces the degradation of RNA transcripts encoding ROCK-II, or otherwise results in a specific reduction in cellular levels of ROCK-II, preferably in a pharmaceutical composition having a pharmaceutically acceptable carrier.

In another aspect, the present invention provides methods for treating an active viral infection by administering to a patient (either a human or other animal) that exhibits characteristic symptoms of a viral infection a pharmaceutical composition or medicament having a therapeutically effective amount of a compound containing a nucleic acid that induces the degradation of RNA transcripts encoding ROCK-II, or otherwise results in a specific reduction in cellular levels of ROCK-II. Alternatively, the presence of viral infection may be detected or determined directly by any appropriate method in the art. The infected individual so identified can be administered with a compound containing a nucleic acid that induces the degradation of RNA transcripts encoding ROCK-II, or otherwise results in a specific reduction in cellular levels of ROCK-II, preferably in a pharmaceutical composition having a pharmaceutically acceptable carrier.

In certain embodiments of the present invention, the pharmaceutical composition of the instant invention further comprises agents that either specifically enhance or increase the uptake of the nucleic acids of the present invention by target cells, or specifically enhance or improve the delivery of the nucleic acids of the present invention to the target cells. Such agents that specifically enhance or increase the uptake or delivery of the nucleic acids of the invention to their target cells are referred to, herein, as "uptake agents."

Examples of uptake agents include, but are not limited to, amphipathic compounds and compounds used to formulate liposomes or immunoliposomes. Examples of such compounds are LIPOFECTIN®, LIPOFECTAMINE®, or CELLFECTIN®, and various polycations and polyethylene glycols. Importantly, the uptake agents of the current invention include any compound that, when used in formulating the pharmaceutical composition of the instant invention, results in a net increase in the amount of the nucleic acids of the instant invention taken up by the target cells, such that at least about a 10% decrease in ROCK-II encoding transcripts, or ROCK-II protein is observed in those target cells treated with compositions including the uptake agent, as compared with cells treated with identical compositions, but lacking the uptake agent.

Examples of uptake agents that improve or enhance delivery of the nucleic acids of the instant invention to specific target organs, tissues or cells include monoclonal antibodies or other compounds that are capable of interacting with receptors on the surface of target cells or target tissues. Typically, such agents are co-formulated with the nucleic acids of the present inventions, as well as with uptake agents. An example of just such a co-formulation are the 85 nm pegylated immunoliposomes prepared by Pardridge and colleagues, and described in Zhang et al. *J. Gene. Med.* 5:1039-1045 (2003) and Zhang et al., *Clin. Cancer Res.,* 10:3667-3677 (2004), which are incorporated herein by reference in their entirety.

As is known in the art, uptake agents can be used in the formulation of liposomes, containing therapeutic nucleic acids to be taken up by target cells. Recently, uptake agents have been used in the formulation of pegylated immunoliposomes, which are capable of delivering therapeutic nucleic acids into specific organs or tissues, and promoting their uptake by specific target cells in these organs or tissues. In some cases, these methods of formulation and delivery involve the use of new polymeric compounds. Examples of such methods are taught in U.S. Patent Application publications 2003/0157030, 2004/0063654, 2004/0147027 and 2004/0156909, which are incorporated herein by reference, in their entirety. In other cases, these methods involve the use of polymeric and/or amphipathic compounds for the formulation of microparticles that contain the nucleic acids to be delivered into cells. Examples of such methods are taught in U.S. Patent Application publications 2004/0115254 and 2004/0146551, which are incorporated herein by reference, in their entirety.

Methods specific for the delivery of therapeutic nucleic acids into specific tissues of mammal, and by specific routes, have been developed. In some cases these methods make use of particular pharmaceutical formulations of nucleic acids. In other cases, specific modifications are made to the nucleic acids that are to be delivered. Examples of the modifications made to the nucleic acids themselves in order to improve the "bioavailablility" of the nucleic acids are described in PCT Patent Application Publications WO 98/49348, WO 2004/029075 and WO 2004/065579, in U.S. Pat. Nos. 6,153,737 and 6,395,492, and in U.S. Patent Application Publications 2002/0188101 and 2003/0064492. Examples of modifications made to the nucleic acids to produce "long-circulating liposomal compositions are described in PCT Patent Application Publication WO 99/59547. Methods of using such modified oligonucleotides in formulations for hepatic delivery are described in PCT Patent Application Publication WO 03/072711. Similarly, compositions and methods of using modified oligonucleotides for topical delivery are described in PCT Patent Application Publication WO 99/60617. Also, compositions and methods of using modified oligonucleotides for pulmonary delivery are described in PCT Patent Application Publication WO 99/60010 and WO 99/60166, and in U.S. Patent Application Publications 2003/0157030 and 2004/0063654. And, compositions and methods of using modified oligonucleotides for delivery via the alimentary canal are described in PCT Patent Application Publication WO 99/01579 and WO 99/60012, as well as in U.S. Pat. No. 6,747,014, with the latter two publications specifically teaching methods for rectal administration of therapeutic nucleic acids. All of these aforementioned patent applications and published patents describing methods for improved uptake and delivery of therapeutic nucleic acids and modified oligonucleotides are incorporated herein by reference in their entirety.

Even more recently, sophisticated methods and pharmaceutical formulations have been developed for the delivery of therapeutic nucleic acids into particular organs of mammals, and in some cases into specific cells in the organs of mammals—in particular, delivery of siRNAs into the brains of rats. The use of cationic liposomes to facilitate the uptake of siRNAs by a variety of tissues in mice, were described by Sorensen and coworkers (Sorensen, et al. *J. Mol. Biol.* 327:761-766 (2003)), which is incorporated herein by reference in its entirety. Methods to deliver therapeutic nucleic acids into cancer cells within the brains of mice are described in two publications by Pardridge and colleagues ((Zhang et al., *J. Gene Med.* 5:1039-1045 (2003) and Zhang et al., *Clin Cancer Res.* 10:3667-3677 (2004)), which are both incorporated herein by reference in their entirety. In these studies, shRNA expression plasmids were encapsulated into 85 nm pegylated immunoliposomes, which were studded with monoclonal antibodies selected to interact with specific cellular receptors. Interactions between the monoclonal antibodies on the surface of the immunoliposomes facilitated their uptake across the blood-brain barrier and into cancer cells within the brains of the mice. Similar techniques, in which the nucleic acids of the instant invention are formulated in to pegylated immunoliposomes, as described by Pardridge and coworkers, can be used to deliver the therapeutic nucleic acids of the instant invention to particular target organs, tissues, or cells, in order to treat viral infections.

Therapeutic Applications:

Accordingly, the methods of the present invention may be generally useful in treating or preventing the onset of symptoms of diseases or disorders associated with viral infection in animals, particularly humans. Such viral infection can be caused by viruses including, but not limited to, lentiviruses such as human immunodeficiency virus types 1, 2 and 3 (HIV), human T-cell lymphotropic virus type 1 and 2 (HTLV-I and HTLV-II), SIV, EIAV (equine infectious anemia virus), BIV, FIV, CAEV, VMV, and MMLV (Moloney murine leukemia virus). Such viral infections can also be caused by hepatitis A virus, hepatitis B virus, hepatitis C virus, hepatitis D virus, hepatitis E virus, hepatitis G virus, human foamy virus, or by human herpesviruses (e.g., herpes simplex virus type-1, herpes simplex virus type-2, herpes simplex virus type-3 (also known as Varicella-zoster virus), herpes simplex virus type-4 (also known as Epstein-Barr virus or EBV), herpes simplex virus type-5, and herpes simplex virus type-7). Such viral infections can also be caused by influenza viruses (types A, B or C), human parainfluenza viruses, respiratory syncytial virus, smallpox virus (variola virus), monkeypox virus, vaccinia virus, human papilloma virus, human parechovirus 2, mumps virus, Measles virus, Rubella virus, Semliki Forest virus, West Nile virus, Colorado tick fever virus, foot-and-mouth disease virus, Ebola virus, Marburg virus, polyomavirus, TT virus, Lassa virus, lymphocytic choriomeningitis virus, vesicular stomatitis virus, rotavirus, varicella virus, parvovirus, cytomegalovirus, encephalitis viruses, adenovirus, echovirus, rhinoviruses, filoviruses, coxachievirus, coronavirus (such as SARS-associated coronavirus), Dengue viruses, yellow fever virus, hantaviruses, regional hemorrhagic fever viruses, molluscum virus, poliovirus, rabiesvirus, etc. In preferred embodiments, the methods can be used in treating or preventing infection by viruses that utilize cellular machineries of membrane/vesicle trafficking or cellular multivesicular body (MVB) sorting pathway. In more preferred embodiments, the methods provided are used in treating or preventing infections by enveloped viruses. In specific embodiments, as described below, particular viruses that are known to infect humans, and cause disease, are treated by the methods of the present invention.

Embodiments for Specific Viruses

HIV:

As used herein, the term "HIV infection" generally encompasses infection of a host animal, particularly a human host, by the human immunodeficiency virus (HIV) family of retroviruses including, but not limited to, HIV I (also known as HTLV-III), HIV II (also known as LAV-1), HIV III (also known as LAV-2), and the like. "HIV" can be used herein to refer to any strains, forms, subtypes, clades and variations in the HIV family. Thus, treating HIV infection will encompass the treatment of a person who is a carrier of any of the HIV family of retroviruses or a person who is diagnosed of active AIDS, as well as the treatment or prophylaxis of the AIDS-related conditions in such persons. A carrier of HIV may be identified by any methods known in the art. For example, a person can be identified as HIV carrier on the basis that the person is anti-HIV antibody positive, or is HIV-positive, or has symptoms of AIDS. That is, "treating HIV infection" should be understood as treating a patient who is at any one of the several stages of HIV infection progression, which, for example, include acute primary infection syndrome (which can be asymptomatic or associated with an influenza-like illness with fevers, malaise, diarrhea and neurological symptoms such as headache), asymptomatic infection (which is the long latent period with a gradual decline in the number of circulating CD4 T-cells), and AIDS (which is defined by more serious AIDS-defining illnesses and/or a decline in the circulating CD4 T-cell count to below a level that is compatible with effective immune function).

As used herein, the term "delaying the onset of HIV infection" means treating an individual who (1) is at risk of infection by HIV, or (2) is suspected of infection by HIV or of exposure to HIV, or (3) has suspected past exposure to HIV, to delay the onset of acute primary infection syndrome by at least three months. As is known in the art, clinical findings typically associated with acute primary infection syndrome may include an influenza-like illness with fevers, malaise, nausea/vomiting/diarrhea, pharyngitis, lymphadenopathy, myalgias, and neurological symptoms such as headache, encephalitis, etc. The individuals at risk may be people who perform any of following acts: contact with HIV-contaminated blood, blood transfusion, exchange of body fluids, "unsafe" sex with an infected person, accidental needle stick, injection of drug with contaminated needles or syringes, receiving a tattoo or acupuncture with contaminated instruments, or transmission of the virus from a mother to a baby during pregnancy, delivery or shortly thereafter. The term "delaying the onset of HIV infection" may also encompass treating a person who has not been diagnosed as having HIV infection but is believed to be at risk of infection by HIV, or has been exposed to HIV through contaminated blood, etc.

In addition, the term "delay the onset of AIDS" means delaying the onset of AIDS (which is characterized by more serious AIDS-defining illnesses and/or a decline in the circulating CD4 cell count to below a level that is compatible with effective immune function, i.e. below about 200/μl) and/or AIDS-related conditions, by treating an individual (1) at risk of infection by HIV, or suspected of being infected with HIV, or (2) having HIV infection but not AIDS, to delay the onset of AIDS by at least six months. Individuals at risk of HIV infection may be those who are suspected of past exposure, or considered to be at risk of present or future exposure, to HIV by, e.g., contact with HIV-contaminated blood, blood transfusion, transplantation, exchange of body fluids, "unsafe" sex with an infected person, accidental needle stick, receiving a tattoo or acupuncture with contaminated instruments, or transmission of the virus from a mother to a baby during pregnancy, delivery or shortly thereafter.

The term "treating AIDS" means treating a patient who exhibits more serious AIDS-defining illnesses and/or a decline in the circulating CD4 cell count to below a level that is compatible with effective immune function (typically below about 200/μl). The term "treating AIDS" also encompasses treating AIDS-related conditions, which means disorders and diseases incidental to or associated with AIDS or HIV infection such as AIDS-related complex (ARC), progressive generalized lymphadenopathy (PGL), anti-HIV antibody positive conditions, and HIV-positive conditions, AIDS-related neurological conditions (such as dementia or tropical paraparesis), Kaposi's sarcoma, thrombocytopenia purpurea and associated opportunistic infections such as *Pneumocystis carinii* pneumonia, *Mycobacterial tuberculosis*, esophageal candidiasis, toxoplasmosis of the brain, CMV retinitis, HIV-related encephalopathy, HIV-related wasting syndrome, etc.

HBV:

As used herein, the term "HBV infection" generally encompasses infection of a human by any strain or serotype of hepatitis B virus, including acute hepatitis B infection and chronic hepatitis B infection. Thus, treating HBV infection means the treatment of a person who is a carrier of any strain or serotype of hepatitis B virus, or a person who is diagnosed with active hepatitis B, to reduce the HBV viral load in that person or to alleviate one or more symptoms associated with HBV infection and/or hepatitis B, including, e.g., nausea and vomiting, loss of appetite, fatigue, muscle and joint aches, elevated transaminase blood levels, increased prothrombin time, jaundice (yellow discoloration of the eyes and body) and dark urine. A carrier of HBV may be identified by any methods known in the art. For example, a person can be identified as HBV carrier on the basis that the person is anti-HBV antibody positive (e.g., based on hepatitis B core antibody or hepatitis B surface antibody), or is HBV-positive (e.g., based on hepatitis B surface antigens (HBeAg or HbsAg) or HBV RNA or DNA) or has symptoms of hepatitis B infection or hepatitis B. Hence, "treating HBV infection" should be understood as treating a patient who is at any one of the several stages of HBV infection progression. In addition, the term "treating HBV infection" will also encompass treating individuals with a suspected HBV infection after suspected exposure to HBV by, e.g., contact with HBV-contaminated blood, blood transfusion, exchange of body fluids, "unsafe" sex with an infected person, accidental needle stick, receiving a tattoo or acupuncture with contaminated instruments, or transmission of the virus from a mother to a baby during pregnancy, delivery or shortly thereafter. The term "treating HBV infection" will also encompass treating a person who is free of HBV infection but is believed to be at risk of infection by HBV.

In yet another aspect, a method of treating HBV infection in a patient co-infected with HBV and HIV is provided by administering a therapeutically effective amount of a compound containing a nucleic acid that induces the degradation of RNA transcripts encoding ROCK-II, or otherwise results in a specific reduction in cellular levels of ROCK-II, to such a patient. Particularly, HIV infection is associated with an approximate threefold increase in the development of persistent hepatitis B. RNAs that induces the degradation of RNA transcripts encoding ROCK-II, or otherwise results in a specific reduction in cellular levels of ROCK-II, are particularly suitable for patients co-infected with HIV and HBV. Particularly, such RNAs are especially effective in inhibiting HBV infection and/or egress. Moreover, the compounds are also effective in inhibiting HIV entry into and/or egress (particularly budding) from host cells. The presently marketed drug interferon alpha is not effective in treating HBV and HIV co-infection. Lamivudine and some other reverse transcriptase inhibitors are useful in treating such co-infections, but Lamivudine is particularly toxic and can cause hepatic injury, which worsens hepatitis B. In addition, such reverse transcriptase inhibitors often must be used in cocktails. In contrast, the RNAs according to the present invention can be significantly less toxic, and are less likely to result in evolved viral resistance. Thus, in accordance with the present invention, a compound containing a nucleic acid that induces the degradation of RNA transcripts encoding ROCK-II, or otherwise results in a specific reduction in cellular levels of ROCK-II, is administered alone, or in combination with another anti-HIV or anti-HBV drug, in a therapeutically effective amount to a mammal, particularly a human co-infected with both HBV and HIV. The method may include a step of identifying a patient co-infected with HBV and HIV by techniques commonly known in the art. For example, PCR tests can be used to detect HBV DNA or RNA and HIV RNA in blood samples obtained from a test subject. Alternatively, virus-specific antibodies or antigens may be also employed for the detection of HBV and HIV infection.

The term "preventing hepatitis B" as used herein means preventing in a patient who has an HBV infection, is suspected to have an HBV infection, or is at risk of contracting an HBV infection, from developing hepatitis B (which are characterized by more serious hepatitis-defining symptoms), cirrhosis, or hepatocellular carcinoma.

HCV:

As used herein, the term "HCV infection" generally encompasses infection of a human by any types or subtypes of hepatitis C virus, including acute hepatitis C infection and chronic hepatitis C infection. Thus, treating HCV infection means the treatment of a person who is a carrier of any types or subtypes of hepatitis C virus, or a person who is diagnosed with active hepatitis C, to reduce the HCV viral load in that person or to alleviate one or more symptoms associated with HCV infection and/or hepatitis C. A carrier of HCV may be identified by any methods known in the art. For example, a person can be identified as HCV carrier on the basis that the person is anti-HCV antibody positive, or is HCV-positive (e.g., based on HCV RNA or DNA) or has symptoms of hepatitis C infection or hepatitis C (e.g., elevated serum transaminases). Hence, "treating HCV infection" should be understood as treating a patient who is at any one of the several stages of HCV infection progression. In addition, the term "treating HCV infection" will also encompass treating individuals with a suspected HCV infection after suspected past exposure to HCV by, e.g., contact with HCV-contaminated blood, blood transfusion, exchange of body fluids, "unsafe" sex with an infected person, accidental needle stick, receiving a tattoo or acupuncture with contaminated instruments, or transmission of the virus from a mother to a baby during pregnancy, delivery or shortly thereafter. The term "treating HCV infection" will also encompass treating a person who is free of HCV infection but is believed to be at risk of infection by HCV. The term of "preventing HCV" as used herein means preventing in a patient who has HCV infection or is suspected to have HCV infection or is at risk of HCV infection from developing hepatitis C (which is characterized by more serious hepatitis-defining symptoms), cirrhosis, or hepatocellular carcinoma.

Importantly, about one quarter of all HIV-infected persons in the United States, or an estimated 200,000 people, are infected with both HCV and HIV (See National Center for HIV, STD and TB Prevention report at the Centers for Disease Control and Prevention website and Thomas, D. L. *Hepatology* 36:S201-S209 (2002)). As the lives of HIV-infected persons have been prolonged by use of highly active antiretroviral therapy, liver disease has emerged as an important, and in some settings, the leading cause of morbidity and mortality. HIV infection appears to adversely affect all stages of HCV infection. Particularly, HIV infection is associated with a significant increase in the development of persistent hepatitis C, with higher titers of HCV, more rapid progression to HCV-related liver disease, and an increased risk for HCV-related cirrhosis (scarring) of the liver. In turn, HCV may affect the management of HIV infection, increasing the incidence of liver toxicity caused by antiretroviral medications (Thomas, D. L. *Hepatology* 36:S201-S209, (2002) and National Center for HIV, STD and TB Prevention report at the Centers for Disease Control and Prevention website).

In the United States, two different treatment regimens have been approved as therapy for chronic hepatitis C: monotherapy with alpha interferon and combination therapy with alpha interferon and ribavirin. Among HIV-negative persons with chronic hepatitis C, combination therapy consistently yields higher rates (30%-40%) of sustained response than monotherapy (10%-20%). Combination therapy is more effective against viral genotypes 2 and 3, and requires a shorter course of treatment; however, viral genotype 1 is the most common among U.S. patients. Combination therapy is associated with more side effects than monotherapy, but, in most situations, it is preferable. At present, interferon monotherapy is reserved for patients who have contraindications to the use of ribavirin. (See, the Centers for Disease Control and Prevention website.)

Hence, in yet another aspect, a method of treating HCV infection in a patient co-infected with HCV and HIV is provided by administering a therapeutically effective amount of a compound containing a nucleic acid molecule that induces the degradation of RNA transcripts encoding ROCK-II, or otherwise results in a specific reduction in cellular levels of ROCK-II, to such a patient. RNAs that induce the degradation of RNA transcripts encoding ROCK-II are particularly suitable for patients co-infected with HIV and HCV. Particularly, the RNAs are especially effective in inhibiting HCV infection and/or egress from host cells. Moreover, the RNAs are also effective in inhibiting HIV entry into and/or egress (particularly budding) from host cells. In contrast to the combination therapy described above, the RNAs according to the present invention are significantly less toxic, and are less like to result in evolved viral resistance. Thus, in accordance with the present invention, a compound containing a nucleic acid that induces the degradation of RNA transcripts encoding ROCK-II, or otherwise results in a specific reduction in cellular levels of ROCK-II, is administered alone, or in combination with another anti-HIV or anti-HCV drug, in a therapeutically effective amount to a mammal, particularly a human co-infected with both HCV and HIV. The method may include a step of identifying a patient co-infected with HCV and HIV by techniques commonly known in the art. For example, PCR tests can be used to detect HCV DNA or RNA and HIV RNA in blood samples obtained from a test subject. Alternatively, virus-specific antibodies or antigens may be also employed for the detection of HCV and HIV infection.

Herpesviruses:

Herpesviruses are one of the most common human pathogens. Members of the herpesvirus family include herpes simplex virus type-1 (HSV-1), herpes simplex virus type-2 (HSV-2), Varicella-zoster virus (herpes simplex virus type-3 or HSV-3; also known as chicken pox), and Epstein-Barr virus (herpes simplex virus type-4 or HSV-4). HSV-1 commonly causes herpes labial (also called oral herpes, cold sores, fever blisters), which are highly infectious open sores that crust over before healing. HSV-1 can also cause eye and brain infection. HSV-2 commonly causes genital herpes. HSV-1 can also cause genital herpes, though far less frequently than HSV-2. After an initial infectious cycle, HSV-1 and HSV-2 generally establish life-long latent infections in sensory neurons near the site of infection. These latent infections exist without showing any signs or symptoms of infection or disease, until some event reactivates the virus. Reactivation generally causes recurrent lesions close to, or in the same location as, the site of initial infection. Reactivation seems to occur during periods of emotional stress, or periods of reduced immune system function.

In addition to oral and genital herpes, HSV-1 and HSV-2 can cause other diseases. Examples of such diseases include herpes simplex encephalitis—a rare but potentially fatal herpetic infection of the brain; neonatal herpes,—a rare but potentially severe HSV infection in newborns (resulting from transmission of the virus from the mother to the baby during delivery); herpetic whitlow—an HSV infection of the finger (acquired either from transfer of the infection from another part of the body or from direct contact with another party having an HSV infection); and herpes keratitis—an HSV infection of the eye (one of the most common causes of blindness). Thus, herpes simplex virus infection of humans is a significant health problem.

Genital herpes is primarily treated with suppressive and episodic therapies. Suppressive therapy is used to treat outbreaks before they occur, while episodic therapy treats outbreaks when they occur. Treatment with valacyclovir HCl, acyclovir, and famciclovir, can be used in both suppressive and episodic therapies.

Currently there is no known cure for HSV-1 infection. The available antiviral therapies are not completely effective and there is a chance that the virus will become resistant to the treatment. Thus, there is a clear need for improved methods and compositions for treating HSV-1.

Epstein-Barr virus (herpes simplex virus-4), hereafter referred to as "EBV", occurs worldwide. In fact, most people become infected with EBV during their lives. A large percentage of adults in the United States have been infected. Infants are susceptible to EBV as soon as maternal antibody protection present at birth disappears. Many children become infected with EBV, and these infections usually cause no symptoms. The symptoms of EBV infection in children can be indistinguishable from the symptoms of other typical childhood illnesses. Individuals not infected as a child have a risk of being infected during adolescence or young adulthood, which often causes infectious mononucleosis (mono). Symptoms of infectious mononucleosis include fever, sore throat, and swollen lymph glands, less often a swollen spleen or liver involvement may develop. Rarely, heart problems or involvement of the central nervous system occur. Infectious mononucleosis is almost never fatal. The symptoms of infectious mononucleosis usually resolve in 1 or 2 months, but EBV remains dormant or latent in a few cells in the throat and blood for the rest of the infected person's life. Periodically, the virus can reactivate and is commonly found in the saliva of infected persons. Reactivation usually occurs without symptoms of illness.

EBV is thought to be associated with a number of other diseases including Burkitt's lymphoma, nasopharyngeal carcinoma, and Hodgkin's disease. Diseases caused by EBV are particularly common among people with reduced immunity. EBV is associated with a tumor often found in organ transplant patients suffering from what is referred to as post-transplant lymphoproliferative disease. The immune systems of such patients are usually artificially suppressed by drug therapy to help prevent the body from rejecting the new organ. Individuals infected with HIV, and have AIDS, also have reduced immunity and commonly suffer from oral hairy leukoplakia, a condition involving considerable replication of EBV in cells along the edge of the tongue. It has also been suggested that the high incidence of malaria in countries where Burkitt's lymphoma is prevalent may also play a role in the disease by suppressing the body's immune system.

Scientists are finding it difficult to explain why the virus causes a relatively mild disease like glandular fever in some people and malignant tumors in others. Genetic factors may play a role. Regardless, treatments are needed to combat EBV.

As used herein, the terms "herpes simplex virus" or HSV refers to any strain of herpes simplex virus, including, but not limited to HSV-1, HSV-2, HSV-3 (Varcella-zoster virus or chicken pox), and HSV-4 (or EBV). Thus, "treating HSV infections" will encompass the treatment of a person who is actively infected with, or carrier of a latent infection of, any of the HSV family of herpes viruses.

As used herein, the term "HSV infection" generally encompasses infection of a human by any strain of herpes simplex virus, and includes both active and latent infections. Thus, "treating HSV infection" means the treatment of a person who is a carrier of any strain of HSV. For example, a person can be identified as an HSV carrier on the basis that the person is anti-HSV antibody positive or has symptoms of an HSV infection. Hence, "treating HSV infection" should be understood as treating a patient who is at any one of the several stages of HSV infection progression. In addition, the term "treating HSV infection" will also encompass treating individuals with a suspected HSV infection after suspected exposure to HSV by, e.g., contact with HSV-contaminated blood, blood transfusion, exchange of body fluids, "unsafe" sex with an infected person, accidental needle stick, receiving a tattoo or acupuncture with contaminated instruments, or transmission of the virus from a mother to a baby during pregnancy, delivery or shortly thereafter. The term "treating HSV infection" will also encompass treating a person who is free of HSV infection but is believed to be at risk of infection by HSV.

In yet another aspect, a method of treating HSV infection in a patient co-infected with HSV and HIV is provided by administering a therapeutically effective amount of a compound containing a nucleic acid that induces the degradation of RNA transcripts encoding ROCK-II, or otherwise results in a specific reduction in cellular levels of ROCK-II, to such a patient. Particularly, HIV infection is associated with an increase in active HSV infections, presumably due to the immunocompromised state created by the HIV infection. The RNAs that induces the degradation of RNA transcripts encoding ROCK-II, or otherwise results in a specific reduction in cellular levels of ROCK-II, are particularly suitable for patients co-infected with HIV and HSV. Particularly, the RNAs are especially effective in inhibiting HSV infection and/or egress. Moreover, the compounds are also effective in inhibiting HIV entry into and/or egress (particularly budding) from host cells. The presently marketed drug interferon alpha is not effective in treating HBV and HIV co-infection. Lamivudine and some other reverse transcriptase inhibitors are useful in treating such co-infections, but Lamivudine is particularly toxic and can cause hepatic injury, which worsens hepatitis B. In addition, such reverse transcriptase inhibitors often must be used in cocktails. In contrast, the RNAs according to the present invention can be significantly less toxic, and are less likely to result in evolved viral resistance. Thus, in accordance with the present invention, a compound containing a nucleic acid that induces the degradation of RNA transcripts encoding ROCK-II, or otherwise results in a specific reduction in cellular levels of ROCK-II, is administered alone, or in combination with another anti-HIV or anti-HSV drug, in a therapeutically effective amount to a mammal, particularly a human co-infected with both HSV and HIV. The method may include a step of identifying a patient co-infected with HSV and HIV by techniques commonly known in the art. For example, PCR tests can be used to detect HSV DNA or RNA and HIV RNA in blood samples obtained from a test subject. Alternatively, virus-specific antibodies or antigens may be also employed for the detection of HSV and HIV infection.

The term "delaying the onset of HSV-associated symptoms" as used herein means preventing in a patient who has an HSV infection, is suspected to have an HSV infection, or is at risk of contracting an HSV infection, from developing oral herpes, genital herpes, chickenpox or shingles, or a chronic EBV infection.

Influenza:

Influenza infection is associated with an average of 36,000 deaths and 114,000 hospitalizations per year in the United States alone. Although there are three recognized types of influenza viruses, influenza A, B, and C, types A and B are responsible for annual winter flu epidemics. Influenza A infects many different animal species besides humans, including ducks, chickens, pigs, whales, horses, and seals. Influenza B viruses generally only infect humans.

All three types of influenza virus have genomes composed of eight different RNA helices, which encodes a single gene and are bound by a nucleoprotein that determines the viral type: A, B, or C. In effect, the influenza genome is made up of eight separate pieces of nucleic acid that can come together to form viruses with new combinations of viral genes when cells become co-infected by more than one viral type. Two of these RNA helices encode the important viral surface proteins hemagglutinin and neuraminidase, which are embedded in the lipid bilayer of a mature virus particle.

Variations in the viral hemagglutinin and neuraminidase determine the viral subtype. Hemagglutinin is responsible for entry of the virus into the host cell, while neuraminidase is important in the release of newly formed viruses from the infected cells. Antibodies to hemagglutinin can neutralize the virus and are the major determinant for immunity. Antibodies to neuraminidase do not neutralize the virus but may limit viral replication and the course of infection. Host antibodies to specific types of hemagglutinin and neuraminidase prevent and generally ameliorate future infection by the same viral strain. However, since the genetic makeup of viral strains is dynamic and ever-changing, immunity gained through successful resistance to one strain gained during an infection one year may be useless in combating a new, recombined, variant strain the next year.

Epidemics of influenza are thought to result when viral strains change over time by the process of antigenic drift. Antigenic drift (caused by mutations in the principal viral antigen genes, especially in the hemagglutinin or neuraminidase genes) results in small changes in surface antigens, and occurs essentially continuously over time. When these changes occur in the right places in the genes, they render the new antigens unrecognizable by the antibodies raised against other influenza virus strains during previous infections.

Influenza pandemics (or worldwide epidemics) occur as a result of "antigenic shift." Antigenic shift is an abrupt, major change in an influenza A virus that results from a new hemagglutinin and/or new hemagglutinin and neuraminidase protein appearing in an influenza A strain. Such shifts are generally thought to occur when a new combination of viral genomic RNAs is created, possibly in a non-human specie, and that new combination is passed to humans. When such an antigenic shift occurs, most humans have little or no protection against the virus, and an infection can prove lethal.

Influenza pandemics have resulted in massive loss of life during the history of man. The influenza pandemic of 1918-1919 resulted in the deaths of about 20-40 million people. In support of the antigenic shift hypothesis presented above, molecular analyses recently demonstrated that the influenza virus responsible for the 1918-19 pandemic is related to a swine influenza virus that belongs to the same family of influenza virus that still causes the flu in humans today.

Two categories of treatment/preventative strategies are available for influenza infection: vaccination with "the flu shot" and administration of antiviral drugs. The flu shot involves vaccination with killed or inactivated influenza viruses. The antiviral drugs available for treating influenza infection including amantadine, rimantadine, zanamivir, and osteltamivir. Amantadine and rimantadine are used for treating and preventing influenza A infection, zanamivir is used for treating influenza A and B infection, and osteltamivir is used for treating and preventing influenza A and B infection.

Despite the numerous drugs and vaccinations available, there is a need for improved methods and compositions for both treating and preventing influenza infection.

As used herein, the term "influenza" and "influenza virus" refer to any type or subtype of influenza, including types A, B and C, and all subtypes thereof. Consequently, the term "influenza infection" encompasses infection by any strain of influenza, and the term "treating influenza infection" is understood to mean the treatment of an animal, particularly a human, infected by any strain of influenza. In addition, the term "treating influenza infection" will also encompass treating individuals with a suspected influenza infection after suspected exposure to influenza. The term "treating influenza infection" will also encompass treating a person who is apparently free of an influenza infection but is believed to be at risk of infection by influenza.

Poxviruses:

As used herein, the terms "smallpox virus" or "variola virus" refers to any strain of smallpox virus including variola major and variola minor (also referred to as alastrim). Examples of such human variola virus isolates are well known and the complete genomic nucleotide sequence one strain has been determined (See, e.g., Harrison's 15$^{th}$ Edition Principles of Internal Medicine, Braunwald et al. EDS. McGraw-Hill, United States, and Genbank accession no. NC_001611). Skilled artisans are capable of diagnosing individuals infected or suspected of being infected with smallpox. The term "treating smallpox" or "treating variola virus" refers to both treating the symptoms of the disease as well as reducing the viral load, infectivity and/or replication of the virus. The term of "delaying the onset of symptoms associated with smallpox infection" as used herein means treating a patient who is free of smallpox infection, or is believed to be at risk of infection by smallpox, or is infected with smallpox to delay the onset of one or more symptoms associated with smallpox infection by at least 3 months. The term "treating smallpox" also encompasses treating a person who either has smallpox infection, is suspected to have smallpox infection, or is at risk of developing smallpox from a smallpox virus infection (which is characterized by more serious smallpox-defining symptoms like macular rash, fever, vesicular lesions and pustular lesions).

An outbreak of monkeypox occurred for the first time in the United States in June of 2003. The causative agent is the monkeypox virus, which belongs to the group of viruses that includes the smallpox virus (variola), the virus used in the smallpox vaccine (vaccinia), and the cowpox virus. In humans, the signs and symptoms of monkeypox are like those of smallpox, but usually much milder, although monkeypox, unlike smallpox causes the lymph nodes to swell. In Africa, where most cases of monkeypox are known to occur, infections result in deaths of between 1% and 10% of infected individuals. As used herein, the term "treating monkeypox" or "treating monkeypox virus" refers to both treating the symptoms of the disease as well as reducing the viral load, infectivity and/or replication of the virus. The term of "preventing monkeypox infection" as used herein means preventing infection in a patient who is free of monkeypox infection but is believed to be at risk of infection by monkeypox. The term of "delaying the onset of symptoms associated with monkeypox infection" as used herein means treating a patient who is free of monkeypox infection, or is believed to be at risk of infection by monkeypox, or is infected with monkeypox to delay the onset of one or more symptoms associated with monkeypox infection by at least 3 months.

Cornaviruses:

As used herein, the terms "SARS-CoV", "SARS" or "SARS-associated Cornavirus" refers to any strain of coronavirus associated with severe acute respiratory syndrome. Examples of such human coronavirus isolates are known as HCoV-OC43 and HCoV-229E (See, e.g., Marra et al. *Science* 300:1399 (2003) and Rota et al. Science 300:1394 (2003)(Genbank accession no. AY278741). Skilled artisans are capable of diagnosing individuals infected or suspected of being infected with a SARS associated Coronavirus. The term "treating SARS" or "treating SARS associated Cornavirus" refers to both treating the symptoms of the disease, as well as reducing the infectivity and/or replication of the SARS-associated Coronavirus. The term "treating SARS" also encompasses treating a person who is free of SARS-CoV infection but is believed to be at risk of infection by SARS-CoV. The term of "preventing SARS" as used herein means preventing in a patient who has SARS-CoV infection or is suspected to have SARS-CoV infection or is at risk of SARS-CoV infection from developing SARS (which is characterized by more serious SARS-CoV-defining symptoms like severe respiratory illness, fever, dry nonproductive cough, shortness of breath, and atypical pneumonia).

West Nile Virus:

West Nile (WN) virus has emerged in recent years in temperate regions of Europe and North America, presenting a threat to public, equine, and animal health. The most serious manifestation of WN virus infection is fatal encephalitis (inflammation of the brain) in humans and horses, as well as mortality in certain domestic and wild birds. WN virus infection is a growing problem in North America. During 2002 in the United States alone, there were 4,156 documented cases of WN virus infections of humans and 284 deaths. As used herein, the terms "treating West Nile virus," "treating West Nile disease" refer to treating the symptoms of the disease in both known and suspected cases of WN virus infection.

Therapeutic Embodiments siRNA/shRNA Therapy:

In one embodiment, siRNA compounds specific to nucleic acids encoding ROCK-II are administered to cells or tissue in vitro or in a patient to be therapeutically or prophylactically treated. These siRNA molecules are provided such that, when introduced into cells, they result in the reduction of RNA transcripts encoding ROCK-II by at least a 10%, 20%, 30%, or greater, reduction in cellular ROCK-II mRNA levels, and/or a 10%, 20%, 30%, or greater, reduction in cellular ROCK-II protein levels. Preferably such RNAs reduce ROCK-II mRNA and/or ROCK-II protein levels by 40%, 50%, 60%, or more. More preferably such RNAs reduce ROCK-II mRNA and/or ROCK-II protein levels by 70%, 75%, 80%, 85%, 90%, 95% or more.

In another embodiment, shRNA compounds specific to nucleic acids encoding ROCK-II are administered to cells or tissue in vitro or in a patient to be therapeutically or prophylactically treated. These shRNA molecules are provided such that, when introduced into cells, they result in the reduction of RNA transcripts encoding ROCK-II by at least a 10%, 20%, 30%, or greater, reduction in cellular ROCK-II mRNA levels, and/or a 10%, 20%, 30%, or greater, reduction in cellular ROCK-II protein levels. Preferably such RNAs reduce ROCK-II mRNA and/or ROCK-II protein levels by 40%, 50%, 60%, or more. More preferably such RNAs reduce ROCK-II mRNA and/or ROCK-II protein levels by 70%, 75%, 80%, 85%, 90%, 95% or more.

As is generally known in the art now, siRNA compounds are RNA duplexes comprising two complementary single-stranded RNAs of 21 nucleotides that form 19 base pairs and possess 3' overhangs of two nucleotides. See Elbashir et al., *Nature* 411:494-498 (2001); and PCT Publication Nos. WO 00/44895; WO 01/36646; WO 99/32619; WO 00/01846; WO 01/29058; WO 99/07409; and WO 00/44914, all of which are incorporated herein by reference in their entirety. When appropriately targeted via its nucleotide sequence to a specific mRNA in cells, an siRNA can specifically suppress gene expression through a process known as RNA interference (RNAi). See e.g., Zamore & Aronin, *Nature Medicine,* 9:266-267 (2003). siRNAs can reduce the cellular level of specific mRNAs, and decrease the level of proteins coded by such mRNAs. siRNAs utilize sequence complementarity to target an mRNA for destruction, and are therefore sequence-specific. Thus, they can be highly target-specific, and in mammals have been shown to specifically target mRNAs encoded by different alleles of the same gene. In fact, the siRNA-mediated allele-specific silencing of two different dominant disease genes in human cells has recently been demonstrated (Miller et al., *Proc. Natl. Acad. Sci. USA* 100:7195-7200 (2003); Gonzalez-Alegre, et al., *Ann. Neurol.* 53:781-787 (2003)). Similarly, in eukaryotes in general, if an siRNA bears sequence complementarity to a sequence present in an exon that is only found in a particular splice form of a transcript, that siRNA will only induce the silencing of the products corresponding to that particular splice form. Because of this specificity and precision, side effects typically associated with traditional drugs can be reduced or eliminated. In addition, siRNAs are relatively stable, and like antisense and ribozyme molecules, they can also be modified to achieve improved pharmaceutical characteristics, such as increased stability (i.e., resistance to nucleases) deliverability, and ease of manufacture. Moreover, because siRNA molecules take advantage of a natural cellular pathway, i.e., RNA interference, they are often highly efficient in inducing the destruction of targeted mRNA molecules. As a result, it is possible to achieve a therapeutically effective concentration of an siRNA compound in patients. Thus, siRNAs are a promising new class of drugs being actively developed by pharmaceutical companies.

Indeed, in vivo inhibition of specific gene expression by RNAi has been achieved in variety of organisms including mammals. For example, Song et al., *Nature Medicine,* 9:347-351 (2003) discloses that intravenous injection of Fas siRNA compounds into laboratory mice with autoimmune hepatitis specifically reduced Fas mRNA levels and expression of Fas protein in mouse liver cells. The gene silencing effect observed persisted without diminution for 10 days after the intravenous injection. The injected siRNA was effective in protecting the mice from liver failure and fibrosis (Song et al., *Nature Medicine,* 9:347-351 (2003)). Several other approaches for delivery of siRNA into animals have also proved to be successful. See e.g., McCaffery et al., *Nature,* 418:38-39 (2002); Lewis et al., *Nature Genetics,* 32:107-108 (2002); Xia et al., *Nature Biotech.,* 20:1006-1010 (2002); Sorensen et al., *J. Mol. Biol.* 327:761-766 (2003); Zhang, et al., *J. Gene. Med.* 5:1039-1045 (2003); and Zhang, et al., *Clin. Cancer Res.* 10:3667-3677 (2004); all of which are incorporated herein by reference in their entirety.

The siRNA compounds provided according to the present invention can be synthesized using conventional RNA synthesis methods. For example, they can be chemically synthesized using appropriately protected ribonucleoside phosphoramidites and a conventional DNA/RNA synthesizer. Various applicable methods for RNA synthesis are disclosed in, e.g., Usman et al., *J. Am. Chem. Soc.,* 109:7845-7854 (1987) and Scaringe et al., *Nucleic Acids Res.,* 18:5433-5441 (1990), which are incorporated herein by reference in their entirety. Custom and large-scale siRNA synthesis services are available from commercial vendors such as Ambion (Austin, Tex., USA), Dharmacon Research (Lafayette, Colo., USA), Pierce Chemical (Rockford, Ill., USA), ChemGenes (Ashland, Mass., USA), Proligo (Hamburg, Germany), and Cruachem (Glasgow, UK).

As used herein, “modified equivalent” means a modified form of a particular siRNA compound having the same target-specificity (i.e., recognizing the same mRNA molecules that complement the unmodified particular siRNA compound). Thus, a modified equivalent of an unmodified siRNA compound can have modified ribonucleotides, that is, ribonucleotides that contain a modification in the chemical structure of an unmodified nucleotide base, sugar and/or phosphate (or phosphodiester linkage). As is known in the art, an “unmodified ribonucleotides” has one of the bases adenine, cytosine, guanine, and uracil joined to the 1' carbon of beta-D-ribo-furanose.

Preferably, modified siRNA compounds contain modified backbones or non-natural internucleoside linkages, e.g., modified phosphorous-containing backbones and non-phosphorous backbones such as morpholino backbones; siloxane, sulfide, sulfoxide, sulfone, sulfonate, sulfonamide, and sulfamate backbones; formacetyl and thioformacetyl backbones; alkene-containing backbones; methyleneimino and methylenehydrazino backbones; amide backbones, and the like.

Examples of modified phosphorous-containing backbones include, but are not limited to phosphorothioates, phosphorodithioates, chiral phosphorothioates, phosphotriesters, aminoalkylphosphotriesters, alkyl phosphonates, thionoalkylphosphonates, phosphinates, phosphoramidates, thionophosphoramidates, thionoalkylphosphotriesters, and boranophosphates and various salt forms thereof. See e.g., U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is incorporated herein by reference in its entirety.

Examples of the non-phosphorous containing backbones described above are disclosed in, e.g., U.S. Pat. Nos. 5,034,506; 5,185,444; 5,214,134; 5,216,141; 5,235,033; 5,264,562; 5,264,564; 5,405,938; 5,434,257; 5,470,967; 5,489,677; 5,541,307; 5,561,225; 5,596,086; 5,610,289; 5,602,240; 5,608,046; 5,610,289; 5,618,704; 5,623,070; 5,663,312; 5,677,437; and 5,677,439, each of which is incorporated herein by reference in its entirety.

Modified forms of siRNA compounds can also contain modified nucleosides (nucleoside analogs), i.e., modified purine or pyrimidine bases, e.g., 5-substituted pyrimidines, 6-azapyrimidines, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), 2-thiouridine, 4-thiouridine, 5-(carboxyhydroxymethyl)uridine, 5'-carboxymethylaminomethyl-2-thiouridine, 5-carboxymethylaminomethyluridine, 5-methoxyaminomethyl-2-thiouridine, 5-methylaminomethyluridine, 5-methylcarbonylmethyluridine, 5-methyloxyuridine, 5-methyl-2-thiouridine, 4-acetylcytidine, 3-methylcytidine, propyne, quesosine, wybutosine, wybutoxosine, beta-D-galactosylqueosine, N-2, N-6 and O-substituted purines, inosine, 1-methyladenosine, 1-methylinosine, 2,2-dimethylguanosine, 2-methyladenosine, 2-methylguanosine, N6-methyladenosine, 7-methylguanosine, 2-methylthio-N6-isopentenyladenosine, beta-D-mannosylqueosine, uridine-5-oxyacetic acid, 2-thiocytidine, threonine derivatives, and the like. See e.g., U.S. Pat. Nos. 3,687,808; 4,845,205; 5,130,302; 5,175,273; 5,367,066; 5,432,272; 5,459,255; 5,484,908; 5,502,177; 5,525,711; 5,587,469; 5,594,121; 5,596,091; 5,681,941; and 5,750,692, PCT Publication No. WO 92/07065; PCT Publication No. WO 93/15187; and Limbach et al., *Nucleic Acids Res.,* 22:2183 (1994), each of which is incorporated herein by reference in its entirety.

In addition, modified siRNA compounds can also have substituted or modified sugar moieties, e.g., 2'-O-methoxyethyl sugar moieties. See e.g., U.S. Pat. Nos. 4,981,957; 5,118,800; 5,319,080; 5,393,878; 5,446,137; 5,466,786; 5,514,785; 5,567,811; 5,576,427; 5,591,722; 5,610,300; 5,627,053; 5,639,873; 5,646,265; 5,658,873; 5,670,633; and 5,700,920, each of which is incorporated herein by reference in its entirety.

Modified siRNA compounds may be synthesized by the methods disclosed in, e.g., U.S. Pat. No. 5,652,094; International Publication Nos. WO 91/03162; WO 92/07065 and WO 93/15187; European Patent Application No. 92110298.4; Perrault et al., *Nature,* 344:565 (1990); Pieken et al., *Science,* 253:314 (1991); and Usman and Cedergren, *Trends in Biochem. Sci.,* 17:334 (1992), each of which is incorporated herein by reference in its entirety.

Preferably, the 3' overhangs of the siRNAs of the present invention are modified to provide resistance to cellular nucleases. In one embodiment the 3' overhangs comprise 2'-deoxyribonucleotides. In a preferred embodiment (depicted in FIG. 1) these 3' overhangs comprise a dinucleotide made of two 2'-deoxythymidine residues (i.e., dTdT) linked by a 5'-3' phosphodiester linkage.

As mentioned above, in some cases specific modifications are made to the nucleic acids that are to be delivered in order to improve their therapeutic characteristics. Examples of the modifications made to the nucleic acids in order to improve “bioavailablility” are taught in PCT Patent Application Publications WO 98/49348, WO 2004/029075 and WO 2004/065579, in U.S. Pat. Nos. 6,153,737 and 6,395,492, and in U.S. Patent Application Publications 2002/0188101 and 2003/0064492. Examples of modifications made to the nucleic acids to produce “long-circulating liposomal compositions are taught in PCT Patent Application Publication WO 99/59547. Methods of using such modified oligonucleotides in formulations for hepatic delivery are taught in PCT Patent Application Publication WO 03/072711. Similarly, compositions and methods of using modified oligonucleotides for topical delivery are taught in PCT Patent Application Publication WO 99/60617. Also, compositions and methods of using modified oligonucleotides for pulmonary delivery are taught in PCT Patent Application Publication WO 99/60010 and WO 99/60166, and in U.S. Patent Application Publications 2003/0157030 and 2004/0063654. And, compositions and methods of using modified oligonucleotides for delivery via the alimentary canal are taught in PCT Patent Application Publication WO 99/01579 and WO 99/60012, as well as in U.S. Pat. No. 6,747,014, with the latter two publications specifically teaching methods for rectal administration of therapeutic nucleic acids. All of these aforementioned patent applications and published patents teaching methods for improved uptake and delivery of therapeutic nucleic acids and modified oligonucleotides are incorporated herein by reference in their entirety.

siRNA compounds may be administered to mammals by various methods through different routes. For example, they can be administered by intravenous injection. See Song et al., *Nature Medicine,* 9:347-351 (2003). They can also be delivered directly to a particular organ or tissue by any suitable localized administration methods. Several other approaches for delivery of siRNA into animals have also proved to be successful. See e.g., McCaffery et al., *Nature,* 418:38-39 (2002); Lewis et al., *Nature Genetics,* 32:107-108 (2002); and Xia et al., *Nature Biotech.,* 20:1006-1010 (2002). Alternatively, they may be delivered encapsulated in liposomes, by iontophoresis, or by incorporation into other vehicles such as hydrogels, cyclodextrins, biodegradable nanocapsules, and bioadhesive microspheres.

A particularly preferred method of in vivo delivery of siRNA, shRNAs or enzymatic nucleic acids is the process of lipofection. In lipofection, cationic lipids are used to promote encapsulation of negatively charged nucleic acids into liposomes, and the cationic lipids on the surface of the liposomes facilitate fusion of the liposomes with negatively charged bi-layer cell membranes (Yanagihara et al., *Mol. Cell. Biol. Hum. Dis. Ser.* 5:64-82 (1995); and Felgner and Ringold, *Science* 337:387-388 (1989)). Improvements in the lipids used to prepare liposomes have been made and synthetic cationic lipids specifically designed to limit the difficulties and complications encountered with liposome-mediated transfection in vivo can be used to prepare liposomes for in-vivo delivery (Templeton, *Biosci. Rep.* 22:283-295 (2002); Katsel and Greenstein, Biotechnol. *Annu. Rev.* 5:197-220 (2000)). Such compositions and methods have been described in the following publications, which are all incorporated, each of which is incorporated herein by reference in its entirety: Felgner et al., *Proc. Natl. Acad. Sci.* USA 84:7413-7417 (1987); Mackey et al., *Proc. Natl. Acad. Sci.* USA 85:8027-8031 (1988); Ulmer et al., *Science* 259: 1745-1748 (1992); Yamazaki et al., *Gene Ther.* 7:1148-1155 (2000); Oku et al., *Adv. Drug Deliv. Rev.* 52:209-218 (2001) and Matsuura et al., *Biochem. Biophys. Acta* 1612:136-143 (2003). Compounds and compositions that are particularly useful in the preparation of liposomes, and in the liposome-mediated transfection of cells are described in Matsuura et al., *Biochem. Biophys. Acta* 1612:136-143 (2003), international patent publications WO 95/18863 and WO 96/17823, as well as U.S. Pat. Nos. 5,169,636, 5,459,127, 5,651,981, 5,661,018, 5,686,620, 5,688,958, 5,695,780, 5,780,053, 5,855,910, 5,891,714, 6,187,760 and 6,316,260, which are incorporated herein by reference in their entirety. Particularly preferred compositions and methods for use in delivering siRNAs to mammalian cells are described in U.S. Patent Application Publication Nos. 2002/0165183, 2003/0073640, 2003/0125281, and 2003/0143204 which are also incorporated herein by reference in their entirety.

Also as mentioned above, recent advances in methods and pharmaceutical formulations for the delivery of therapeutic nucleic acids into the tissues of mammals, have been reported. For example, the use of cationic liposomes to facilitate the uptake of siRNAs by a variety of tissues in mice, were described by Sorensen and coworkers (Sorensen, et al. J. Mol. Biol 327:761-766 (2003)), which is incorporated herein by reference in its entirety.

In addition, siRNAs may also be delivered by a gene therapy approach, using a DNA vector from which siRNA precursors, e.g., small hairpin form (shRNA), can be transcribed directly. Recent studies have demonstrated that while siRNAs, which are double-stranded, are very effective at mediating RNAi, short, single-stranded, hairpin-shaped RNAs (shRNAs) can also mediate RNAi, presumably because they fold into intramolecular duplexes that are processed into double-stranded siRNAs by cellular enzymes. See Sui et al., *Proc. Natl. Acad. Sci. U.S.A.,* 99:5515-5520 (2002); Yu et al., *Proc. Natl. Acad. Sci. U.S.A.,* 99:6047-6052 (2002); and Paul et al., *Nature Biotech.,* 20:505-508 (2002)). This discovery has significant and far-reaching implications, since the production of such shRNAs can be readily achieved in vivo by transfecting cells with DNA vectors bearing short inverted repeats separated by a small number of (e.g., 3 to 9) nucleotides that direct the transcription of such shRNAs. Additionally, if mechanisms are included to direct the integration of the transcription cassette into the host cell genome, or to ensure the stability of the transcription vector, the RNAi caused by the encoded shRNAs, can be made stable and/or heritable. Not only have such techniques been used to “knock down” the expression of specific genes in mammalian cells, but also they have now been successfully employed to knock down the expression of exogenously expressed transgenes, as well as endogenous genes in the brain and liver of living mice. See generally Hannon, *Nature.* 418:244-251 (2002) and Shi, *Trends Genet.,* 19:9-12 (2003); see also Xia et al., *Nature Biotech.,* 20:1006-1010 (2002).

Such an approach was recently taken by Pardridge and coworkers, who reported the delivery of siRNAs into specific cells within the brains of rats. Their methods are described in two publications: Zhang et al., *J. Gene Med.* 5:1039-1045 (2003) and Zhang et al., *Clin Cancer Res.* 10:3667-3677 (2004)), which are both incorporated herein by reference in their entirety. In both of these studies, shRNA expression plasmids were encapsulated into 85 nm pegylated immunoliposomes, which were studded with monoclonal antibodies selected to interact with specific cellular receptors. Interactions between the monoclonal antibodies on the surface of the immunoliposomes facilitated their uptake across the blood-brain barrier and into cancer cells within the brains of the mice. Once inside the cells, the expression plasmids directed the expression of shRNAs, which activated RNAi within the cells inside of the brains of the treated mice.

Additional detailed methods for the intracellular expression and delivery of siRNAs and shRNAs in mammalian cells are provided in U.S. Patent Application Publication 2003/0148519 by Engelke et al., and in publications by Paul et al. (*Nat. Biotechnol.* 20:505-508 (2002) and *Mol. Ther.* 7:237-247 (2003)), all of which are incorporated herein by reference in their entirety.

Accordingly, the instant invention provides shRNAs designed to induce the degradation of RNA transcripts encoding ROCK-II (FIG. 2). Such shRNAs can be synthesized exogenously and delivered into cells, tissues or a patient, or can be synthesized endogenously from an expression cassette or expression vector introduced into cells. Means for the introduction of either shRNAs synthesized exogenously are known in the art and discussed below. Means for the introduction of expression cassettes or expression vectors for the endogenous synthesis of shRNAs are also known in the art and are discussed below.

In the methods provided by the instant invention, the siRNAs presented in FIG. 1, and the shRNAs presented in FIG. 2, have been specifically designed to target RNA transcripts encoding ROCK-II, and to not target transcripts encoding ROCK-I. This is important because although ROCK-II is an isozyme of ROCK-I, and the two proteins share significant regions of similarity, it is desirable to specifically decrease the cellular concentrations of ROCK-II without affecting a parallel decrease in the cellular concentrations of ROCK-I.

Besides the siRNA compounds provided in FIG. 1, and the shRNA compounds provided in FIG. 2, additional siRNA compounds targeted to different sites within RNA transcripts encoding ROCK-II may also be designed and synthesized according to general guidelines provided herein and generally known to skilled artisans. See e.g., Elbashir, et al. (*Nature* 411: 494-498 (2001)). For example, such guidelines have been compiled into "The siRNA User Guide" which is available at Rockefeller University's Tuschl Lab RNA Molecular Biology website.

Using such guidelines, 47 target sequences have been identified within the coding region of human ROCK-II mRNA (Table 1). These 47 target sequences, which are provided by SEQ ID NOs:3-49, include the 12 preferred sequences for which siRNAs (FIG. 1) and shRNAs (FIG. 2) were designed. Importantly, these target sequences represent targets unique to ROCK-II, having optimal G/C contents, and lacking nucleotide triplets or quadruplets (e.g., GGG, CCC, GGGG & CCCC). As shown in Example 1, below, three of these siRNAs (siRNAs #1, #3, and #10 in FIG. 1), which were specifically designed to correspond to the target sequences provided by SEQ ID NOs:3, 11, and 29, provoke a decrease in ROCK-II expression when introduced by lipofection into human cells in culture.

TABLE 1

ROCK-II-Specific siRNA Target Sequences

| SEQ ID NO: | Target Sequence | Position* | G/C Content |
|---|---|---|---|
| 3 | GUGCAGUUGGUUCGUCACA | 770 | 52.63% |
| 4 | CAAGGCAUCGCAGAAGGUU | 787 | 52.63% |
| 5 | UAGGUAUCUGUACAUGGUA | 940 | 36.84% |
| 6 | GGUAUCUGUACAUGGUAAU | 942 | 36.84% |
| 7 | AACAGGCAUGGUACAUUGU | 1177 | 42.11% |
| 8 | ACACCGGAUUAUAUAUCAC | 1211 | 36.84% |
| 9 | UGCGGAUUCACUUGUAGGA | 1339 | 47.37% |
| 10 | CUCAGCAGUGACAUAGACA | 1577 | 47.37% |
| 11 | GUGACUCUCCAUCUUGUAG | 1722 | 47.37% |
| 12 | GAAGAGGAGAUUACCUUAC | 1907 | 42.11% |
| 13 | AAGUGUGGAAUCAGCAUUA | 1930 | 36.84% |
| 14 | AGUGUGGAAUCAGCAUUAA | 1931 | 36.84% |
| 15 | GCAGCUGGAAUCUAACAAU | 2233 | 42.11% |
| 16 | GCUGAACAUAAGGCCACAA | 2570 | 47.37% |
| 17 | AGGCACGACUAGCAGAUAA | 2589 | 47.37% |
| 18 | AGAUCUAUGAGUCCAUCGA | 2613 | 42.11% |
| 19 | GAUCUAUGAGUCCAUCGAA | 2614 | 42.11% |
| 20 | AAGUGGAGAACCUAUUGCU | 2700 | 42.11% |
| 21 | CACAACAGGUUAACACACU | 2895 | 42.11% |
| 22 | CAACAGGUUAACACACUAA | 2897 | 36.84% |

TABLE 1-continued

ROCK-II-Specific siRNA Target Sequences

| SEQ ID NO: | Target Sequence | Position* | G/C Content |
|---|---|---|---|
| 23 | GCUCGAAGCAGAACAGUAU | 3049 | 47.37% |
| 24 | CUAAUAGGACACUAACUAG | 3375 | 36.84% |
| 25 | AUAAGCGCAGCAGCUAUUA | 3485 | 42.11% |
| 26 | UAAGCGCAGCAGCUAUUAA | 3486 | 42.11% |
| 27 | ACUCAAGCUGUGAAUAAGU | 3548 | 36.84% |
| 28 | CUCAAGCUGUGAAUAAGUU | 3549 | 36.84% |
| 29 | GAACCUGUCAAGCGUGGUA | 3590 | 52.63% |
| 30 | ACCUGUCAAGCGUGGUAAU | 3592 | 47.37% |
| 31 | AGAGAGCCAGAUUCGAAUU | 3745 | 42.11% |
| 32 | GAGAGCCAGAUUCGAAUUG | 3746 | 47.37% |
| 33 | GCCAGAUUCGAAUUGAACU | 3750 | 42.11% |
| 34 | UUCGAAUUGAACUGCAGAU | 3756 | 36.84% |
| 35 | ACCAACUGUGAGGCUUGUA | 4268 | 47.37% |
| 36 | ACUGUGAGGCUUGUAUGAA | 4272 | 42.11% |
| 37 | CUGUGAGGCUUGUAUGAAG | 4273 | 47.37% |
| 38 | UUCAAGGUGAUCGUAUUCU | 4647 | 36.84% |
| 39 | GACUGAUACAUACACUCAU | 4731 | 36.84% |
| 40 | UUGGUUGAUAGACUAAGGA | 4831 | 36.84% |
| 41 | CUAAGGAUAUAUGCAACUC | 4843 | 36.84% |
| 42 | AGGAUAUAUGCAACUCUUC | 4846 | 36.84% |
| 43 | AGUGACCAUUAUACUGUGU | 5046 | 36.84% |
| 44 | GUGACCAUUAUACUGUGUA | 5047 | 36.84% |
| 45 | CCUGAUGGAAGUUGCAUGU | 5248 | 47.37% |
| 46 | GACCUCAGUAUUAGUCUGU | 5620 | 42.11% |
| 47 | GGACAUUCUUGCCGUAUUC | 5941 | 47.37% |
| 48 | ACAAUAUGCAGCAAUGGUA | 5995 | 36.84% |
| 49 | CUCCGUCUCUACCAAUAUA | 6236 | 42.11% |

*Refers to the nucleotide position in the coding sequence of ROCK-II encoding transcripts (SEQ ID NO:2) to which the 5' most nucleotide in the target sequence corresponds.

Enzymatic Nucleic Acid Therapy:

In another embodiment, an enzymatic nucleic acid is provided, which is designed to target and cleave RNA transcripts encoding ROCK-II in a nucleotide base sequence specific manner. One class of enzymatic nucleic acids is ribozymes, which are RNA molecules capable of repeatedly cleaving other RNA molecules into two or more pieces in a nucleotide base sequence specific manner. See Kim et al., *Proc. Natl. Acad. of Sci. USA,* 84:8788 (1987); Haseloff and Gerlach, *Nature,* 334:585 (1988); and Jefferies et al., *Nucleic Acid Res.,* 17:1371 (1989). Such enzymatic nucleic acids typically have two functional domains: a catalytic domain and a binding sequence that guides the binding of the enzymatic nucleic acid to a target RNA through complementary base pairing. Once a specifically designed enzymatic nucleic acid is bound to a target RNA, it enzymatically cleaves the target RNA, typically reducing its stability and destroying its ability to direct translation of an encoded protein. After an enzymatic nucleic acid has cleaved its RNA target, it is released from that target RNA and thereafter can bind and cleave another target. That is, a single enzymatic nucleic acid molecule can repeatedly bind and cleave new targets. Therefore, one advantage of enzymatic nucleic acid treatment is that a lower amount of exogenous enzymatic nucleic acid is required as compared to conventional antisense oligonucleotide therapies. In addition, enzymatic nucleic acids generally exhibit less affinity to RNA targets than DNA-based antisense oligonucleotides, and therefore are less prone to bind to unintended targets.

The enzymatic nucleic acid molecules of the present invention are provided such that, when introduced into cells, they result in the reduction of RNA transcripts encoding ROCK-II by at least a 10%, 20%, 30%, or greater reduction in cellular ROCK-II mRNA levels, and/or a 10%, 20%, 30%, or greater reduction in cellular ROCK-II protein levels. Preferably such enzymatic nucleic acid molecules reduce ROCK-II mRNA and/or ROCK-II protein levels by 40%, 50%, 60%, or more. More preferably such enzymatic nucleic acid molecules reduce ROCK-II mRNA and/or ROCK-II protein levels by 70%, 75%, 80%, 85%, 90%, 95% or more.

Unlike siRNAs and shRNAs, which apparently only induce the degradation of mature, spliced mRNAs that have been and exported to the cytoplasm, enzymatic nucleic acids can catalyze the cleavage of nascent RNA transcripts, or pre-mRNAs (not-yet spliced or polyadenylated mRNAs), within the nucleus (See Vickers, et al., *J. Biol. Chem.* 278:7108-7118 (2003)). The ability to cleave pre-mRNAs within the nucleus conveys certain advantages to enzymatic nucleic acids over siRNAs and shRNAs targeted to mature mRNAs encoding the same gene product. Specifically, enzymatic nucleic acids designed to cleave a particular pre-mRNAs can induce the degradation of all splice forms of that transcript, leading to the knockdown of expression of all splice-variants of that gene product. Additionally, because enzymatic nucleic acids can be designed to cleave pre-mRNAs in regions corresponding to introns, as well as regions corresponding to exons, there are more potential sequences to which enzymatic nucleic acids can be targeted—as compared to siRNAs and shRNAs—to induce cleavage of RNA transcripts encoding ROCK-II.

As with siRNAs and shRNAs, enzymatic nucleic acids can be designed to target sequences present in regions corresponding to specific exons. In this manner, enzymatic nucleic acids can induce the degradation of particular splice forms of mRNAs that bear the targeted exon, while not affecting the cellular concentrations of other splice forms lacking the targeted exon. Also, like siRNAs and shRNAs, enzymatic nucleic acids can be designed to target transcripts encoding specific isoforms of closely related protein families, by targeting them to the more-diverged sequences present in regions of pre-mRNAs corresponding to introns.

In accordance with the present invention, an enzymatic nucleic acid may target any portion of the RNA transcripts encoding ROCK-II. Methods for selecting an enzymatic nucleic acids target sequence and designing and making enzymatic nucleic acids are generally known in the art. See e.g., U.S. Pat. Nos. 4,987,071; 5,496,698; 5,525,468; 5,631,359; 5,646,020; 5,672,511; and 6,140,491, each of which is incorporated herein by reference in its entirety. For example, suitable enzymatic nucleic acids may be designed in various configurations such as hammerhead motifs, hairpin motifs, hepatitis delta virus motifs, group I intron motifs, or RNase P RNA motifs. See e.g., U.S. Pat. Nos. 4,987,071; 5,496,698; 5,525,468; 5,631,359; 5,646,020; 5,672,511; and 6,140,491; Rossi et al., *AIDS Res. Human Retroviruses* 8:183 (1992); Hampel and Tritz, *Biochemistry* 28:4929 (1989); Hampel et al., *Nucleic Acids Res.,* 18:299 (1990); Perrotta and Been, *Biochemistry* 31:16 (1992); and Guerrier-Takada et al., *Cell,* 35:849 (1983), all of which are incorporated herein by reference in their entirety.

Enzymatic nucleic acids can be synthesized by the same methods used for normal nucleic acid synthesis. For example, such methods are disclosed in Usman et al., *J. Am. Chem. Soc.,* 109:7845-7854 (1987) and Scaringe et al., *Nucleic Acids Res.,* 18:5433-5441 (1990). Modified enzymatic nucleic acids may be synthesized by the methods disclosed in, e.g., U.S. Pat. No. 5,652,094; International Publication Nos. WO 91/03162; WO 92/07065 and WO 93/15187; European Patent Application No. 92110298.4; Perrault et al., *Nature,* 344:565 (1990); Pieken et al., *Science,* 253:314 (1991); and Usman and Cedergren, *Trends in Biochem. Sci.,* 17:334 (1992), all of which are incorporated herein by reference in their entirety.

As used herein, "modified equivalent" means a modified form of a particular enzymatic nucleic acid compound having the same target-specificity (i.e., recognizing the same mRNA molecules that complement the unmodified particular enzymatic nucleic acid compound). Thus, a modified equivalent of an unmodified enzymatic nucleic acid compound can have modified ribonucleotides or deoxyribonucleotides, that is, ribonucleotides or deoxyribonucleotides that contain a modification in the chemical structure of an unmodified nucleotide base, sugar and/or phosphate (or phosphodiester linkage). As is known in the art, an "unmodified ribonucleotides" has one of the bases adenine, cytosine, guanine, and uracil joined to the 1' carbon of beta-D-ribo-furanose. Similarly, "unmodified deoxyribonucleotides" has one of the bases adenine, cytosine, guanine, and thymine joined to the 1' carbon of beta-D-2'-deoxy-ribo-furanose.

Preferably, modified enzymatic nucleic acid compounds contain modified backbones or non-natural internucleoside linkages, e.g., modified phosphorous-containing backbones and non-phosphorous backbones such as morpholino backbones; siloxane, sulfide, sulfoxide, sulfone, sulfonate, sulfonamide, and sulfamate backbones; formacetyl and thioformacetyl backbones; alkene-containing backbones; methyleneimino and methylenehydrazino backbones; amide backbones, and the like.

Examples of modified phosphorous-containing backbones include, but are not limited to phosphorothioates, phosphorodithioates, chiral phosphorothioates, phosphotriesters, aminoalkylphosphotriesters, alkyl phosphonates, thionoalkylphosphonates, phosphinates, phosphoramidates, thionophosphoramidates, thionoalkylphosphotriesters, and boranophosphates and various salt forms thereof. See e.g., U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is incorporated herein by reference in its entirety.

Examples of the non-phosphorous containing backbones described above are disclosed in, e.g., U.S. Pat. Nos. 5,034,506; 5,185,444; 5,214,134; 5,216,141; 5,235,033; 5,264,562; 5,264,564; 5,405,938; 5,434,257; 5,470,967; 5,489,677; 5,541,307; 5,561,225; 5,596,086; 5,610,289; 5,602,240; 5,608,046; 5,610,289; 5,618,704; 5,623,070; 5,663,312; 5,677,437; and 5,677,439, each of which is incorporated herein by reference in its entirety.

Modified forms of enzymatic nucleic acid compounds can also contain modified nucleosides (nucleoside analogs), i.e., modified purine or pyrimidine bases, e.g., 5-substituted pyrimidines, 6-azapyrimidines, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), 2-thiouridine, 4-thiouridine, 5-(carboxyhydroxymethyl)uridine, 5'-carboxymethylaminomethyl-2-thiouridine, 5-carboxymethylaminomethyluridine, 5-methoxyaminomethyl-2-thiouridine, 5-methylaminomethyluridine, 5-methylcarbonylmethyluridine, 5-methyloxyuridine, 5-methyl-2-thiouridine, 4-acetylcytidine, 3-methylcytidine, propyne, quesosine, wybutosine, wybutoxosine, beta-D-galactosylqueosine, N-2, N-6 and O-substituted purines, inosine, 1-methyladenosine, 1-methylinosine, 2,2-dimethylguanosine, 2-methyladenosine, 2-methylguanosine, N6-methyladenosine, 7-methylguanosine, 2-methylthio-N6-isopentenyladenosine, beta-D-mannosylqueosine, uridine-5-oxyacetic acid, 2-thiocytidine, threonine derivatives, and the like. See e.g., U.S. Pat. Nos. 3,687,808; 4,845,205; 5,130,302; 5,175,273; 5,367,066; 5,432,272; 5,459,255; 5,484,908; 5,502,177; 5,525,711; 5,587,469; 5,594,121; 5,596,091; 5,681,941; and 5,750,692, PCT Publication No. WO 92/07065; PCT Publication No. WO 93/15187; and Limbach et al., *Nucleic Acids Res.*, 22:2183 (1994), each of which is incorporated herein by reference in its entirety.

In addition, modified enzymatic nucleic acid compounds can also have substituted or modified sugar moieties, e.g., 2'-O-methoxyethyl sugar moieties. See e.g., U.S. Pat. Nos. 4,981,957; 5,118,800; 5,319,080; 5,393,878; 5,446,137; 5,466,786; 5,514,785; 5,567,811; 5,576,427; 5,591,722; 5,610,300; 5,627,053; 5,639,873; 5,646,265; 5,658,873; 5,670,633; and 5,700,920, each of which is incorporated herein by reference in its entirety.

Modified enzymatic nucleic acid compounds may be synthesized by the methods disclosed in, e.g., U.S. Pat. No. 5,652,094; International Publication Nos. WO 91/03162; WO 92/07065 and WO 93/15187; European Patent Application No. 92110298.4; Perrault et al., *Nature*, 344:565 (1990); Pieken et al., *Science*, 253:314 (1991); and Usman and Cedergren, *Trends in Biochem. Sci.*, 17:334 (1992), each of which is incorporated herein by reference in its entirety.

Enzymatic nucleic acids of the present invention may be administered to cells by any known methods, e.g., disclosed in International Publication No. WO 94/02595, which is incorporated herein by reference in its entirety. For example, they can be administered directly to cells or tissue in vitro or in a patient through any suitable route, e.g., intravenous injection. Alternatively, they may be delivered encapsulated in liposomes, by iontophoresis, or by incorporation into other vehicles such as hydrogels, cyclodextrins, biodegradable nanocapsules, and bioadhesive microspheres. In addition, they may also be delivered by a gene therapy approach, using a DNA vector from which enzymatic RNAs can be transcribed directly. Suitable gene therapy approaches and methods are disclosed in detail below.

Antisense Therapy:

The RNase-H activating antisense oligonucleotide molecules of the present invention are provided such that, when introduced into cells, they result in the reduction of RNA transcripts encoding ROCK-II by at least a 10%, 20%, 30%, or greater reduction in cellular ROCK-II mRNA levels, and/or a 10%, 20%, 30%, or greater reduction in cellular ROCK-II protein levels. Preferably such RNase-H activating antisense oligonucleotides reduce ROCK-II mRNA and/or ROCK-II protein levels by 40%, 50%, 60%, or more. More preferably such RNase-H activating antisense oligonucleotides reduce ROCK-II mRNA and/or ROCK-II protein levels by 70%, 75%, 80%, 85%, 90%, 95% or more.

As with siRNAs, shRNAs, and enzymatic nucleic acids, RNase H activating antisense oligonucleotides can be designed to target accessible sequences present in regions corresponding to specific exons. In this manner, RNase H activating antisense oligonucleotides can induce the degradation of particular splice forms of mRNAs that bear the targeted exon, while not affecting the cellular concentrations of other splice forms lacking the targeted exon. Also, like siRNAs, shRNAs, and enzymatic nucleic acids, RNase H activating antisense oligonucleotides can be designed to target transcripts encoding specific isoforms of closely related protein families, by targeting them to the more-diverged sequences present in regions of pre-mRNAs corresponding to introns.

In accordance with the present invention, an RNase H activating antisense oligonucleotide may target any accessible portion of the RNA transcripts encoding ROCK-II. Methods for selecting an RNase H activating antisense oligonucleotide target sequence and designing and making an RNase H activating antisense oligonucleotide are generally known in the art. See e.g., U.S. Patent Application Publication No. 2003/0148519, which is incorporated herein by reference in its entirety.

RNase H activating antisense oligonucleotides acids can be synthesized by the same methods used for normal nucleic acid synthesis. For example, such methods are disclosed in Usman et al., *J. Am. Chem. Soc.*, 109:7845-7854 (1987) and Scaringe et al., *Nucleic Acids Res.*, 18:5433-5441 (1990). Modified enzymatic nucleic acids may be synthesized by the methods disclosed in, e.g., U.S. Pat. No. 5,652,094; International Publication Nos. WO 91/03162; WO 92/07065 and WO 93/15187; European Patent Application No. 92110298.4; Perrault et al., *Nature*, 344:565 (1990); Pieken et al., *Science*, 253:314 (1991); and Usman and Cedergren, *Trends in Biochem. Sci.*, 17:334 (1992), all of which are incorporated herein by reference in their entirety.

As used herein, "modified equivalent" means a modified form of a particular RNase H activating antisense oligonucleotide compound having the same target-specificity (i.e., recognizing the same mRNA molecules that complement the unmodified particular enzymatic nucleic acid compound). Thus, a modified equivalent of an unmodified RNase H activating antisense oligonucleotide compound can have modified deoxyribonucleotides, that is, deoxyribonucleotides that contain a modification in the chemical structure of an unmodified nucleotide base, sugar and/or phosphate (or phosphodiester linkage). As is known in the art, an "unmodified deoxyribonucleotides" has one of the bases adenine, cytosine, guanine, and thymine joined to the 1' carbon of -beta-D-2'-deoxy-ribo-furanose.

Preferably, modified RNase H activating antisense oligonucleotide compounds contain modified backbones or non-natural internucleoside linkages, e.g., modified phosphorous-containing backbones and non-phosphorous backbones such as morpholino backbones; siloxane, sulfide, sulfoxide, sulfone, sulfonate, sulfonamide, and sulfamate backbones; formacetyl and thioformacetyl backbones; alkene-containing backbones; methyleneimino and methylenehydrazino backbones; amide backbones, and the like.

Examples of modified phosphorous-containing backbones include, but are not limited to phosphorothioates, phosphorodithioates, chiral phosphorothioates, phosphotriesters, aminoalkylphosphotriesters, alkyl phosphonates, thionoalkylphosphonates, phosphinates, phosphoramidates, thionophosphoramidates, thionoalkylphosphotriesters, and boranophosphates and various salt forms thereof. See e.g., U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is incorporated herein by reference in its entirety.

Examples of the non-phosphorous containing backbones described above are disclosed in, e.g., U.S. Pat. Nos. 5,034,506; 5,185,444; 5,214,134; 5,216,141; 5,235,033; 5,264,562; 5,264,564; 5,405,938; 5,434,257; 5,470,967; 5,489,677; 5,541,307; 5,561,225; 5,596,086; 5,610,289; 5,602, 240; 5,608,046; 5,610,289; 5,618,704; 5,623,070; 5,663,312; 5,677,437; and 5,677,439, each of which is incorporated herein by reference in its entirety.

Modified forms of RNase H activating antisense oligonucleotide compounds can also contain modified nucleosides (nucleoside analogs), i.e., modified purine or pyrimidine bases, e.g., 5-substituted pyrimidines, 6-azapyrimidines, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), 2-thiouridine, 4-thiouridine, 5-(carboxyhydroxymethyl)uridine, 5'-carboxymethylaminomethyl-2-thiouridine, 5-carboxymethylaminomethyluridine, 5-methoxyaminomethyl-2-thiouridine, 5-methylaminomethyluridine, 5-methylcarbonylmethyluridine, 5-methyloxyuridine, 5-methyl-2-thiouridine, 4-acetylcytidine, 3-methylcytidine, propyne, quesosine, wybutosine, wybutoxosine, beta-D-galactosylqueosine, N-2, N-6 and O-substituted purines, inosine, 1-methyladenosine, 1-methylinosine, 2,2-dimethylguanosine, 2-methyladenosine, 2-methylguanosine, N6-methyladenosine, 7-methylguanosine, 2-methylthio-N6-isopentenyladenosine, beta-D-mannosylqueosine, uridine-5-oxyacetic acid, 2-thiocytidine, threonine derivatives, and the like. See e.g., U.S. Pat. Nos. 3,687,808; 4,845,205; 5,130,302; 5,175,273; 5,367,066; 5,432,272; 5,459,255; 5,484,908; 5,502,177; 5,525,711; 5,587,469; 5,594,121; 5,596,091; 5,681,941; and 5,750,692, PCT Publication No. WO 92/07065; PCT Publication No. WO 93/15187; and Limbach et al., *Nucleic Acids Res.,* 22:2183 (1994), each of which is incorporated herein by reference in its entirety.

In addition, modified RNase H activating antisense oligonucleotide compounds can also have substituted or modified sugar moieties, e.g., 2'-O-methoxyethyl sugar moieties. See e.g., U.S. Pat. Nos. 4,981,957; 5,118,800; 5,319,080; 5,393,878; 5,446,137; 5,466,786; 5,514,785; 5,567,811; 5,576,427; 5,591,722; 5,610,300; 5,627,053; 5,639,873; 5,646,265; 5,658,873; 5,670,633; and 5,700,920, each of which is incorporated herein by reference in its entirety.

Modified RNase H activating antisense oligonucleotide compounds may be synthesized by the methods disclosed in, e.g., U.S. Pat. No. 5,652,094; International Publication Nos. WO 91/03162; WO 92/07065 and WO 93/15187; European Patent Application No. 92110298.4; Perrault et al., *Nature,* 344:565 (1990); Pieken et al., *Science,* 253:314 (1991); and Usman and Cedergren, *Trends in Biochem. Sci.,* 17:334 (1992), each of which is incorporated herein by reference in its entirety each of which is incorporated herein by reference in its entirety.

RNase H activating antisense oligonucleotides of the present invention may be administered to cells by any known methods, e.g., disclosed in International Publication No. WO 94/02595. For example, they can be administered directly to cells or tissue in vitro or in a patient through any suitable route, e.g., intravenous injection. Alternatively, they may be delivered encapsulated in liposomes, by iontophoresis, or by incorporation into other vehicles such as hydrogels, cyclodextrins, biodegradable nanocapsules, and bioadhesive microspheres.

Gene Therapy:

In another embodiment of the present invention, the concentration of ROCK-II is decreased in patients, tissues or cells by endogenously producing a nucleic acid that induces the degradation of RNA transcripts encoding ROCK-II or otherwise results in a specific reduction in cellular levels of ROCK-II. In this embodiment, the nucleic acids that induce degradation of RNA transcripts encoding ROCK-II or otherwise results in a specific reduction in cellular levels of ROCK-II, are preferably RNA molecules that are transcribed within cells. For example, nucleic acid template molecules encoding an RNA molecule that induces the degradation of RNA transcripts encoding ROCK-II are introduced into patients, tissue, or cells, and are used to direct the expression of such an RNA molecule(s) by exploiting the transcriptional machinery of the cell.

Various gene therapy methods are well known in the art, and successes in gene therapy have been reported recently. See e.g., Kay et al., *Nature Genet.,* 24:257-61 (2000); Cavazzana-Calvo et al., *Science,* 288:669 (2000); and Blaese et al., *Science,* 270: 475 (1995); Kantoff, et al., J. Exp. Med. 166:219 (1987).

Any suitable gene therapy methods may be used for the purposes of the present invention, however, preferred methods are provided by U.S. Patent Application Publication 2003/0148519. Generally, a nucleic acid encoding an RNA molecule according to the present invention, and capable of inducing the degradation of RNA transcripts encoding ROCK-II, or otherwise specifically reducing cellular concentrations of ROCK-II, is incorporated into a suitable expression cassette or vector and is operably linked to a promoter in the cassette or vector. Suitable promoters may be constitutive or inducible, and may be tissue or organ specific, or specific to a particular phase of development. Preferably, the promoter is positioned 5' to the transcribed region. Suitable promoters include but are not limited to viral transcription promoters derived from adenovirus, simian virus 40 (SV40) (e.g., the early and late promoters of SV40), Rous sarcoma virus (RSV), and cytomegalovirus (CMV) (e.g., CMV immediate-early promoter), human immunodeficiency virus (HIV) (e.g., long terminal repeat (LTR)), vaccinia virus (e.g., 7.5K promoter), and herpes simplex virus (HSV) (e.g., thymidine kinase promoter). In one preferred embodiment the promoter is a U6 gene promoter. In another preferred embodiment the promoter is a promoter from a 7SL signal recognition particle RNA, or a 5S ribosomal RNA. In a highly preferred embodiment the promoter (for example, a U6 promoter) is modified so as to possess different specificity. As a non-limiting example, the U6 promoter is modified to a Tet-inducible promoter. In the Tet repressor, the presence of DNA-binding sites interferes with the initiation of transcription from the promoter. Thus, the presence of the Tet repressor at the TATA box, and other representative sequences, results in the U6 promoter being repressed, or turned off. Addition of tetracycline results in the release of the Tet repressor, and concomitant de-repression of the promoter. Hence, the addition of tetracycline results in the induction, or "turning on," of the modified promoter.

Other promoters are also contemplated and include other RNA polymerase III promoters, suitably modified as necessary. In addition to the U6 snRNA promoter, such promoters include tRNA, RNAse P RNA, and adenovirus VA RNA pol III promoters as described by Medina and Joshi (*Curr. Opin. Mol. Ther.* 1:580-594 (1999), Brummelcamp et al. (*Science* 296:550-553 (2002)), and McManus et al. (*RNA* 8:842-850 (2002)), the publications of which are all incorporated herein by reference in their entirety.

Where tissue-specific expression of the exogenous gene is desirable, tissue-specific promoters may be operably linked to the exogenous gene. In addition, selection markers may also be included in the vector for purposes of selecting, in vitro, those cells that contain the exogenous gene. Various selection markers known in the art may be used including, but not limited to, e.g., genes conferring resistance to neomycin, hygromycin, zeocin, and the like.

In another aspect of the present invention, DNA encoding the RNA molecule capable of inducing the degradation of RNA transcripts encoding ROCK-II is incorporated into a plasmid DNA vector. In one set of embodiments of the present invention, the compositions provided comprise a vector having at least one expression cassette directing the expression of an RNA molecule capable of inducing the degradation of RNA transcripts encoding ROCK-II. The vectors may also encode marker genes, reporter genes, genes for selection of transformants or transfectants, or other genes of interest. Such vectors may also include specific sequences that allow for the stable integration of the vector-encoded expression cassettes into the genomes of host cells.

In some embodiments of the present invention, the expression vectors contemplated include, but are not limited to, chromosomal, nonchromosomal or synthetic DNA sequences, such as derivatives of viral DNAs such as vaccinia, adenovirus, adeno-associated virus, fowl pox virus, pseudorabies and retroviruses. It is contemplated that any vector may be used as long as it is viable in the host cell, and adequately directs the expression an RNA molecule capable of inducing the degradation of RNA transcripts encoding ROCK-II. These criteria are sufficient for the vector to be used transiently transfect a host cell. However, vectors capable of replicating in the host cell, vectors that direct the stable integration of expression cassettes, or vectors that can otherwise be used to stably transfect host cells are also contemplated.

Many expression vectors that may be useful for the present invention are known to those of skill in the art, and many are commercially available, including, e.g., pSiren (BD Biosciences Clontech, Inc., Palo Alto, Calif., USA), pSilencer (Ambion, Inc., Austin, Tex., USA), pGE1 (Stratagene, Inc., La Jolla, Calif., USA), which are designed to direct the expression of shRNAs within host cells. In some preferred embodiments of the present invention, mammalian expression vectors comprise an origin of replication, suitable promoters and enhancers, as well as ribosome binding sites, polyadenylation sites, splice donor and acceptor sites, transcriptional termination sequences, and various 5' and 3' flanking non-transcribed sequences. Other exemplary vectors include, but are not limited to, the following eukaryotic expression vectors: pSG (Stratagene, Inc., La Jolla, Calif., USA), pWLNEO, pSV2CAT, pOG44, PXT1, pSVK3, pBPV, pMSG, and pSVL (Pharmacia, Inc., USA). Particularly preferred vectors include pG1Na, a retroviral vector derived from MoMuLV (Zhou et al., *Gene* 149:3-39 (1994)); pCWRSV, an Adenovirus vector (Chaterjee et al., *Science* 258:1485 (1992)); pTZ18U (BioRad, Inc., Hercules, Calif., USA); and the like.

As mentioned above, Pardridge and coworkers, reported the delivery of expression cassettes, in the form of expression vectors, directing the expression of shRNAs into specific cells within the brains of rats. Their methods are described in two publications: Zhang et al., *J. Gene Med.* 5:1039-1045 (2003) and Zhang et al., *Clin Cancer Res.* 10:3667-3677 (2004)), which are both incorporated herein by reference in their entirety. In both of these studies, shRNA expression plasmids were encapsulated into 85 nm pegylated immunoliposomes, which were studded with monoclonal antibodies selected to interact with specific cellular receptors. Interactions between the monoclonal antibodies on the surface of the immunoliposomes facilitated their uptake across the blood-brain barrier and into cancer cells within the brains of the mice. Once inside the cells, the expression plasmids directed the expression of shRNAs, which activated RNAi within the cells inside of the brains of the treated mice.

Various viral vectors may also be used. Typically, in a viral vector, the viral genome is engineered to eliminate the disease-causing capability of the virus, e.g., the ability to replicate in the host cells. The exogenous nucleic acid to be introduced into cells or tissue in vitro or in a patient may be incorporated into the engineered viral genome, e.g., by inserting it into a viral gene that is non-essential to the viral infectivity. Viral vectors are convenient to use as they can be easily introduced into cells, tissues and patients by way of infection. Once in the host cell, the recombinant virus typically is integrated into the genome of the host cell. In rare instances, the recombinant virus may also replicate and remain as extrachromosomal elements. Examples of preferred viral vectors that can be used to deliver one or more therapeutic nucleic acid molecules to cells or tissues are described in U.S. Patent Application Publication 2003/0138407, which is incorporated herein by reference in its entirety.

A large number of retroviral vectors have been developed for gene therapy. These include vectors derived from oncoretroviruses (e.g., MLV), lentiviruses (e.g., HIV and SIV) and other retroviruses. For example, gene therapy vectors have been developed based on murine leukemia virus (See, Cepko, et al., Cell, 37:1053-1062 (1984), Cone and Mulligan, *Proc. Natl. Acad. Sci. U.S.A.,* 81:6349-6353 (1984)), mouse mammary tumor virus (See, Salmons et al., *Biochem. Biophys. Res. Commun.,* 159:1191-1198 (1984)), gibbon ape leukemia virus (See, Miller et al., *J. Virology,* 65:2220-2224 (1991)), HIV, (See Shimada et al., *J. Clin. Invest.,* 88:1043-1047 (1991)), and avian retroviruses (See Cosset et al., *J. Virology,* 64:1070-1078 (1990)), each of which is incorporated herein by reference in its entirety. In addition, various retroviral vectors are also described in U.S. Pat. Nos. 6,168,916; 6,140,111; 6,096,534; 5,985,655; 5,911,983; 4,980,286; and 4,868,116, all of which are incorporated herein by reference in there entirety.

Adeno-associated virus (AAV) vectors have been successfully tested in clinical trials. See e.g., Kay et al., *Nature Genet.* 24:257-61 (2000). AAV is a naturally occurring defective virus that requires other viruses such as adenoviruses or herpes viruses as helper viruses. See Muzyczka, *Curr. Top. Microbiol. Immun.,* 158:97 (1992). A recombinant AAV virus useful as a gene therapy vector is disclosed in U.S. Pat. No. 6,153,436, which is incorporated herein by reference in its entirety.

Adenoviral vectors can also be useful for purposes of gene therapy in accordance with the present invention. For example, U.S. Pat. No. 6,001,816 discloses an adenoviral vector, which is used to deliver a leptin gene intravenously to a mammal to treat obesity. Other recombinant adenoviral vectors may also be used, which include those disclosed in U.S. Pat. Nos. 6,171,855; 6,140,087; 6,063,622; 6,033,908; and 5,932,210, and Rosenfeld et al., *Science,* 252:431-434 (1991); and Rosenfeld et al., *Cell,* 68:143-155 (1992).

Other useful viral vectors include recombinant hepatitis viral vectors (See, e.g., U.S. Pat. No. 5,981,274), and recombinant entomopox vectors (See, e.g., U.S. Pat. Nos. 5,721,352 and 5,753,258).

Other non-traditional vectors may also be used for purposes of this invention. For example, International Publication No. WO 94/18834 discloses a method of delivering DNA into mammalian cells by conjugating the DNA to be delivered with a polyelectrolyte to form a complex. The complex may be microinjected into or taken up by cells. Similarly, International Publication No. WO 02/094185 discloses conjugates and degradable linkers, including folate, galactose, galactosamine, N-acetyl galactosamine, PEG, phospholipids, peptides and human serum albumin derived conjugates of biologically active compounds such as siRNAs and ribozymes, which can be used to deliver the siRNAs, shRNAs and ribozymes of the present invention into the cells of a patient.

The exogenous gene fragment or plasmid DNA vector containing the exogenous gene may also be introduced into cells by way of receptor-mediated endocytosis. See e.g., U.S. Pat. No. 6,090,619; Wu and Wu, *J. Biol. Chem.,* 263:14621 (1988); Curiel et al., *Proc. Natl. Acad. Sci. USA,* 88:8850 (1991). For example, U.S. Pat. No. 6,083,741 discloses introducing an exogenous nucleic acid into mammalian cells by associating the nucleic acid to a polycation moiety (e.g., poly-L-lysine having 3-100 lysine residues), which is itself coupled to an integrin receptor-binding moiety (e.g., a cyclic peptide having the sequence Arg-Gly-Asp).

Alternatively, the exogenous nucleic acid or vectors containing it can also be delivered into cells via amphiphiles. See e.g., U.S. Pat. No. 6,071,890. Typically, the exogenous nucleic acid or a vector containing the nucleic acid forms a complex with the cationic amphiphile. Mammalian cells contacted with the complex can readily take it up.

The exogenous gene can be introduced into cells or tissue in vitro or in a patient for purposes of gene therapy by various methods known in the art. For example, the exogenous gene sequences alone or in a conjugated or complex form described above, or incorporated into viral or DNA vectors, may be administered directly by injection into an appropriate tissue or organ of a patient. Alternatively, catheters, or like devices, may be used to deliver exogenous gene sequences, complexes, or vectors into a target organ or tissue. Suitable catheters are disclosed in, e.g., U.S. Pat. Nos. 4,186,745; 5,397,307; 5,547,472; 5,674,192; and 6,129,705, all of which are incorporated herein by reference in their entirety.

In addition, the exogenous gene or vectors containing the gene can be introduced into isolated cells using any known techniques such as calcium phosphate precipitation, microinjection, lipofection, electroporation, biolystics, receptor-mediated endocytosis, and the like. Cells expressing the exogenous gene may be selected and redelivered back to the patient by, e.g., injection or cell transplantation. The appropriate amount of cells delivered to a patient will vary with patient conditions, and desired effect, which can be determined by a skilled artisan. See e.g., U.S. Pat. Nos. 6,054,288; 6,048,524; and 6,048,729. Preferably, the cells used are autologous, i.e., cells obtained from the patient being treated.

Cell and Animal Models

In another aspect of the present invention, cell and animal models are provided in which ROCK-II activity, when compared with wild type cells or animals, is reduced by the action of a nucleic acid molecule designed to induce the degradation of RNA transcripts encoding ROCK-II. Such cell and animal models are useful tools for studying cellular functions and biological processes associated with ROCK-II. Such cell and animal models are also useful tools for studying the role played by ROCK-II in viral lifecycles and viral infection, and for testing various methods for modulating cellular functions, and for treating the diseases and disorders, associated with viral infections.

Cell Models:

Cell models comprising a nucleic acid molecule of the present invention that induces the degradation of RNA transcripts encoding ROCK-II, or otherwise results in a specific reduction in cellular levels of ROCK-II, are provided in accordance with the present invention.

The cell models may be established by manipulating any type of cell is such a way as to cause the cell to express an RNA molecule of the present invention that induces the degradation of RNA transcripts encoding ROCK-II, or otherwise results in a specific reduction in cellular levels of ROCK-II. Such cells may be cultured in vitro as a primary cell culture. Alternatively, such cells may be immortalized to establish a cell line. Any methods for constructing immortalized cell lines may be used in this respect. See generally Yeager and Reddel, *Curr. Opin. Biotech.,* 10:465-469 (1999). For example, the cells may be immortalized by transfection of plasmids expressing the SV40 early region genes (See e.g., Jha et al., *Exp. Cell Res.,* 245:1-7 (1998)), introduction of the HPV E6 and E7 oncogenes (See e.g., Reznikoff et al., *Genes Dev.,* 8:2227-2240 (1994)), and infection with Epstein-Barr virus (See e.g., Tahara et al., *Oncogene,* 15:1911-1920 (1997)). Alternatively, human cells expressing RNA molecules of the present invention that induce the degradation of RNA transcripts encoding ROCK-II may be immortalized by recombinantly expressing the gene for the human telomerase catalytic subunit hTERT. See Bodnar et al., *Science,* 279:349-352 (1998).

In alternative embodiments, cell models are provided by recombinantly manipulating appropriate host cells. The host cells may be bacteria cells, yeast cells, insect cells, plant cells, animal cells, and the like. Preferably, the cells are derived from mammals, most preferably humans. The host cells may be obtained directly from an individual, or a primary cell culture, or preferably an immortal stable human cell line. In a preferred embodiment, human embryonic stem cells or pluripotent cell lines derived from human stem cells are used as host cells. Methods for obtaining such cells are disclosed in, e.g., Shamblott, et al., *Proc. Natl. Acad. Sci. USA,* 95:13726-13731 (1998) and Thomson et al., *Science,* 282:1145-1147 (1998).

In one embodiment, a cell model is provided by recombinantly expressing one or more of the RNA molecules of the present invention within the cell. For this purpose, the methods for introducing nucleic acids into host cells disclosed in the context of gene therapy in above may also be used. The expression of the exogenous nucleic acids may be transient or, preferably stable. The methods for introducing nucleic acids into host cells disclosed in the context of gene therapy, above, may be used.

Cell-Based Assays:

The cell models of the present invention expressing an RNA molecule of the present invention can be used in screening assays to identify compounds useful in combination therapy for treating diseases and disorders involving viral infection. In addition, they may also be used for in vitro pre-clinical assays designed to test compounds, such as nucleic acid molecules of the present invention, for therapeutic effects.

For example, cells may be treated with various antiviral compounds to be tested for their effectiveness when used in combination therapy with the nucleic acids of the present invention. A variety of parameters relevant to particular viral diseases may be analyzed.

Transgenic Animals:

In another aspect of the present invention, transgenic non-human animals are created expressing RNA molecules of the present invention that induce the degradation of RNA transcripts encoding the animal counterpart (ortholog) of human ROCK-II. Animals of any species may be used to generate the transgenic animal models, including but not limited to, mice, rats, hamsters, sheep, pigs, rabbits, guinea pigs, preferably non-human primates such as monkeys, chimpanzees, baboons, and the like.

In one embodiment, transgenic animals are made to express one or more RNA molecules of the instant invention that induce the degradation of RNA transcripts encoding ROCK-II. Expression of such RNA molecules may be directed in a tissue or cell type that normally expresses the ROCK-II ortholog. Consequently, the concentration of the ROCK-II ortholog will be reduced to lower levels than normal.

To achieve reduced expression of ROCK-II orthologs in transgenic animals, the transgenic animals are made such that they contain expression cassettes directing the expression of an RNA molecule that induces the degradation of RNA transcripts encoding the ROCK-II ortholog. Preferably, expression of such RNAs from the expression cassette can be controlled. For example, the template encoding an RNA molecule of the present invention may be operably linked to an inducible promoter. Further, if the expression of the RNA molecule, and consequently the reduction in cellular concentrations of the ROCK-II ortholog, is desired to be limited to a particular tissue, an appropriate tissue-specific promoter may be used.

Any techniques known in the art for making transgenic animals may be used for purposes of the present invention. For example, the transgenic animals of the present invention may be provided by methods described in, e.g., Jaenisch, *Science,* 240:1468-1474 (1988); Capecchi, et al., *Science,* 244:1288-1291 (1989); Hasty et al., *Nature,* 350:243 (1991); Shinkai et al., *Cell,* 68:855 (1992); Mombaerts et al., *Cell,* 68:869 (1992); Philpott et al., *Science,* 256:1448 (1992); Snouwaert et al., *Science,* 257:1083 (1992); Donehower et al., *Nature,* 356:215 (1992); Hogan et al., Manipulating the Mouse Embryo; A Laboratory Manual, $2^{nd}$ edition, Cold Spring Harbor Laboratory Press, 1994; and U.S. Pat. Nos. 4,873,191; 5,800,998; 5,891,628, all of which are incorporated herein by reference in their entirety.

Generally, the founder lines may be established by introducing appropriate exogenous nucleic acids into, or modifying an endogenous gene in, germ lines, embryonic stem cells, embryos, or sperm which are then used in producing a transgenic animal. The gene introduction may be conducted by various methods including those described in the Gene Therapy Section, above. See also, Van der Putten et al., Proc. Natl. Acad. Sci. USA, 82:6148-6152 (1985); Thompson et al., Cell, 56:313-321 (1989); Lo, Mol. Cell. Biol., 3:1803-1814 (1983); Gordon, Transgenic Animals, Intl. Rev. Cytol. 115:171-229 (1989); and Lavitrano et al., Cell, 57:717-723 (1989). In a specific embodiment, the exogenous expression cassette is incorporated into an appropriate vector, such as those described above, and is transformed into embryonic stem (ES) cells. The transformed ES cells are then injected into a blastocyst. The blastocyst with the transformed ES cells is then implanted into a surrogate mother animal. In this manner, a chimeric founder line animal containing the exogenous nucleic acid (transgene) may be produced.

Preferably, site-specific recombination is employed to integrate the exogenous gene into a specific predetermined site in the animal genome, or to replace an endogenous gene or a portion thereof with the exogenous sequence. Various site-specific recombination systems may be used including those disclosed in Sauer, Curr. Opin. Biotechnol., 5:521-527 (1994); Capecchi, et al., Science, 244:1288-1291 (1989); and Gu et al., Science, 265:103-106 (1994). Specifically, the Cre/lox site-specific recombination system known in the art may be conveniently used which employs the bacteriophage P1 protein Cre recombinase and its recognition sequence loxP. See Rajewsky et al., J. Clin. Invest., 98:600-603 (1996); Sauer, Methods, 14:381-392 (1998); Gu et al., Cell, 73:1155-1164 (1993); Araki et al., Proc. Natl. Acad. Sci. USA, 92:160-164 (1995); Lakso et al., Proc. Natl. Acad. Sci. USA, 89:6232-6236 (1992); and Orban et al., Proc. Natl. Acad. Sci. USA, 89:6861-6865 (1992).

The transgenic animals of the present invention may be transgenic animals that carry a transgene in all cells or mosaic transgenic animals carrying a transgene only in certain cells, e.g., somatic cells. The transgenic animals may have a single copy or multiple copies of a particular transgene.

The founder transgenic animals thus produced may be bred to produce various offspring. For example, they can be inbred, outbred, and crossbred to establish homozygous lines, heterozygous lines, and compound homozygous or heterozygous lines.

Pharmaceutical Compositions and Formulations

In another aspect of the present invention, pharmaceutical compositions are provided containing one or more of the nucleic acid molecules of the present invention, which are capable of inducing the degradation of RNA transcripts encoding ROCK-II. The compositions are prepared as a pharmaceutical formulation suitable for administration into a patient. Accordingly, the present invention also extends to pharmaceutical compositions, medicaments, drugs or other compositions containing one or more of the therapeutic agents in accordance with the present invention.

For example, such therapeutic agents include, but are not limited to, (1) siRNA compounds specific to mRNA encoding ROCK-II, (2) shRNA compounds specific to mRNA encoding ROCK-II, (3) enzymatic nucleic acid compounds specific to mRNA or pre-mRNA encoding ROCK-II, (4) RNase H activating antisense oligonucleotides specific to mRNA or pre-mRNA encoding ROCK-II, and antisense oligonucleotides that otherwise specifically reduce the cellular levels of ROCK-II.

In certain embodiments of the present invention, the pharmaceutical composition of the instant invention further comprises agents that specifically enhance or increase the uptake or delivery of the nucleic acids that induce the degradation of RNA transcripts encoding ROCK-II, or otherwise result in a specific reduction in cellular levels of ROCK-II. Such agents that specifically enhance or increase the uptake or delivery of the nucleic acids of the invention are referred to, herein, as "uptake agents." Examples of uptake agents include, but are not limited to, amphipathic compounds and compounds used to formulate liposomes or immunoliposomes. Examples of such compounds are LIPOFECTIN®, LIPOFECTAMINE®, or CELLFECTIN®, and various polycations. Importantly, the uptake agents of the current invention include any compound that, when used in formulating the pharmaceutical composition of the instant invention, results in a net increase in the amount of the nucleic acids of the instant invention taken up by the treated cells, such that at least about a 10% decrease in ROCK-II encoding transcripts, or ROCK-II protein is observed in those cells treated with compositions including the uptake agent, versus cells treated with identical compositions, but lacking the uptake agent.

In the pharmaceutical composition, an active compound identified in accordance with the present invention can be in any pharmaceutically acceptable salt form. As used herein, the term "pharmaceutically acceptable salts" refers to the relatively non-toxic, organic or inorganic salts of the compounds of the present invention, including inorganic or organic acid addition salts of the compound. Examples of such salts include, but are not limited to, hydrochloride salts, sulfate salts, bisulfate salts, borate salts, nitrate salts, acetate salts, phosphate salts, hydrobromide salts, laurylsulfonate salts, glucoheptonate salts, oxalate salts, oleate salts, laurate salts, stearate salts, palmitate salts, valerate salts, benzoate salts, naphthylate salts, mesylate salts, tosylate salts, citrate salts, lactate salts, maleate salts, succinate salts, tartrate salts, fumarate salts, and the like. See, e.g., Berge, et al., J. Pharm. Sci., 66:1-19 (1977).

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophillic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacterial agents, surfactants, and antioxidants can all be included. For example, useful components include sodium chloride, acetate, citrate or phosphate buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al., *Annual Review of Medicine,* 39:221-229 (1988), which is incorporated herein by reference in its entirety.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al., *J. Clin. Psych.* 45:242-247 (1984). Hydrogels can be used as a carrier for the sustained release of the active compounds. Hydrogels are generally known in the art. They are typically made by crosslinking high molecular weight biocompatible polymers into a network that swells in water to form a gel like material. Preferably, hydrogels is biodegradable or biosorbable. For purposes of this invention, hydrogels made of polyethylene glycols, collagen, or poly(glycolic-co-L-lactic acid) may be useful. See, e.g., Phillips et al., *J. Pharmaceut. Sci.* 73:1718-1720 (1984).

The active compounds can also be conjugated, to a water-soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham, *Am. J. Hosp. Pharm.,* 15:210-218 (1994). PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., *Methods in Cell Biology*, Volume XIV, Academic Press, New York, N.Y. (1976).

The active compounds can also be administered in combination with another active agent that synergistically treats or prevents the same symptoms or is effective for another disease or symptom in the patient treated so long as the other active agent does not interfere with or adversely affect the effects of the active compounds of this invention. Such other active agents include but are not limited to anti-inflammation agents, antiviral agents, antibiotics, antifungal agents, antithrombotic agents, cardiovascular drugs, cholesterol lowering agents, anti-cancer drugs, hypertension drugs, and the like.

Generally, the toxicity profile and therapeutic efficacy of the therapeutic agents can be determined by standard pharmaceutical procedures in cell models or animal models, e.g., those provided above. As is known in the art, the $LD_{50}$ represents the dose lethal to about 50% of a tested population. The $ED_{50}$ is a parameter indicating the dose therapeutically effective in about 50% of a tested population. Both $LD_{50}$ and $ED_{50}$ can be determined in cell models and animal models. In addition, the $IC_{50}$ may also be obtained in cell models and animal models, which stands for the circulating plasma concentration that is effective in achieving about 50% of the maximal inhibition of the symptoms of a disease or disorder. Such data may be used in designing a dosage range for clinical trials in humans. Typically, as will be apparent to skilled artisans, the dosage range for human use should be designed such that the range centers on the $ED_{50}$ and/or $IC_{50}$, but significantly below the $LD_{50}$ obtained from cell or animal models.

It will be apparent to skilled artisans that therapeutically effective amount for each active compound to be included in a pharmaceutical composition of the present invention can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like. The amount of administration can also be adjusted as the various factors change over time.

Embodiments to Treat Viral Diseases:

In one embodiment, the methods of treatment are generally used to treat an individual experiencing an active viral infection, whether acute or chronic, by any of the aforementioned viruses. In another embodiment, the methods are generally used for treating a carrier of any of the aforementioned viruses who is not experiencing an active viral outbreak. In yet another embodiment, the methods are generally used to treat an individual who is known or suspected, to have been exposed to any of the aforementioned viruses. In still another embodiment, the methods are generally used to prophylactically treat an individual who is likely to be exposed to, or is at risk of being exposed to, any of the aforementioned viruses, and thereby prevent infection or lessen its symptoms.

In one particular embodiment, the methods are used for treating an HIV carrier who is not diagnosed as having developed AIDS (which is characterized by more serious AIDS-defining illnesses and/or a decline in the circulating CD4 cell count to below a level that is compatible with effective immune function, i.e. below about 200/μl). For example, the methods can be used in treating a patient at any stages the HIV infection prior to diagnosis of AIDS, including acute HIV syndrome (or acute primary HIV infection syndrome) and asymptomatic infection (which is the long latent period with a gradual decline in the number of circulating CD4 T cells).

In one aspect, the present invention provides methods for treating viral infection—at any stage, and caused by any of the aforementioned viruses, and particularly HIV—in patients who have been, or are being, treated with one or more established antiviral drugs. Examples of such other antiviral compounds include, but are not limited to, protease inhibitors, nucleoside reverse transcriptase inhibitors, non-nucleoside reverse transcriptase inhibitors, integrase inhibitors, fusion inhibitors, and combinations thereof. The compounds containing a nucleic acid molecule that induces the degradation of RNA transcripts encoding ROCK-II, or otherwise results in a specific reduction in cellular levels of ROCK-II, can be administered to patients who do not respond well to other antiviral drugs (e.g., non-responding, or developing viral resistance) or who experience relapses after treatment with one or more other antiviral drugs or regimens. As used herein, "non-responding patient" or patient "who does not respond well to other antiviral drugs" connote professional observations or judgment by a physician under relevant medical standard or customary practice in the field of antiviral infection therapy. For example, in the case of HIV, a patient may be characterized as non-responding or not responding well if his or her plasma HIV RNA level (or equivalent thereof) does not substantially decrease after treatment with one or more other anti-HIV drugs for a sufficient period of time, or if the reduction of plasma HIV RNA level (or equivalent thereof) is less than a tenfold drop by 4 weeks following the initiation of therapy. Other indications for non-responding patients may include, e.g., persistent decline of CD4 T-cell numbers, adverse drug reaction or toxicity, and clinical deterioration. Thus, the method of the present invention includes a step of identifying such a patient and subsequently administering to the patient a pharmaceutical composition or medicament having a therapeutically effective amount of a compound containing a nucleic acid molecule that induces the degradation of RNA transcripts encoding ROCK-II, or otherwise results in a specific reduction in cellular levels of ROCK-II.

In another embodiment, a compound containing a nucleic acid molecule that induces the degradation of RNA transcripts encoding ROCK-II, or otherwise results in a specific reduction in cellular levels of ROCK-II, is administered to a patient who has undergone a treatment with one or more drugs that target a viral protein such as viral protease, reverse transcriptase, integrase, envelope protein (e.g., gp120 and gp41 for anti-fusion or homologue thereof), and has not responded well to the treatment. Particularly, the compounds of the present invention belong to a novel class of antiviral drug that is believed to target certain host cell protein(s). Their mode of action is distinct from other antiviral drugs. Thus, they can be especially effective in treating virus-infected patients who do not respond to one or more other antiviral drugs of a different class or who experience relapse after treatment with one or more antiviral drugs of a different class.

In addition, the present invention further provides methods for delaying the onset of acute infection comprising administering a pharmaceutical composition or medicament having a prophylactically effective amount of a compound containing a nucleic acid molecule that induces the degradation of RNA transcripts encoding ROCK-II, or otherwise results in a specific reduction in cellular levels of ROCK-II, to an individual having an acute viral infection or at risk of viral infection or at risk of developing symptomatic infection. For example, in delaying the onset of symptomatic infection, an individual infected with a virus or at risk of viral infection can be identified, and administered with a prophylactically effective amount of a compound containing a nucleic acid molecule that induces the degradation of RNA transcripts encoding ROCK-II, or otherwise results in a specific reduction in cellular levels of ROCK-II, that is, an amount sufficient to delay the onset of acute viral infection by at least six months. Preferably, an amount is used sufficient to delay the onset of acute viral infection by at least 12 months, 18 months or 24 months.

In addition, the present invention also provides methods for delaying the onset of a symptomatic viral infection comprising identifying an individual who (1) is at risk of infection by a virus, or (2) is suspected of infection by a virus or of exposure to a virus, or (3) has a suspected past exposure to a virus, and administering to the individual a pharmaceutical composition or medicament having a prophylactically effective amount of a compound containing a nucleic acid molecule that induces the degradation of RNA transcripts encoding ROCK-II, or otherwise results in a specific reduction in cellular levels of ROCK-II.

Combination Therapy:

For purposes of preventing viral infection, treating asymptomatic viral infection, delaying the onset of symptomatic viral infection, or treating symptomatic viral infection, a compound of the present invention may be used in combination with one or more other antiviral compounds, preferably other antiviral compounds that act through different mechanisms of action. Examples of such other antiviral compounds include, but are not limited to, protease inhibitors, nucleoside reverse transcriptase inhibitors, non-nucleoside reverse transcriptase inhibitors, integrase inhibitors, fusion inhibitors, and a combination thereof. “Co-administration or co-administering” means that the active pharmaceutical agents are administered together as a part of the same therapeutic or treatment regime. The active pharmaceutical agents can be administered separately at different times of the day or at the same time. Additionally, the present invention also provides a pharmaceutical composition having a compound containing a nucleic acid molecule that induces the degradation of RNA transcripts encoding ROCK-II, or otherwise results in a specific reduction in cellular levels of ROCK-II, and a compound selected from protease inhibitors, nucleoside reverse transcriptase inhibitors, non-nucleoside reverse transcriptase inhibitors, integrase inhibitors, fusion inhibitors, immunomodulators, vaccines, and combinations thereof. However, it is to be understood that such other antiviral compounds should not interfere with, or adversely affect, the intended effects of the active compounds of this invention. According to this aspect of the invention, a method is provided by co-administering to an individual in need of treatment a therapeutically effective amount of a compound containing a nucleic acid molecule that induces the degradation of RNA transcripts encoding ROCK-II, or otherwise results in a specific reduction in cellular levels of ROCK-II, and a therapeutically effective amount of one or more other antiviral compounds.

Accordingly, the present invention also provides pharmaceutical compositions or medicaments useful for the above treatment and prevention purposes and having a therapeutically effective amount of a compound containing a nucleic acid molecule that induces the degradation of RNA transcripts encoding ROCK-II, or otherwise results in a specific reduction in cellular levels of ROCK-II, and a therapeutically effective amount of one or more other antiviral compounds. Preferably, such other antiviral compounds have a different mode of action than that of the compounds containing a nucleic acid molecule that induces the degradation of RNA transcripts encoding ROCK-II, or otherwise results in a specific reduction in cellular levels of ROCK-II. More preferably, such other antiviral compounds target a viral protein. Examples of such compounds include, but are not limited to, protease inhibitors, nucleoside reverse transcriptase inhibitors, non-nucleoside reverse transcriptase inhibitors, integrase inhibitors, fusion inhibitors, and combinations thereof.

The present invention further provides an article of manufacture comprising a pharmaceutical composition or medicament having a therapeutically or prophylactically effective amount of a compound containing a nucleic acid molecule that induces the degradation of RNA transcripts encoding ROCK-II, or otherwise results in a specific reduction in cellular levels of ROCK-II. The pharmaceutical composition or medicament can be in a container such as bottle, gel capsule, vial or syringe. The article of manufacture may also include instructions for the use of the pharmaceutical composition or medicament in the various antiviral applications provided above. The instructions can be printed on paper, or in the form of a pamphlet or book. Preferably, the article of manufacture according to the present invention further comprises a therapeutically or prophylactically effective amount of one or more other antiviral compounds as described above.

Generally, the toxicity profile and therapeutic efficacy of the therapeutic agents can be determined by standard pharmaceutical procedures in suitable cell models or animal models. As is known in the art, the $LD_{50}$ represents the dose lethal to about 50% of a tested population. The $ED_{50}$ is a parameter indicating the dose therapeutically effective in about 50% of a tested population. Both $LD_{50}$ and $ED_{50}$ can be determined in cell models and animal models. In addition, the $IC_{50}$, which stands for the circulating plasma concentration that is effective in achieving about 50% of the maximal inhibition of the symptoms of a disease or disorder, may also be obtained in cell models and animal models. Such data may be used in designing a dosage range for clinical trials in humans. Typically, as will be apparent to skilled artisans, the dosage range for human use should be designed such that the range centers on the $ED_{50}$ and/or $IC_{50}$, but significantly below the $LD_{50}$ obtained from cell or animal models.

Typically, compounds containing nucleic acid molecule s that induce degradation of RNA transcripts encoding ROCK-II can be effective at an amount of from about 0.01 μg/kg to about 100 mg/kg per day based on total body weight. The active ingredient may be administered at once, or may be divided into a number of smaller doses to be administered at predetermined intervals of time. The suitable dosage unit for each administration can be, e.g., from about 1 μg to about 2000 mg, preferably from about 5 μg to about 1000 mg.

In the case of combination therapy, a therapeutically effective amount of one or more other antiviral compounds can be administered in a separate pharmaceutical composition, or alternatively included in the pharmaceutical composition according to the present invention which contains a nucleic acid molecule that induces the degradation of RNA transcripts encoding ROCK-II, or otherwise results in a specific reduction in cellular levels of ROCK-II. Importantly, in combination therapy, the administration of a nucleic acid molecule of the present invention and the administration of another antiviral compound, which is not a nucleic acid molecule of the present invention, can be simultaneous, or in any order. That is, a nucleic acid molecule of the present invention, can be administered prior to, simultaneously with, or after the administration of another antiviral compound, which is not a nucleic acid molecule of the present invention. The pharmacology and toxicology of many of such other antiviral compounds are known in the art. See e.g., *Physicians Desk Reference*, Medical Economics, Montvale, N.J.; and *The Merck Index*, Merck & Co., Rahway, N.J. The therapeutically effective amounts and suitable unit dosage ranges of such compounds used in art can be equally applicable in the present invention.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can be adjusted as the various factors change over time.

In the pharmaceutical compositions, the active agents can be in any pharmaceutically acceptable salt form. As used herein, the term "pharmaceutically acceptable salts" refers to the relatively non-toxic, organic or inorganic salts of the active compounds, including inorganic or organic acid addition salts of the compound. Examples of salts of basic active ingredient compounds include, but are not limited to, hydrochloride salts, hydrobromide salts, sulfate salts, bisulfate salts, nitrate salts, acetate salts, phosphate salts, nitrate salts, oxalate salts, valerate salts, oleate salts, borate salts, benzoate salts, laurate salts, stearate salts, palmitate salts, lactate salts, tosylate salts, citrate salts, maleate, salts, succinate salts, tartrate salts, naphthylate salts, fumarate salts, mesylate salts, laurylsulphonate salts, glucoheptonate salts, and the like. See, e.g., Berge, et al. *J. Pharm. Sci.,* 66:1-19 (1977). Examples of salts of acidic active ingredient compounds include, e.g., alkali metal salts, alkaline earth salts, and ammonium salts. Thus, suitable salts may be salts of aluminum, calcium, lithium, magnesium, potassium, sodium and zinc. In addition, organic salts may also be used including, e.g., salts of lysine, N,N'-dibenzylethylenediamine, chloroprocaine, choline, diethanolamine, ethylenediamine, meglumine (N-methylglucamine), procaine and tris.

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al., *Annual Review of Medicine,* 39:221-229 (1988), which is incorporated herein by reference in its entirety.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al., *J. Clin. Psych.* 45:242-247 (1984). Hydrogels can be used as a carrier for the sustained release of the active compounds. Hydrogels are generally known in the art. They are typically made by crosslinking high molecular weight biocompatible polymers into a network, which swells in water to form a gel like material. Preferably, hydrogels are biodegradable or biosorbable. For purposes of this invention, hydrogels made of polyethylene glycols, collagen, or poly(glycolic-co-L-lactic acid) may be useful. See, e.g., Phillips et al., *J. Pharmaceut. Sci.,* 73:1718-1720 (1984).

The active compounds can also be conjugated, to a water-soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham, *Am. J. Hosp. Pharm.,* 15:210-218 (1994). PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., *Methods in Cell Biology*, Volume XIV, Academic Press, New York, N.Y. (1976).

The active compounds can also be administered in combination with another active agent that synergistically treats or prevents the same symptoms or is effective for another disease or symptom in the patient treated so long as the other active agent does not interfere with or adversely affect the effects of the active compounds of this invention. Such other active agents include but are not limited to anti-inflammation agents, antiviral agents, antibiotics, antifungal agents, antithrombotic agents, cardiovascular drugs, cholesterol lowering agents, anti-cancer drugs, hypertension drugs, and the like.

EXAMPLES

Example 1

Testing siRNAs for Their Ability to Knock Down ROCK-II Expression

Three different siRNAs were tested for their ability to knock down the expression of ROCK-II protein in 293T cells. The three siRNAs used in these experiments are shown below.

```
    GUGCAGUUGGUUCGUCACAdTdT   SEQ ID NO:50
      |||||||||||||||||||
dTdTCACGUCAACCAAGCAGUGU       SEQ ID NO:51


    GUGACUCUCCAUCUUGUAGdTdT   SEQ ID NO:54
      |||||||||||||||||||
dTdTCACUGAGAGGUAGAACAUC       SEQ ID NO:55


    GAACCUGUCAAGCGUGGUAdTdT   SEQ ID NO:68
      |||||||||||||||||||
dTdTCUUGGACAGUUCGCACCAU       SEQ ID NO:69
```

These siRNAs correspond to the following 19-nucleotide target sequences within the ROCK-II coding sequence:

siRNA #1: 5'-GUGCAGUUGGUUCGUCACA-3' (nt 316-334; SEQ ID NO:3), siRNA #3: 5'-GUGACUCUCCAUCUUGUAG-3' (nt 1268-1286; SEQ ID NO:11), and siRNA #10: 5'-GAACCUGUCAAGCGUGGUA-3' (nt 3136-3154; SEQ ID NO:29).

siRNA Transfections:

The day before transfections, $1\times10^5$ 293T cells were seeded into each well of a 12-well plate with 1 ml of fresh DMEM supplemented with 10% FBS and 1×NEAA, but without antibiotics. The day of the transfections, 100 pmol of all three ROCK-II siRNA duplexes (2 μl of 50 μM stock solution of each duplex) were diluted separately with 100 μl of Opti-MIM I medium. Additionally, 3 μl of LipofectAmine 2000 reagent (LF2000; Invitrogen, Inc., Carlsbad, Calif., USA) was diluted with 100 μl of Opti-MEM I medium and incubated at RT for 5 minutes. The diluted LF2000 and different diluted siRNA duplexes, were then gently mixed and incubated at RT for 20 minutes. Transfections were initiated by transferring 200 μl of each mixed LF2000/siRNA into a separate well of the plate containing the seeded cells and rocking the plate to mix gently. The plate was then incubated Incubate for 48 hours at 37 C before cells were harvested and used to prepare lysates.

Detection of ROCK-II Expression by Western Blot:

20 μl of cell lysate mixed with SDS loading buffer was loaded per well in 1.5 mm thick/10 well 4-12% Tris-Glycine acrylamide gel. Prestained Molecular Weight Standards were also loaded into a single well according to manufacturer's instructions. The gel was electrophoresed at 135 V for about 2 hours. Proteins were electro-transferred from the gel to a nitrocellulose membrane as follows: the gel, nitrocellulose membrane, filter paper, and sponge pad were pre-wet with 1× transfer buffer; the transfer sandwich was prepared and placed into the transfer module, which was filled with 1× Transfer Buffer, while the outside compartment with filled with water; the transfer apparatus was then subjected to 25 V for 2 hr. Following transfer the nitrocellulose membrane (western blot) was blocked with 5% milk in 1×TBST for 60 minutes at room temperature (or overnight at 4° C.). The blocked membrane was then incubated in primary antibody (anti-ROCK-II) diluted in 1×TBST for 1 hour at room temperature. The primary antibody was mouse anti-ROCK-II from BD Biosciences/Pharmingen (San Diego, Calif., USA). The membrane was washed three times for 5 minutes each with 1×TBST and incubated for 30 minutes at room temperature with horseradish peroxidase (HRP) conjugated secondary antibody. The membrane was then washed three times for 5 minutes each with 1×TBST, and once for 5 minutes with 1×TBS. The membrane was then incubated in ECL reagent for 1 minute at RT, and the signal was detected by either exposing the blot to film or by using the BioChemi system of UVP BioImaging Systems.

Results:

FIG. 3 depicts a Western blot demonstrating knockdown of ROCK-II expression by three siRNAs. The leftmost (unlabeled) lane shows prestained markers. Lane 1 shows a Tsg101 siRNA treatment. Lane 2 shows a Tsg101 inverted siRNA treatment. Lane 3 shows a ROCK-II siRNA #1 treatment. Lane 4 shows a ROCK-II siRNA #3 treatment. Lane 5 shows a ROCK-II siRNA #10 treatment. The results (FIG. 3) indicate that all three siRNAs directed to ROCK-II knocked down the level of ROCK-II protein expression by about 60-70%.

Example 2

VLP Assay $5\times10^4$ 293T cells are seeded into a well of 24-well plate with 0.6 ml of fresh DMEM supplemented with 10% FBS and 1×NEAA without antibiotics. On the day of transfection, 0.6 μg of pEGFP-Gag(HIV-1) plasmid DNA is diluted with 50 μl of Opti-MIM I medium. The same amount of a plasmid with HIV GAG mutated at the p6 late domain motif [pEGFP-Gag(HIV-1/LIRL)] is diluted in the same manner. Each of the diluted plasmid DNA is combined with 2 μl of LipofectAmine 2000 reagent (Invitrogen) in 50 μl of Opti-MEM I medium and used subsequently in transfecting the plated 293T cells according standard protocols provided by manufacturer. Different concentrations of (+)-(R)-trans-4-(1-aminoethyl)-N-(4-pyridyl)cyclohexanecarboxamide dihydrochloride hydrate (Calbiochem, La Jolla, Calif., USA) are added to the transfected cells.

An aliquot of post-transfection cell culture medium is collected and passed through a 0.45 μm syringe filter and centrifuged in 20% sucrose 14,000 rpm at 4° C. for 90 minutes. The supernatant is removed but for about 20 μl. The residue is resuspended with Hank's Balanced Salt Solution (Invitrogen) and is used in the p24 ELISA assay described below.

The remaining culture media in the cell culture plate is removed and the cells are lysed with cell lysis buffer and processed for protein expression assays.

For HIV-1 p24 ELISA assays, kits from PerkinElmer Life Sciences, Inc. are used according standard protocols provided by the manufacturer. Briefly, the above-described processed sample is mixed with buffer and incubated in the wells of anti-p24 antibody-coated Microplate to allow antibody-antigen binding. The plate is then washed with diluted wash buffer. Detector Antibody is then added to the wells, and incubated at 37° C. for 1 hour. The plate is then washed again with diluted wash buffer. Diluted Streptavidin-HRP is added to all wells, and incubated at room temperature for 30 minutes. The plate is washed again with diluted wash buffer. OPD substrate solution is added to all wells, and incubated at room temperature for 30 minutes. The reaction is stopped by adding 100 μl of Stop Solution to all wells. The plate is read at 490 nm within 15 minutes after stop.

For immunoblot assay to detect protein expression, cell lysates as described above are subjected to electrophoresis in 4-12% NuPAGE Bis-Tris acrylamide gel. The proteins are then transferred from the gel to a nitrocellulose membrane. The blot is blocked with 5% milk in 1×TBST for 60 min at room temperature, and then incubated in primary antibody diluted in 1×TBST for 1 hour at room temperature. The membrane is then washed and incubated for 30 min at room temperature with horseradish peroxidase (HRP) conjugated secondary antibody. The membrane is washed again and incubated in ECL reagent for 1 minute at room temperature. The signal is detected by exposing the membrane to a film or by BioChemi system of UVP BioImaging Systems. Rabbit anti-GFP from Invitrogen is used as primary antibody.

Example 3

Anti-HIV Assays

In an acute infection assay, fresh PBMCs (peripheral blood mononuclear cells) are isolated from human blood and stimulated to grow with PHA-P and IL-2 in RPMI culture medium. To cells growing in 96 well plates, dilutions of each compound are added followed by an aliquot of HIV-1 (ROJO isolate) virus stock at an MOI of 0.1. Wells with cells and virus alone, along with a titration of AZT are used as controls. A duplicate plate without virus is identically prepared for cytotoxicity (MTS assay) studies. At the end of 7 days, cell-free supernatant samples are collected and assayed for reverse transcriptase activity. For these studies, serial dilutions of the compounds are tested for antiviral activity.

A microtiter based reverse transcriptase (RT) reaction is utilized. See Buckheit et al., *AIDS Research and Human Retroviruses* 7:295-302 (1991). Tritiated thymidine triphosphate (TTP; New England Nuclear) is resuspended in distilled $H_2O$ at 5 Ci/ml. Poly rA and oligo dT are prepared as a stock solution, which is kept at −20° C. The RT reaction buffer is prepared fresh on a daily basis and consists of 125 μl 1M EGTA, 125 μl dH2O, 110 μl 10% SDS, 50 μl 1M Tris (pH 7.4), 50 μl 1M DTT, and 40 μl 1M MgCL2. These three solutions are mixed together in a ratio of 2 parts TTP, 1 part poly rA:oligo dT, and 1 part reaction buffer. Ten microliters of this reactions mixture is placed at a round bottom microtiter plate and 15 μl of virus containing supernatant is added and mixed. The plate is incubated at 37° C. in a water bath with a solid support to prevent submersion of the plate and incubated for 60 min. Following the reaction, the entire reaction volume is spotted onto pieces of DE81 paper, washed 5 times 5 min each in a 5% sodium phosphate buffer, 2 times 1 min each in distilled water, 2 times for 1 min each in 70% ethanol, and then dried. Opti-Fluor-O (Packard) is added to each sample and incorporated radioactivity is quantified utilizing a Wallac 1450 MicroBeta Plus liquid scintillation counter.

At assay termination the assay plates are stained with the soluble tetrazolium-based dye MTS (CellTiter Reagent, Promega Corp., Madison, Wis., USA) to determine cell viability and quantify compound toxicity. MTS is metabolized by the mitochondrial enzymes of metabolically active cells to yield a soluble formazan product, allowing the rapid quantitative analysis cell viability and compound cytotoxicity. The MTS is a stable solution that does not require preparation before use. At termination of the assay, 20 microliters of MTS reagent is added per well. The wells are incubated overnight for the HIV cytoprotection assay at 37° C. The incubation intervals are chosen based on empirically determined times for optimal dye reduction in each cell type. Adhesive plate sealers are used in place of the lids, the sealed plate is inverted several times to mix the soluble formazan product and the plate is read spectrophotometrically at 490 nm with a Molecular Devices Vmax plate reader.

In addition, HIV-infected cells treated with the compounds are also studied under an electronic microscope or similar devices to examine if the viruses are defective in viral budding from the cells.

Example 4

Inhibition of EIAV Infectivity with Compounds Containing a Nucleic Acid Molecule that Induces the Degradation of RNA Transcripts Encoding ROCK-II or Otherwise Results in a Specific Reduction in Cellular Levels of ROCK-II Plasmid Construct:

The EIAV construct used for these experiments is pEV53. The plasmid contains an EIAV proviral sequence with a partial deletion of the Env gene cloned into the pcDNA3.1 mammalian expression vector (Invitrogen, Inc., Carlsbad, Calif., USA).

Transfection of cultured cells is done with EIAV Provirus plasmid and cells are treated with individual compounds containing a nucleic acid molecule that induces the degradation of RNA transcripts encoding ROCK-II.

$1\times10^5$ 293T cells/well are seeded into a 12-well plate with 1 ml of fresh DMEM (10% FBS, 1×NEAA without antibiotics) and allowed to adhere for 24 h. Transfection is carried out according to manufacturer's recommendations. Briefly, 1 μg of pEV53 plasmid DNA is combined with 100 μl of Opti-MIM I medium. 3 μl of LipofectAmine 2000 reagent (Invitrogen) is then added to 100 μl of Opti-MEM I medium & incubated at RT for 5 min. The DNA/Opti-MIM I & Lipofectamine 2000/Opti-MEM I solutions are then combined and mixed gently followed by incubation at room temperature for 20 min. 200 µl of DNA/Lipofectamine 2000 solution is then added to the 293T cells in each well of the plate and mixed gently by rocking. The plate is then placed at 37° C., 5% $CO_2$ in a humidified incubator for 2 h. Various concentrations of individual compounds according to Formulae I & II (dissolved in water or another suitable solvent) are added to each well of the plate and incubated for 48 h post-transfection.

Reverse Transcription Assay:

1.0 ml of post-transfection cell culture medium is collected, passed through a 0.45 µm syringe filter and layered on top of 200 µl of 20% sucrose. This discontinuous gradient is then centrifuged at 14,000 rpm (4° C.) for 90 minutes. The supernatant is carefully removed leaving 20 µl in the tube. The pellet contained in the remaining ~20 µl is resuspended in 150 µl of HBSS (Hank's Balanced Salt Solution; Invitrogen, Inc., Carlsbad, Calif., USA) and used for the Reverse Transcriptase Assay.

Reverse Transcriptase Assay (Quan-T-RT Assay from Amersham Biosciences, Piscataway, N.J., USA)

This assay is used to quantitate the reverse transcriptase activity present in retroviral virions. The level of reverse transcriptase activity is used as surrogate measurement for viral particle output from cells transfected with EIAV (Equine infectious anemia virus) proviral DNA. A reduction in the level of reverse transcriptase activity indicates inhibition of viral replication. The reverse transcription assay is carried out according to manufacturer's recommendations.

1. Preparation of [3H]TTP Solution 1.1. Mix 10 µl of [$^3$H]TTP stock solution with 190 µl of 5.25× assay buffer (this amount is sufficient for 10 assays using 20 µl per assay).

2. Assay Procedure 2.1. Pipette 10 µl of primer/template on SPA bead into each tube.

2.2. Add 20 µl of TTP/[3H]TTP solution from 1.1 into each tube.

2.3. Add appropriate volume of sample and mix by pipette up and down.

2.4. Finally add ddH2O to final volume of 100 µl.

2.5. Incubate the tubes for 2 h at 37° C.

2.6. Terminate the reaction by adding 200 µl of stop reagent into each tube.

2.7. Count the tubes in a scintillation counter with the window settings fully open.

The results of these studies indicate whether the compounds according to Formulae I & II reduce or inhibit the infectivity of the virus EAIV.

Example 5

Inhibition of MMLV Infectivity with Compounds Containing a Nucleic Acid Molecule that Induces the Degradation of RNA Transcripts Encoding ROCK-II, or Otherwise Results in a Specific Reduction in Cellular Levels of ROCK-II MMLV infectivity is assessed using the procedure of Telesnitsky A., et al. Assays for retroviral reverse transcriptase. *Methods Enzymol.* 262:347-362 (1995). The results of this assay demonstrate whether or not the compounds of Formulae I & II reduce or inhibit the infectivity of the virus MMLV.

All publications, patents and patent application publications cited above are herein incorporated by reference herein to the same extent as if each individual publication, patent or patent application publication was specifically and individually indicated to be incorporated by reference herein. The mere mentioning of the publications and patent applications does not necessarily constitute an admission that they constitute prior art to the instant invention or application.

Although the foregoing invention has been described in some detail by way of illustration and example for purposes of clarity of understanding, it will be obvious that certain changes and modifications may be practiced within the scope of the appended claims.

What is claimed is:

1. A nucleic acid molecule that directs the cleavage of a Rho-associated, coiled-coil containing protein kinase 2 (ROCK-II)-encoding RNA transcript via RNA interference (RNAi), comprising a first nucleotide sequence and a second nucleotide sequence, wherein:

said first nucleotide sequence comprises SEQ ID NO:3;

said second nucleotide sequence is substantially complementary to said first nucleotide sequence; each of said first and second nucleotide sequences is about 21 nucleotides in length; and said second nucleotide sequence is sufficiently complementary to SEQ ID NO:2 for the nucleic acid molecule to direct cleavage of said ROCK-II-encoding RNA transcript and decrease the expression of ROCK-II via RNAi.

2. The nucleic acid of claim 1, wherein:

said first nucleotide sequence occurs within a first strand of RNA;

said second nucleotide sequence occurs within a second strand of RNA;

each of said first and second nucleotide sequences is about 21 nucleotides in length; and said first strand of RNA and said second strand of RNA are annealed to form an intermolecular duplex.

3. A composition comprising the nucleic acid of claim 2 and a pharmaceutically acceptable carrier or diluent.

4. The composition of claim 3, further comprising an uptake agent.

5. The composition of claim 4, wherein said uptake agent is selected from LIPOFECTIN®, LIPOFECTAMINE®, or CELLFECTIN®.

6. A modified equivalent of the nucleic acid of claim 2.

7. A composition comprising the modified equivalent of claim 6 and a pharmaceutically acceptable carrier or diluent.

8. The composition of claim 7, further comprising an uptake agent.

9. The composition of claim 8, wherein said uptake agent is selected from LIPOFECTIN®, LIPOFECTAMINE®, or CELLFECTIN®.

10. The nucleic acid of claim 1, wherein said first and second nucleotide sequences of RNA each further comprise two 2'-deoxythymidine residues at their 3' ends, and said nucleic acid is prepared by the annealing of the nucleic acids of SEQ ID NOs:50 and 51.

11. The nucleic acid of claim 1, wherein:

said first nucleotide sequence and said second nucleotide sequence occur within a single strand of RNA, said single strand of RNA is comprised of about 52 nucleotides, and said first nucleotide sequence and said second nucleotide sequence anneal to form an intramolecular duplex of about 19 basepairs.

12. A composition comprising the nucleic acid of claim 11 and a pharmaceutically acceptable carrier or diluent.

13. The composition of claim 12, further comprising an uptake agent.

14. The composition of claim 13, wherein said uptake agent is selected from LIPOFECTIN®, LIPOFECTAMINE®, or CELLFECTIN®.

15. The nucleic acid of claim 11, wherein said single strand of RNA comprises SEQ ID NO:74.

16. A composition comprising the nucleic acid of claim 15 and a pharmaceutically acceptable carrier or diluent.

17. The composition of claim 16, further comprising an uptake agent.

18. The composition of claim 17, wherein said uptake agent is selected from LIPOFECTIN®, LIPOFECTAMINE®, or CELLFECTIN®.

* * * * *

SEQUENCE LISTING

```
<160> NUMBER OF SEQ ID NOS: 85

<210> SEQ ID NO 1
<211> LENGTH: 6409
<212> TYPE: DNA
<213> ORGANISM: Homo sapiens

<400> SEQUENCE: 1

caaggcggcc ggcggcgacc atggcagcgg gccggcggcg gccgtagtgg cccaggcctg      60

ggcttcagcc tcccggggcc ccagagggcg gggcggtccg ggccgcggcg gtggcggcgc     120

cacttccctg ctcccgcccg aggactcctg cgggcactcg ctgaggacca gcggaccggc     180

ggcgcgaatc tgactgaggg gcggggacgc cgtctgttcc ccgccgctcc cggcagggcc     240

gggccgggcc gggctgggcc gggctgggcc gggcgggccc ctgggagcag cccccaggcg     300

ggggaccgcc ttggagaccc gaagccggag ctagaggcag gcggtgggcc cgggtggagt     360

cccggccgga gctggtggtt cgggggcggt gctaggcccc gaggctgcgg gacctgagcg     420

cgaggagcct gagtgcgggt ccagcggtgg cggcatgagc cggcccccgc cgacggggaa     480
```

-continued

```
aatgcccggc gcccccgaga ccgcgccggg ggacggggca ggcgcgagcc gccagaggaa    540
gctggaggcg ctgatccgag accctcgctc ccccatcaac gtggagagct tgctggatgg    600
cttaaattcc ttggtccttg atttagattt tcctgctttg aggaaaaaca agaacataga    660
taatttctta aatagatatg agaaaattgt gaaaaaaatc agaggtctac agatgaaggc    720
agaagactat gatgttgtaa aagttattgg aagaggtgct tttggtgaag tgcagttggt    780
tcgtcacaag gcatcgcaga aggtttatgc tatgaagctt cttagtaagt ttgaaatgat    840
aaaaagatca gattctgcct ttttttggga agaaagagat attatggcct ttgccaatag    900
cccctgggtg gttcagcttt tttatgcctt tcaagatgat aggtatctgt acatggtaat    960
ggagtacatg cctggtggag accttgtaaa ccttatgagt aattatgatg tgcctgaaaa   1020
atgggccaaa ttttacactg ctgaagttgt tcttgctctg gatgcaatac actccatggg   1080
tttaatacac agagatgtga agcctgacaa catgctcttg gataaacatg gacatctaaa   1140
attagcagat tttggcacgt gtatgaagat ggatgaaaca ggcatggtac attgtgatac   1200
agcagttgga acaccggatt atatatcacc tgaggttctg aaatcacaag gggtgatgg    1260
tttctatggg cgagaatgtg attggtggtc tgtaggtgtt ttcctttatg agatgctagt   1320
gggggatact ccattttatg cggattcact tgtaggaaca tatagcaaaa ttatggatca   1380
taagaattca ctgtgtttcc ctgaagatgc agaaatttcc aaacatgcaa agaatctcat   1440
ctgtgctttc ttaacagata gggaggtacg acttgggaga aatggggtgg aagaaatcag   1500
acagcatcct ttctttaaga atgatcagtg gcattgggat aacataagag aaacggcagc   1560
tcctgtagta cctgaactca gcagtgacat agacagcagc aatttcgatg acattgaaga   1620
tgacaaagga gatgtagaaa ccttcccaat tcctaaagct tttgttggaa atcagctgcc   1680
tttcatcgga tttacctact atagagaaaa tttattatta agtgactctc catcttgtag   1740
agaaaatgat tccatacaat caaggaaaaa tgaagaaagt caagagattc agaaaaaact   1800
gtatacatta gaagaacatc ttagcaatga gatgcaagcc aaagaggaac tggaacagaa   1860
gtgcaaatct gttaatactc gcctagaaaa aacagcaaag gagctagaag aggagattac   1920
cttacggaaa agtgtggaat cagcattaag acagttagaa agagaaaagg cgcttcttca   1980
gcacaaaaat gcagaatatc agaggaaagc tgatcatgaa gcagacaaaa aacgaaattt   2040
ggaaaatgat gttaacagct taaaagatca acttgaagat ttgaaaaaaa gaaatcaaaa   2100
ctctcaaata tccactgaga aagtgaatca actccagaga caactggatg aaaccaatgc   2160
tttactgcga acagagtctg atactgcagc ccggttaagg aaaacccagg cagaaagttc   2220
aaaacagatt cagcagctgg aatctaacaa tagagatcta caagataaaa actgcctgct   2280
ggagactgcc aagttaaaac ttgaaaagga atttatcaat cttcagtcag ctctagaatc   2340
tgaaaggagg gatcgaaccc atggatcaga gataattaat gatttacaag gtagaatatg   2400
tggcctagaa gaagatttaa agaacggcaa aatcttacta gcgaaagtag aactggagaa   2460
gagacaactt caggagagat ttactgattt ggaaaaggaa aaaagcaaca tggaaataga   2520
tatgacatac caactaaaag ttatacagca gagcctagaa caagaagaag ctgaacataa   2580
ggccacaaag gcacgactag cagataaaaa taagatctat gagtccatcg aagaagccaa   2640
atcagaagcc atgaaagaaa tggagaagaa gctcttggag gaaagaactt taaaacagaa   2700
agtggagaac ctattgctag aagctgagaa aagatgttct ctattagact gtgacctcaa   2760
acagtcacag cagaaaataa atgagctcct taaacagaaa gatgtgctaa atgaggatgt   2820
tagaaacctg acattaaaaa tagagcaaga aactcagaag cgctgcctta cacaaaatga   2880
```

-continued

```
cctgaagatg caaacacaac aggttaacac actaaaaatg tcagaaaagc agttaaagca   2940
agaaaataac catctcatgg aaatgaaaat gaacttggaa aaacaaaatg ctgaacttcg   3000
aaaagaacgt caggatgcag atgggcaaat gaaagagctc caggatcagc tcgaagcaga   3060
acagtatttc tcaacccttt ataaaacaca agttagggag cttaaagaag aatgtgaaga   3120
aaagaccaaa cttggtaaag aattgcagca gaagaaacag gaattacagg atgaacggga   3180
ctctttggct gcccaactgg agatcacctt gaccaaagca gattctgagc aactggctcg   3240
ttcaattgct gaagaacaat attctgattt ggaaaaagag aagatcatga aagagctgga   3300
gatcaaagag atgatggcta gacacaaaca ggaacttacg gaaaaagatg ctacaattgc   3360
ttctcttgag gaaactaata ggacactaac tagtgatgtt gccaatcttg caaatgagaa   3420
agaagaatta aataacaaat tgaaagatgt tcaagagcaa ctgtcaagat tgaaagatga   3480
agaaataagc gcagcagcta ttaaagcaca gtttgagaag cagctattaa cagaaagaac   3540
actcaaaact caagctgtga ataagttggc tgagatcatg aatcgaaaag aacctgtcaa   3600
gcgtggtaat gacacagatg tgcggagaaa agagaaggag aatagaaagc tacatatgga   3660
gcttaaatct gaacgtgaga aattgaccca gcagatgatc aagtatcaga aagaactgaa   3720
tgaaatgcag gcacaaatag ctgaagagag ccagattcga attgaactgc agatgacatt   3780
ggacagtaaa gacagtgaca ttgagcagct gcggtcacaa ctccaagcct tgcatattgg   3840
tctggatagt tccagtatag gcagtggacc aggggatgct gaggcagatg atgggtttcc   3900
agaatcaaga ttagaaggat ggctttcatt gcctgtacga aacaacacta agaaatttgg   3960
atgggttaaa aagtatgtga ttgtaagcag taagaagatt cttttctatg acagtgaaca   4020
agataaagaa caatccaatc cttacatggt tttagatata gacaagttat ttcatgtccg   4080
accagttaca cagacagatg tgtatagagc agatgctaaa gaaattccaa ggatattcca   4140
gattctgtat gccaatgaag gagaaagtaa gaaggaacaa gaatttccag tggagccagt   4200
tggagaaaaa tctaattata tttgccacaa gggacatgag tttattccta ctctttatca   4260
tttcccaacc aactgtgagg cttgtatgaa gcccctgtgg cacatgttta agcctcctcc   4320
tgctttggag tgccgccgtt gccacattaa gtgtcataaa gatcatatgg acaaaaagga   4380
ggagattata gcaccttgca aagtatatta tgatatttca acggcaaaga atctgttatt   4440
actagcaaat tctacagaag agcagcagaa gtgggttagt cggttggtga aaaagatacc   4500
taaaaagccc ccagctccag acccttttgc ccgatcatct cctagaactt caatgaagat   4560
acagcaaaac cagtctatta gacggccaag tcgacagctt gccccaaaca aacctagcta   4620
actgccttct atgaaagcag tcattattca aggtgatcgt attcttccag tgaaaacaag   4680
actgaaatat gatggcccaa aatttattaa aaagctatat tttcctgaga gactgataca   4740
tacactcata catatatgtg ttcccctttt ccctgtaata taaattacaa atctgggctc   4800
ctttgaagca acaggttgaa ccaacaatga ttggttgata gactaaggat atatgcaact   4860
cttccagact tttccataaa gctctctcgg cagtcgctca cactacagtg cacacaagga   4920
ttgagaagag ttaaaggcta aagaaaacat cttttctagc ttcaacagag aggtttcacc   4980
agcacattta ccagaagaat ctgggaatgg attccactac agtgatattg actgcatctt   5040
taagaagtga ccattatact gtgtatatat atataaacac acacacatat atatatatat   5100
atagtactct aatactgcaa gaaggttttt taaacttccc actttatttt ttatacacat   5160
taatcagata tcattacttg ctgcagttgc aactatgcac ttgtataaag ccataatgtt   5220
ggagtttata tcactcattc ctgtgtacct gatggaagtt gcatgttcat gtttaagcag   5280
```

-continued

```
ttactgtaac aagaagttta aagttaatta tatcagtttc ctaatgcttc atgataggca   5340
actttaccca ttttgaatgc cttaatttaa ttttttcaa agtctcagcc ctgtctgtat   5400
taaaaaacaa aaaaagcgtt taccagctct taggatgtaa actagctttg tggaagataa   5460
atcgtgcact atttttacac ataaatagtt atatcaatgt cagcctattt tgattaacaa   5520
atgtttttaa agtattattg gttatagaaa caataatgga tggtgttgga actaatatat   5580
ccttgatgtc tgtctattat tcattcaact ctttttacag acctcagtat tagtctgtga   5640
ctacaaaata ttttatttgc tttaaatttg ctggctaccc tagatgtgtt tttattcctg   5700
gtaaagacat ttgtgattac attttcacac ttaagattca aaatttttcc caaatataaa   5760
gaaaactaag acagactgta gatgcatttt aaatatttaa atatgatcct cagacatgca   5820
gctgtgtgtg gcagtatttt agtaccgggt taagaaaact ggcaactggg aagaagtggc   5880
ctcaaaggca cttaatttga tttttatttt ttaaatgctg tcaaagttac agtttacgca   5940
ggacattctt gccgtattct catgatccca gataagtgtg tgttttatac tgcaacaata   6000
tgcagcaatg gtaagcgtaa agttttttt tgtttttgtt tttgtttttt tttatattat   6060
gaagtctttt aacagtctct ctttatataa atacacagag tttggtatga tatttaaata   6120
catcatctgg ccaggcatgg tggcttacgc ctgtaatcct agcactttgg gaggccaaga   6180
cgggcggatc acctgaggtg aggagttcaa gaccagcctg cccaacatag tgaaactccg   6240
tctctaccaa tatacaaaaa ttagccgggc atgatggtgg tggcctgtaa tcccagctac   6300
ttgggaggct gagacaggag aatcgcttga acccaggaga cggtggttgc agtgagcgaa   6360
gatcgagcca ctgcactcca gcctgggcag ctgaacaaga ctccgtctc              6409
```

<210> SEQ ID NO 2
<211> LENGTH: 4167
<212> TYPE: DNA
<213> ORGANISM: Homo sapiens

<400> SEQUENCE: 2

```
atgagccggc ccccgccgac ggggaaaatg cccggcgccc ccgagaccgc gccgggggac     60
ggggcaggcg cgagccgcca gaggaagctg gaggcgctga tccgagaccc tcgctccccc    120
atcaacgtgg agagcttgct ggatggctta aattccttgg tccttgattt agattttcct    180
gctttgagga aaaacaagaa catagataat ttcttaaata gatatgagaa aattgtgaaa    240
aaaatcagag gtctacagat gaaggcagaa gactatgatg ttgtaaaagt tattggaaga    300
ggtgcttttg gtgaagtgca gttggttcgt cacaaggcat cgcagaaggt ttatgctatg    360
aagcttctta gtaagtttga aatgataaaa agatcagatt ctgccttttt ttgggaagaa    420
agagatatta tggcctttgc caatagcccc tgggtggttc agcttttta tgcctttcaa    480
gatgataggt atctgtacat ggtaatggag tacatgcctg gtggagacct tgtaaacctt    540
atgagtaatt atgatgtgcc tgaaaaatgg gccaaatttt acactgctga agttgttctt    600
gctctggatg caatacactc catgggttta atacacagag atgtgaagcc tgacaacatg    660
ctcttggata aacatggaca tctaaaatta gcagattttg gcacgtgtat gaagatggat    720
gaaacaggca tggtacattg tgatacagca gttggaacac cggattatat atcacctgag    780
gttctgaaat cacaaggggg tgatggtttc tatgggcgag aatgtgattg gtggtctgta    840
ggtgttttcc tttatgagat gctagtgggg gatactccat tttatgcgga ttcacttgta    900
ggaacatata gcaaaattat ggatcataag aattcactgt gtttccctga agatgcagaa    960
atttccaaac atgcaaagaa tctcatctgt gctttcttaa cagataggga ggtacgactt   1020
```

-continued

```
gggagaaatg gggtggaaga aatcagacag catcctttct ttaagaatga tcagtggcat   1080
tgggataaca taagagaaac ggcagctcct gtagtacctg aactcagcag tgacatagac   1140
agcagcaatt tcgatgacat tgaagatgac aaaggagatg tagaaacctt cccaattcct   1200
aaagcttttg ttggaaatca gctgcctttc atcggattta cctactatag agaaaattta   1260
ttattaagtg actctccatc ttgtagagaa aatgattcca tacaatcaag gaaaaatgaa   1320
gaaagtcaag agattcagaa aaaactgtat acattagaag aacatcttag caatgagatg   1380
caagccaaag aggaactgga acagaagtgc aaatctgtta atactcgcct agaaaaaaca   1440
gcaaaggagc tagaagagga gattacctta cggaaaagtg tggaatcagc attaagacag   1500
ttagaaagag aaaaggcgct tcttcagcac aaaaatgcag aatatcagag gaaagctgat   1560
catgaagcag acaaaaaacg aaatttggaa aatgatgtta acagcttaaa agatcaactt   1620
gaagatttga aaaaaagaaa tcaaaactct caaatatcca ctgagaaagt gaatcaactc   1680
cagagacaac tggatgaaac caatgcttta ctgcgaacag agtctgatac tgcagcccgg   1740
ttaaggaaaa cccaggcaga aagttcaaaa cagattcagc agctggaatc taacaataga   1800
gatctacaag ataaaaactg cctgctggag actgccaagt taaaacttga aaaggaattt   1860
atcaatcttc agtcagctct agaatctgaa aggagggatc gaacccatgg atcagagata   1920
attaatgatt tacaaggtag aatatgtggc ctagaagaag atttaaagaa cggcaaaatc   1980
ttactagcga aagtagaact ggagaagaga caacttcagg agagatttac tgatttggaa   2040
aaggaaaaaa gcaacatgga aatagatatg acataccaac taaaagttat acagcagagc   2100
ctagaacaag aagaagctga acataaggcc acaaaggcac gactagcaga taaaaataag   2160
atctatgagt ccatcgaaga agccaaatca gaagccatga aagaaatgga gaagaagctc   2220
ttggaggaaa gaactttaaa acagaaagtg gagaacctat tgctagaagc tgagaaaaga   2280
tgttctctat tagactgtga cctcaaacag tcacagcaga aaataaatga gctccttaaa   2340
cagaaagatg tgctaaatga ggatgttaga aacctgacat taaaaataga gcaagaaact   2400
cagaagcgct gccttacaca aaatgacctg aagatgcaaa cacaacaggt taacacacta   2460
aaaatgtcag aaaagcagtt aaagcaagaa aataaccatc tcatggaaat gaaaatgaac   2520
ttggaaaaac aaaatgctga acttcgaaaa gaacgtcagg atgcagatgg gcaaatgaaa   2580
gagctccagg atcagctcga agcagaacag tatttctcaa ccctttataa aacacaagtt   2640
agggagctta aagaagaatg tgaagaaaag accaaacttg gtaaagaatt gcagcagaag   2700
aaacaggaat tacaggatga acgggactct ttggctgccc aactggagat caccttgacc   2760
aaagcagatt ctgagcaact ggctcgttca attgctgaag aacaatattc tgatttggaa   2820
aaagagaaga tcatgaaaga gctggagatc aaagagatga tggctagaca caaacaggaa   2880
cttacggaaa aagatgctac aattgcttct cttgaggaaa ctaataggac actaactagt   2940
gatgttgcca atcttgcaaa tgagaaagaa gaattaaata acaaattgaa agatgttcaa   3000
gagcaactgt caagattgaa agatgaagaa ataagcgcag cagctattaa agcacagttt   3060
gagaagcagc tattaacaga aagaacactc aaaactcaag ctgtgaataa gttggctgag   3120
atcatgaatc gaaaagaacc tgtcaagcgt ggtaatgaca cagatgtgcg gagaaaagag   3180
aaggagaata gaaagctaca tatggagctt aaatctgaac gtgagaaatt gacccagcag   3240
atgatcaagt atcagaaaga actgaatgaa atgcaggcac aaatagctga agagagccag   3300
attcgaattg aactgcagat gacattggac agtaaagaca gtgacattga gcagctgcgg   3360
tcacaactcc aagccttgca tattggtctg gatagttcca gtataggcag tggaccaggg   3420
```

-continued gatgctgagg cagatgatgg gtttccagaa tcaagattag aaggatggct ttcattgcct 3480
gtacgaaaca acactaagaa atttggatgg gttaaaaagt atgtgattgt aagcagtaag 3540
aagattcttt tctatgacag tgaacaagat aaagaacaat ccaatcctta catggtttta 3600
gatatagaca agttatttca tgtccgacca gttacacaga cagatgtgta tagagcagat 3660
gctaaagaaa ttccaaggat attccagatt ctgtatgcca atgaaggaga aagtaagaag 3720
gaacaagaat ttccagtgga gccagttgga gaaaaatcta attatatttg ccacaaggga 3780
catgagttta ttcctactct ttatcatttc ccaaccaact gtgaggcttg tatgaagccc 3840
ctgtggcaca tgtttaagcc tcctcctgct ttggagtgcc gccgttgcca cattaagtgt 3900
cataaagatc atatggacaa aaaggaggag attatagcac cttgcaaagt atattatgat 3960
atttcaacgg caaagaatct gttattacta gcaaattcta cagaagagca gcagaagtgg 4020
gttagtcggt tggtgaaaaa gatacctaaa aagcccccag ctccagaccc ttttgcccga 4080
tcatctccta gaacttcaat gaagatacag caaaaccagt ctattagacg gccaagtcga 4140
cagcttgccc caaacaaacc tagctaa 4167

<210> SEQ ID NO 3
<211> LENGTH: 19
<212> TYPE: RNA
<213> ORGANISM: Homo sapiens

<400> SEQUENCE: 3
gugcaguugg uucgucaca 19

<210> SEQ ID NO 4
<211> LENGTH: 19
<212> TYPE: RNA
<213> ORGANISM: Homo sapiens

<400> SEQUENCE: 4
caaggcaucg cagaagguu 19

<210> SEQ ID NO 5
<211> LENGTH: 19
<212> TYPE: RNA
<213> ORGANISM: Homo sapiens

<400> SEQUENCE: 5
uagguaucug uacauggua 19

<210> SEQ ID NO 6
<211> LENGTH: 19
<212> TYPE: RNA
<213> ORGANISM: Homo sapiens

<400> SEQUENCE: 6
gguaucugua caugguaau 19

<210> SEQ ID NO 7
<211> LENGTH: 19
<212> TYPE: RNA
<213> ORGANISM: Homo sapiens

<400> SEQUENCE: 7
aacaggcaug guacauugu 19

-continued

<210> SEQ ID NO 8
<211> LENGTH: 19
<212> TYPE: RNA
<213> ORGANISM: Homo sapiens

<400> SEQUENCE: 8
acaccggauu auauaucac 19

<210> SEQ ID NO 9
<211> LENGTH: 19
<212> TYPE: RNA
<213> ORGANISM: Homo sapiens

<400> SEQUENCE: 9
ugcggauuca cuuguagga 19

<210> SEQ ID NO 10
<211> LENGTH: 19
<212> TYPE: RNA
<213> ORGANISM: Homo sapiens

<400> SEQUENCE: 10
cucagcagug acauagaca 19

<210> SEQ ID NO 11
<211> LENGTH: 19
<212> TYPE: RNA
<213> ORGANISM: Homo sapiens

<400> SEQUENCE: 11
gugacucucc aucuuguag 19

<210> SEQ ID NO 12
<211> LENGTH: 19
<212> TYPE: RNA
<213> ORGANISM: Homo sapiens

<400> SEQUENCE: 12
gaagaggaga uuaccuuac 19

<210> SEQ ID NO 13
<211> LENGTH: 19
<212> TYPE: RNA
<213> ORGANISM: Homo sapiens

<400> SEQUENCE: 13
aaguguggaa ucagcauua 19

<210> SEQ ID NO 14
<211> LENGTH: 19
<212> TYPE: RNA
<213> ORGANISM: Homo sapiens

<400> SEQUENCE: 14
aguguggaau cagcauuaa 19

<210> SEQ ID NO 15
<211> LENGTH: 19
<212> TYPE: RNA
<213> ORGANISM: Homo sapiens

<400> SEQUENCE: 15
gcagcuggaa ucuaacaau 19

-continued

<210> SEQ ID NO 16
<211> LENGTH: 19
<212> TYPE: RNA
<213> ORGANISM: Homo sapiens

<400> SEQUENCE: 16
gcugaacaua aggccacaa 19

<210> SEQ ID NO 17
<211> LENGTH: 19
<212> TYPE: RNA
<213> ORGANISM: Homo sapiens

<400> SEQUENCE: 17
aggcacgacu agcagauaa 19

<210> SEQ ID NO 18
<211> LENGTH: 19
<212> TYPE: RNA
<213> ORGANISM: Homo sapiens

<400> SEQUENCE: 18
agaucuauga guccaucga 19

<210> SEQ ID NO 19
<211> LENGTH: 19
<212> TYPE: RNA
<213> ORGANISM: Homo sapiens

<400> SEQUENCE: 19
gaucuaugag uccaucgaa 19

<210> SEQ ID NO 20
<211> LENGTH: 19
<212> TYPE: RNA
<213> ORGANISM: Homo sapiens

<400> SEQUENCE: 20
aaguggagaa ccuauugcu 19

<210> SEQ ID NO 21
<211> LENGTH: 19
<212> TYPE: RNA
<213> ORGANISM: Homo sapiens

<400> SEQUENCE: 21
cacaacaggu uaacacacu 19

<210> SEQ ID NO 22
<211> LENGTH: 19
<212> TYPE: RNA
<213> ORGANISM: Homo sapiens

<400> SEQUENCE: 22
caacagguua acacacuaa 19

<210> SEQ ID NO 23
<211> LENGTH: 19
<212> TYPE: RNA
<213> ORGANISM: Homo sapiens

<400> SEQUENCE: 23
gcucgaagca gaacaguau 19

-continued

<210> SEQ ID NO 24
<211> LENGTH: 19
<212> TYPE: RNA
<213> ORGANISM: Homo sapiens

<400> SEQUENCE: 24
cuaauaggac acuaacuag 19

<210> SEQ ID NO 25
<211> LENGTH: 19
<212> TYPE: RNA
<213> ORGANISM: Homo sapiens

<400> SEQUENCE: 25
auaagcgcag cagcuauua 19

<210> SEQ ID NO 26
<211> LENGTH: 19
<212> TYPE: RNA
<213> ORGANISM: Homo sapiens

<400> SEQUENCE: 26
uaagcgcagc agcuauuaa 19

<210> SEQ ID NO 27
<211> LENGTH: 19
<212> TYPE: RNA
<213> ORGANISM: Homo sapiens

<400> SEQUENCE: 27
acucaagcug ugaauaagu 19

<210> SEQ ID NO 28
<211> LENGTH: 19
<212> TYPE: RNA
<213> ORGANISM: Homo sapiens

<400> SEQUENCE: 28
cucaagcugu gaauaaguu 19

<210> SEQ ID NO 29
<211> LENGTH: 19
<212> TYPE: RNA
<213> ORGANISM: Homo sapiens

<400> SEQUENCE: 29
gaaccuguca agcguggua 19

<210> SEQ ID NO 30
<211> LENGTH: 19
<212> TYPE: RNA
<213> ORGANISM: Homo sapiens

<400> SEQUENCE: 30
accugucaag cgugguaau 19

<210> SEQ ID NO 31
<211> LENGTH: 19
<212> TYPE: RNA
<213> ORGANISM: Homo sapiens

<400> SEQUENCE: 31
agagagccag auucgaauu 19

-continued

<210> SEQ ID NO 32
<211> LENGTH: 19
<212> TYPE: RNA
<213> ORGANISM: Homo sapiens

<400> SEQUENCE: 32
gagagccaga uucgaauug 19

<210> SEQ ID NO 33
<211> LENGTH: 19
<212> TYPE: RNA
<213> ORGANISM: Homo sapiens

<400> SEQUENCE: 33
gccagauucg aauugaacu 19

<210> SEQ ID NO 34
<211> LENGTH: 19
<212> TYPE: RNA
<213> ORGANISM: Homo sapiens

<400> SEQUENCE: 34
uucgaauuga acugcagau 19

<210> SEQ ID NO 35
<211> LENGTH: 19
<212> TYPE: RNA
<213> ORGANISM: Homo sapiens

<400> SEQUENCE: 35
accaacugug aggcuugua 19

<210> SEQ ID NO 36
<211> LENGTH: 19
<212> TYPE: RNA
<213> ORGANISM: Homo sapiens

<400> SEQUENCE: 36
acugugaggc uuguaugaa 19

<210> SEQ ID NO 37
<211> LENGTH: 19
<212> TYPE: RNA
<213> ORGANISM: Homo sapiens

<400> SEQUENCE: 37
cugugaggcu uguaugaag 19

<210> SEQ ID NO 38
<211> LENGTH: 19
<212> TYPE: RNA
<213> ORGANISM: Homo sapiens

<400> SEQUENCE: 38
uucaagguga ucguauucu 19

<210> SEQ ID NO 39
<211> LENGTH: 19
<212> TYPE: RNA
<213> ORGANISM: Homo sapiens

<400> SEQUENCE: 39
gacugauaca uacacucau 19

-continued

<210> SEQ ID NO 40
<211> LENGTH: 19
<212> TYPE: RNA
<213> ORGANISM: Homo sapiens

<400> SEQUENCE: 40
uugguugaua gacuaagga 19

<210> SEQ ID NO 41
<211> LENGTH: 19
<212> TYPE: RNA
<213> ORGANISM: Homo sapiens

<400> SEQUENCE: 41
cuaaggauau augcaacuc 19

<210> SEQ ID NO 42
<211> LENGTH: 19
<212> TYPE: RNA
<213> ORGANISM: Homo sapiens

<400> SEQUENCE: 42
aggauauaug caacucuuc 19

<210> SEQ ID NO 43
<211> LENGTH: 19
<212> TYPE: RNA
<213> ORGANISM: Homo sapiens

<400> SEQUENCE: 43
agugaccauu auacugugu 19

<210> SEQ ID NO 44
<211> LENGTH: 19
<212> TYPE: RNA
<213> ORGANISM: Homo sapiens

<400> SEQUENCE: 44
gugaccauua uacugugua 19

<210> SEQ ID NO 45
<211> LENGTH: 19
<212> TYPE: RNA
<213> ORGANISM: Homo sapiens

<400> SEQUENCE: 45
ccugauggaa guugcaugu 19

<210> SEQ ID NO 46
<211> LENGTH: 19
<212> TYPE: RNA
<213> ORGANISM: Homo sapiens

<400> SEQUENCE: 46
gaccucagua uuagucugu 19

<210> SEQ ID NO 47
<211> LENGTH: 19
<212> TYPE: RNA
<213> ORGANISM: Homo sapiens

<400> SEQUENCE: 47
ggacauucuu gccguauuc 19

-continued

<210> SEQ ID NO 48
<211> LENGTH: 19
<212> TYPE: RNA
<213> ORGANISM: Homo sapiens

<400> SEQUENCE: 48
acaauaugca gcaauggua 19

<210> SEQ ID NO 49
<211> LENGTH: 19
<212> TYPE: RNA
<213> ORGANISM: Homo sapiens

<400> SEQUENCE: 49
cuccgucucu accaauaua 19

<210> SEQ ID NO 50
<211> LENGTH: 23
<212> TYPE: DNA
<213> ORGANISM: Homo sapiens

<400> SEQUENCE: 50
gugcaguugg uucgucacad tdt 23

<210> SEQ ID NO 51
<211> LENGTH: 23
<212> TYPE: DNA
<213> ORGANISM: Homo sapiens

<400> SEQUENCE: 51
ugugacgaac caacugcacd tdt 23

<210> SEQ ID NO 52
<211> LENGTH: 23
<212> TYPE: DNA
<213> ORGANISM: Homo sapiens

<400> SEQUENCE: 52
cucagcagug acauagacad tdt 23

<210> SEQ ID NO 53
<211> LENGTH: 23
<212> TYPE: DNA
<213> ORGANISM: Homo sapiens

<400> SEQUENCE: 53
ugucuauguc acugcugagd tdt 23

<210> SEQ ID NO 54
<211> LENGTH: 23
<212> TYPE: DNA
<213> ORGANISM: Homo sapiens

<400> SEQUENCE: 54
gugacucucc aucuuguagd tdt 23

<210> SEQ ID NO 55
<211> LENGTH: 23
<212> TYPE: DNA
<213> ORGANISM: Homo sapiens

<400> SEQUENCE: 55
cuacaagaug gagagucacd tdt 23

-continued

<210> SEQ ID NO 56
<211> LENGTH: 23
<212> TYPE: DNA
<213> ORGANISM: Homo sapiens

<400> SEQUENCE: 56
gcugaacaua aggccacaad tdt 23

<210> SEQ ID NO 57
<211> LENGTH: 23
<212> TYPE: DNA
<213> ORGANISM: Homo sapiens

<400> SEQUENCE: 57
uuguggccuu auguucagcd tdt 23

<210> SEQ ID NO 58
<211> LENGTH: 23
<212> TYPE: DNA
<213> ORGANISM: Homo sapiens

<400> SEQUENCE: 58
aggcacgacu agcagauaad tdt 23

<210> SEQ ID NO 59
<211> LENGTH: 23
<212> TYPE: DNA
<213> ORGANISM: Homo sapiens

<400> SEQUENCE: 59
uuaucugcua gucgugccud tdt 23

<210> SEQ ID NO 60
<211> LENGTH: 23
<212> TYPE: DNA
<213> ORGANISM: Homo sapiens

<400> SEQUENCE: 60
gaucuaugag uccaucgaad tdt 23

<210> SEQ ID NO 61
<211> LENGTH: 23
<212> TYPE: DNA
<213> ORGANISM: Homo sapiens

<400> SEQUENCE: 61
uucgauggac ucauagaucd tdt 23

<210> SEQ ID NO 62
<211> LENGTH: 23
<212> TYPE: DNA
<213> ORGANISM: Homo sapiens

<400> SEQUENCE: 62
cacaacaggu uaacacacud tdt 23

<210> SEQ ID NO 63
<211> LENGTH: 23
<212> TYPE: DNA
<213> ORGANISM: Homo sapiens

<400> SEQUENCE: 63
aguguguuaa ccuguugugd tdt 23

-continued

<210> SEQ ID NO 64
<211> LENGTH: 23
<212> TYPE: DNA
<213> ORGANISM: Homo sapiens

<400> SEQUENCE: 64
auaagcgcag cagcuauuad tdt 23

<210> SEQ ID NO 65
<211> LENGTH: 23
<212> TYPE: DNA
<213> ORGANISM: Homo sapiens

<400> SEQUENCE: 65
uaauagcugc ugcgcuuaud tdt 23

<210> SEQ ID NO 66
<211> LENGTH: 23
<212> TYPE: DNA
<213> ORGANISM: Homo sapiens

<400> SEQUENCE: 66
uaagcgcagc agcuauuaad tdt 23

<210> SEQ ID NO 67
<211> LENGTH: 23
<212> TYPE: DNA
<213> ORGANISM: Homo sapiens

<400> SEQUENCE: 67
uuaauagcug cugcgcuuad tdt 23

<210> SEQ ID NO 68
<211> LENGTH: 23
<212> TYPE: DNA
<213> ORGANISM: Homo sapiens

<400> SEQUENCE: 68
gaaccuguca agcgugguad tdt 23

<210> SEQ ID NO 69
<211> LENGTH: 23
<212> TYPE: DNA
<213> ORGANISM: Homo sapiens

<400> SEQUENCE: 69
uaccacgcuu gacagguucd tdt 23

<210> SEQ ID NO 70
<211> LENGTH: 23
<212> TYPE: DNA
<213> ORGANISM: Homo sapiens

<400> SEQUENCE: 70
gagagccaga uucgaauugd tdt 23

<210> SEQ ID NO 71
<211> LENGTH: 23
<212> TYPE: DNA
<213> ORGANISM: Homo sapiens

<400> SEQUENCE: 71
caauucgaau cuggcucucd tdt 23

-continued

<210> SEQ ID NO 72
<211> LENGTH: 23
<212> TYPE: DNA
<213> ORGANISM: Homo sapiens

<400> SEQUENCE: 72
cugugaggcu uguaugaagd tdt 23

<210> SEQ ID NO 73
<211> LENGTH: 23
<212> TYPE: DNA
<213> ORGANISM: Homo sapiens

<400> SEQUENCE: 73
cuucauacaa gccucacagd tdt 23

<210> SEQ ID NO 74
<211> LENGTH: 52
<212> TYPE: RNA
<213> ORGANISM: Homo sapiens

<400> SEQUENCE: 74
gugcaguugg uucgucacau ucaagagaug ucuaugucac ugcugaguuu uu 52

<210> SEQ ID NO 75
<211> LENGTH: 52
<212> TYPE: RNA
<213> ORGANISM: Homo sapiens

<400> SEQUENCE: 75
cucagcagug acauagacau ucaagagaug ugacgaacca acugcacuuu uu 52

<210> SEQ ID NO 76
<211> LENGTH: 52
<212> TYPE: RNA
<213> ORGANISM: Homo sapiens

<400> SEQUENCE: 76
gugacucucc aucuuguagu ucaagagacu acaagaugga gagucacuuu uu 52

<210> SEQ ID NO 77
<211> LENGTH: 52
<212> TYPE: RNA
<213> ORGANISM: Homo sapiens

<400> SEQUENCE: 77
gcugaacaua aggccacaau ucaagagauu guggccuuau guucagcuuu uu 52

<210> SEQ ID NO 78
<211> LENGTH: 52
<212> TYPE: RNA
<213> ORGANISM: Homo sapiens

<400> SEQUENCE: 78
aggcacgacu acgagauaau ucaagagauu aucugcuagu cgugccuuuu uu 52

<210> SEQ ID NO 79
<211> LENGTH: 52
<212> TYPE: RNA
<213> ORGANISM: Homo sapiens

<400> SEQUENCE: 79
gaucuaugag uccaucgaau ucaagagauu cgauggacuc auagaucuuu uu 52

-continued

```
<210> SEQ ID NO 80
<211> LENGTH: 52
<212> TYPE: RNA
<213> ORGANISM: Homo sapiens

<400> SEQUENCE: 80

cacaacaggu uaacacacuu ucaagagaag uguguuaacc uguuguguuu uu            52


<210> SEQ ID NO 81
<211> LENGTH: 52
<212> TYPE: RNA
<213> ORGANISM: Homo sapiens

<400> SEQUENCE: 81

auaagcgcag cagcuauuau ucaagagaua auagcugcug cgcuuauuuu uu            52


<210> SEQ ID NO 82
<211> LENGTH: 52
<212> TYPE: RNA
<213> ORGANISM: Homo sapiens

<400> SEQUENCE: 82

uaagcgcagc agcuauuaau ucaagagauu aauagcugcu gcgcuuauuu uu            52


<210> SEQ ID NO 83
<211> LENGTH: 52
<212> TYPE: RNA
<213> ORGANISM: Homo sapiens

<400> SEQUENCE: 83

gaaccuguca agcgugguau ucaagagaua ccacgcuuga cagguucuuu uu            52


<210> SEQ ID NO 84
<211> LENGTH: 52
<212> TYPE: RNA
<213> ORGANISM: Homo sapiens

<400> SEQUENCE: 84

gagagccaga uucgaauugu ucaagagaca auucgaaucu ggcucucuuu uu            52


<210> SEQ ID NO 85
<211> LENGTH: 52
<212> TYPE: RNA
<213> ORGANISM: Homo sapiens

<400> SEQUENCE: 85

cugugaggcu uguaugaagu ucaagagacu ucauacaagc cucacaguuu uu            52
```